US011234720B2

(12) United States Patent
Goble et al.

(10) Patent No.: US 11,234,720 B2
(45) Date of Patent: Feb. 1, 2022

(54) KNEE INSTRUMENTS AND METHODS

(71) Applicant: E. MARLOWE GOBLE, Logan, UT (US)

(72) Inventors: E. Marlowe Goble, Logan, UT (US); Daniel J. Triplett, Providence, UT (US)

(73) Assignee: E. Marlowe Goble, Logan, UT (US)

( * ) Notice: Subject to any disclaimer, the term of this patent is extended or adjusted under 35 U.S.C. 154(b) by 267 days.

(21) Appl. No.: 16/287,976

(22) Filed: Feb. 27, 2019

(65) Prior Publication Data

US 2019/0274696 A1    Sep. 12, 2019

Related U.S. Application Data

(60) Provisional application No. 62/640,006, filed on Mar. 7, 2018.

(51) Int. Cl.
*A61B 17/17* (2006.01)
*A61B 17/15* (2006.01)
(Continued)

(52) U.S. Cl.
CPC ........ *A61B 17/1764* (2013.01); *A61B 17/155* (2013.01); *A61B 17/1675* (2013.01);
(Continued)

(58) Field of Classification Search
CPC .. A61B 17/155; A61B 17/1764; A61B 17/154
See application file for complete search history.

(56) References Cited

U.S. PATENT DOCUMENTS

| 3,949,428 A | 4/1976 | Cavendish |
| 4,187,559 A | 2/1980 | Grell |
| (Continued) | | |

FOREIGN PATENT DOCUMENTS

| EP | 2145590 | 5/2012 |
| EP | 2626044 | 12/2016 |
| (Continued) | | |

OTHER PUBLICATIONS

DePuy Synthes. P.F.C. Sigma Knee Systems. Surgical Technique. 2013. pp. 19-23.
(Continued)

*Primary Examiner* — Samuel S Hanna
(74) *Attorney, Agent, or Firm* — David Meibos; Maywood IP Law

(57) ABSTRACT

An adjustable femoral pin guide assembly includes a base and a femoral extension rod assembly. The base may be rotated to align with the femoral shaft axis while the femoral extension rod assembly aligns with the leg mechanical axis. An adjustable distal femoral cut guide assembly may be adjusted to provide a range of varus/valgus angles for the distal femoral resection. An adjustable, single-use, disposable four-in-one cut guide may be adjusted to position saw slots for the anterior and posterior femoral resections and the anterior and posterior chamfer cuts for various size femoral components, then locked. A foot holder assembly includes an anterior tibial target that may be adjusted in three dimensions relative to the tibia. A femoral sizing guide includes a sliding drill guide to position a pin in the distal femur in a specific orientation relative to the leg mechanical axis.

20 Claims, 46 Drawing Sheets

(51) Int. Cl.
  *A61F 2/46* (2006.01)
  *A61B 17/16* (2006.01)
  A61B 90/00 (2016.01)
  A61F 2/38 (2006.01)

(52) U.S. Cl.
  CPC ........ *A61F 2/461* (2013.01); *A61B 2090/067* (2016.02); *A61F 2/389* (2013.01); *A61F 2/3859* (2013.01)

(56) References Cited

U.S. PATENT DOCUMENTS

| | | |
|---|---|---|
| 4,242,758 A | 1/1981 | Amis |
| 4,364,389 A | 12/1982 | Keller |
| 4,426,071 A | 1/1984 | Klevstad |
| 4,457,307 A | 7/1984 | Stillwell |
| 4,502,474 A | 3/1985 | Comparetto |
| 4,509,511 A | 4/1985 | Neufeld |
| 4,524,766 A | 6/1985 | Petersen |
| 4,565,192 A | 1/1986 | Shapiro |
| 4,566,448 A | 1/1986 | Rohr, Jr. |
| 4,567,885 A | 2/1986 | Androphy |
| 4,567,886 A | 2/1986 | Petersen |
| 4,624,250 A | 11/1986 | Saunders |
| 4,627,425 A | 12/1986 | Reese |
| 4,677,973 A | 7/1987 | Slocum |
| 4,703,751 A | 11/1987 | Pohl |
| 4,718,414 A | 1/1988 | Saunders |
| 4,722,330 A | 2/1988 | Russell |
| 4,736,737 A | 4/1988 | Fargie |
| 4,759,350 A | 7/1988 | Dunn |
| 4,773,407 A | 9/1988 | Petersen |
| 4,892,093 A | 1/1990 | Zarnowski |
| 4,893,619 A | 1/1990 | Dale |
| 4,907,578 A | 3/1990 | Petersen |
| 4,926,847 A | 5/1990 | Luckman |
| 4,938,762 A | 7/1990 | Wehrli |
| 4,944,756 A | 7/1990 | Kenna |
| 4,944,760 A | 7/1990 | Kenna |
| 4,952,213 A | 8/1990 | Bowman |
| 5,002,545 A | 3/1991 | Whiteside |
| 5,007,912 A | 4/1991 | Albrektsson |
| 5,021,055 A | 6/1991 | Burkinshaw |
| 5,037,423 A | 8/1991 | Kenna |
| 5,047,032 A | 9/1991 | Jellicoe |
| 5,049,149 A | 9/1991 | Schmidt |
| 5,053,037 A | 10/1991 | Lackey |
| 5,053,039 A | 10/1991 | Hofmann |
| 5,062,852 A | 11/1991 | Dorr |
| 5,395,377 A | 3/1995 | Petersen |
| 5,472,415 A | 12/1995 | King |
| 5,514,143 A | 5/1996 | Bonutti |
| 5,601,563 A | 2/1997 | Burke |
| 5,624,444 A | 4/1997 | Wixon |
| 5,676,668 A | 10/1997 | McCue et al. |
| 5,688,281 A | 11/1997 | Cripe |
| 5,709,689 A | 1/1998 | Ferrante |
| 5,720,752 A | 2/1998 | Elliott |
| 5,749,876 A | 5/1998 | Duvillier |
| 5,925,049 A | 7/1999 | Gustilo |
| 6,013,081 A | 1/2000 | Burkinshaw |
| 6,022,332 A | 2/2000 | Nelson |
| 6,234,173 B1 | 5/2001 | Hajianpour |
| 6,258,096 B1 | 7/2001 | Seki |
| 6,554,837 B1 | 4/2003 | Hauri |
| 6,852,115 B2 | 2/2005 | Kinnett |
| 7,104,997 B2 | 9/2006 | Lionberger |
| 7,547,307 B2 | 6/2009 | Carson |
| 7,621,920 B2 | 11/2009 | Claypool |
| 7,641,660 B2 | 1/2010 | Lakin |
| 7,658,741 B2 | 2/2010 | Claypool |
| 7,665,167 B2 | 2/2010 | Branch |
| 7,780,672 B2 | 8/2010 | Metzger |
| 7,947,862 B2 | 5/2011 | Livorsi |
| 8,052,692 B2 | 11/2011 | Lionberger |
| 8,070,752 B2 | 12/2011 | Metzger |
| 8,382,766 B2 | 2/2013 | Warkentine |
| 8,518,051 B2 | 8/2013 | Shoham |
| 9,005,207 B2 | 4/2015 | Dodds |
| 9,033,991 B2 | 5/2015 | Salehi et al. |
| 9,386,994 B2 | 7/2016 | Agnihotri et al. |
| 9,572,586 B2 | 2/2017 | van der Walt |
| 10,405,871 B1 | 9/2019 | Bini |
| 2002/0173797 A1 | 11/2002 | Van Zile |
| 2004/0030275 A1 | 2/2004 | Morinaka |
| 2005/0149037 A1 | 7/2005 | Steffensmeier |
| 2007/0173843 A1 | 7/2007 | Matityahu |
| 2007/0197944 A1 | 8/2007 | Bruce |
| 2009/0082774 A1* | 3/2009 | Oti ................. A61B 17/155 606/87 |
| 2009/0088768 A1 | 4/2009 | Grant |
| 2010/0016858 A1 | 1/2010 | Michel |
| 2010/0331847 A1 | 12/2010 | Wilkinson |
| 2011/0009868 A1 | 1/2011 | Sato |
| 2012/0136359 A1 | 5/2012 | Grunder |
| 2012/0259335 A1 | 10/2012 | Scifert |
| 2012/0316564 A1 | 12/2012 | Serbousek |
| 2013/0090688 A1 | 4/2013 | Montello et al. |
| 2013/0184713 A1 | 7/2013 | Bojarski et al. |
| 2013/0204259 A1 | 8/2013 | Zajac |
| 2013/0296865 A1 | 11/2013 | Aram et al. |
| 2014/0005672 A1 | 1/2014 | Edwards |
| 2014/0114319 A1 | 4/2014 | Wilkinson |
| 2014/0243991 A1 | 8/2014 | Collazo |
| 2015/0157337 A1 | 6/2015 | Wolf |
| 2015/0305754 A1 | 10/2015 | Metzger |
| 2016/0051268 A1 | 2/2016 | Seitlinger |
| 2016/0213382 A1 | 7/2016 | Maeda |
| 2016/0278938 A1 | 9/2016 | Goble |
| 2016/0287238 A1 | 10/2016 | DeMayo |
| 2016/0361178 A1 | 12/2016 | Budhabhatti |
| 2017/0100132 A1 | 4/2017 | Collazo |
| 2017/0290597 A1* | 10/2017 | Goble ................. A61B 17/155 |
| 2018/0280038 A1 | 10/2018 | Goble |
| 2018/0296232 A1 | 10/2018 | Nielsen |
| 2019/0029700 A1 | 1/2019 | Free et al. |

FOREIGN PATENT DOCUMENTS

| | | |
|---|---|---|
| EP | 3273877 | 1/2018 |
| EP | 3474757 | 5/2019 |
| FR | 2819168 | 7/2002 |
| WO | WO2016154606 | 9/2016 |
| WO | WO2017223353 | 12/2017 |

OTHER PUBLICATIONS

Insall, John N. Surgery of the Knee. New York: Churchill Livingstone, 1984. pp. 631-365.

Tiftikçi U, Serbest S, Burulday V. Can Achilles tendon be used as a new distal landmark for coronal tibial component alignment in total knee replacement surgery? An observational MRI study. Therapeutics and Clinical Risk Management. 2017:13. pp. 81-86.

International Search Report and Written Opinion dated Nov. 25, 2020 for corresponding International Application No. PCT/US2020/051384.

Supplementary Partial European Search Report dated Oct. 19, 2021 for corresponding European Patent Application No. 19764846.2.

* cited by examiner

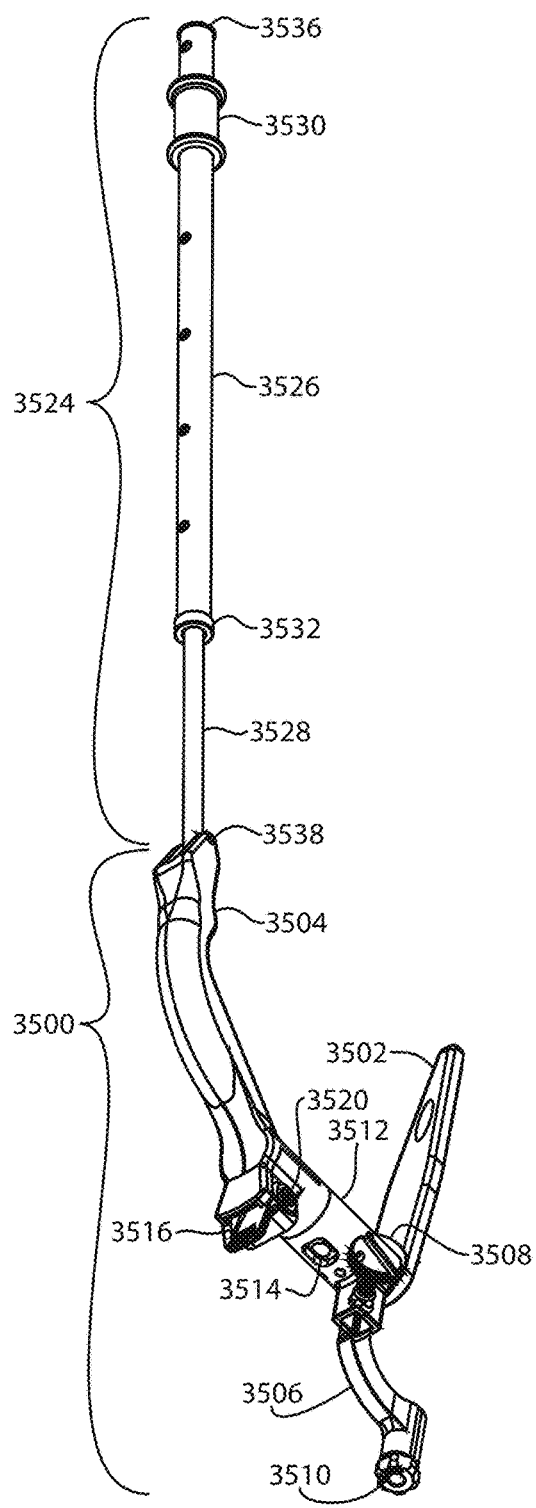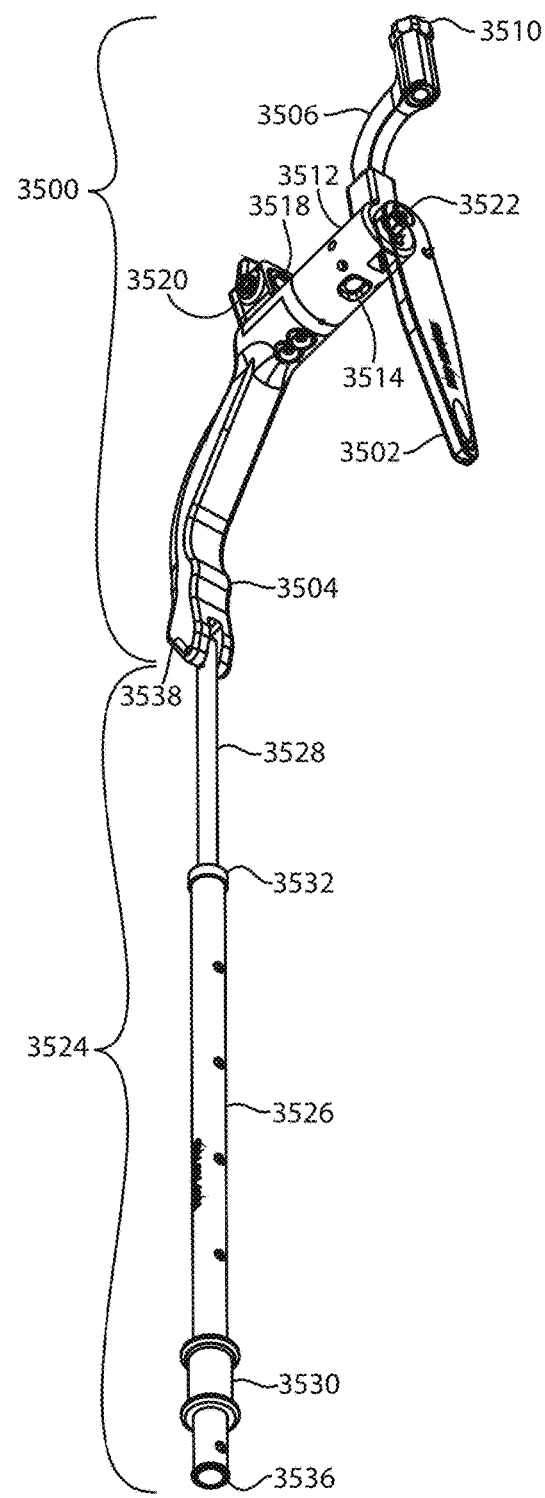
FIG. 1
FIG. 2

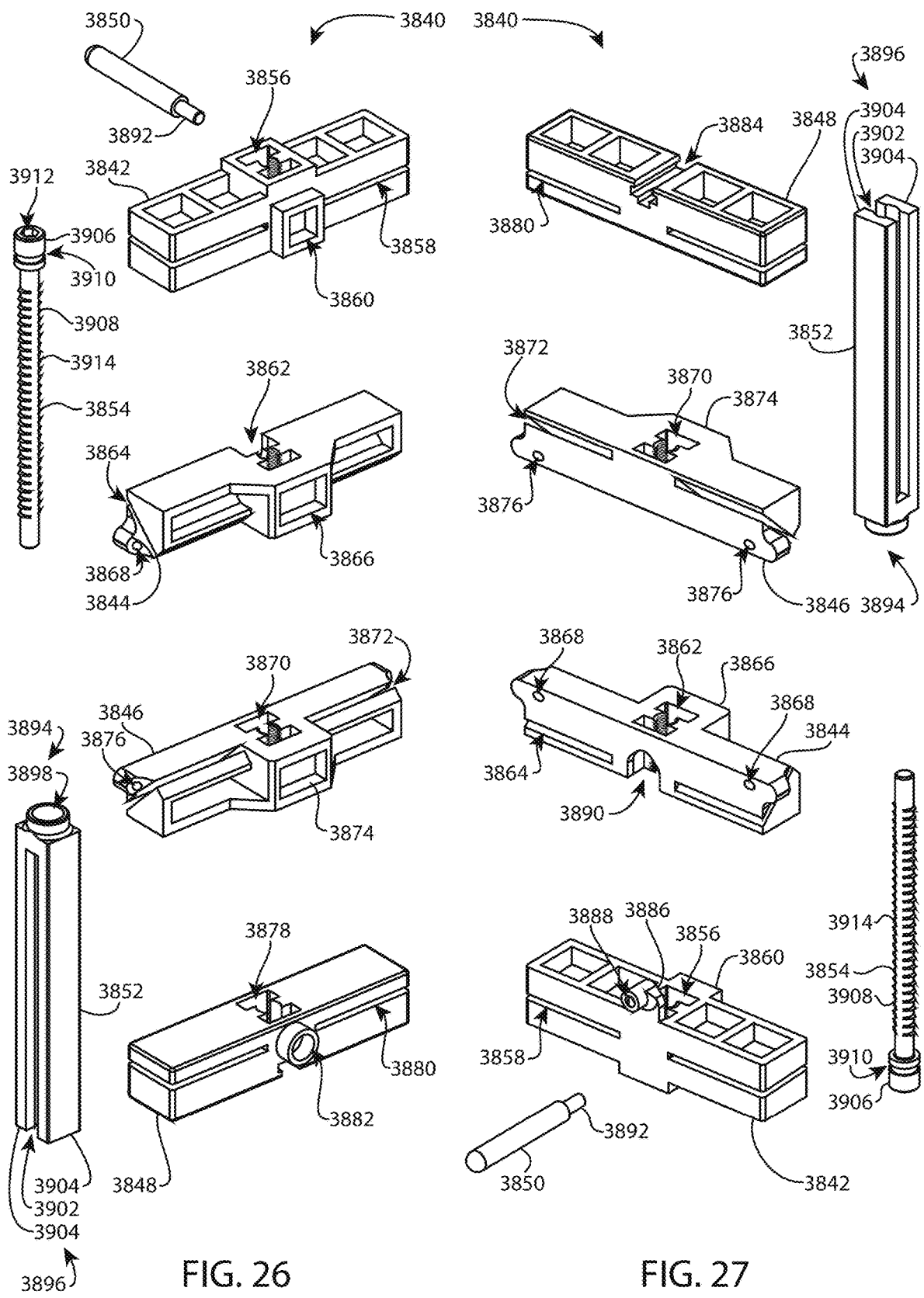

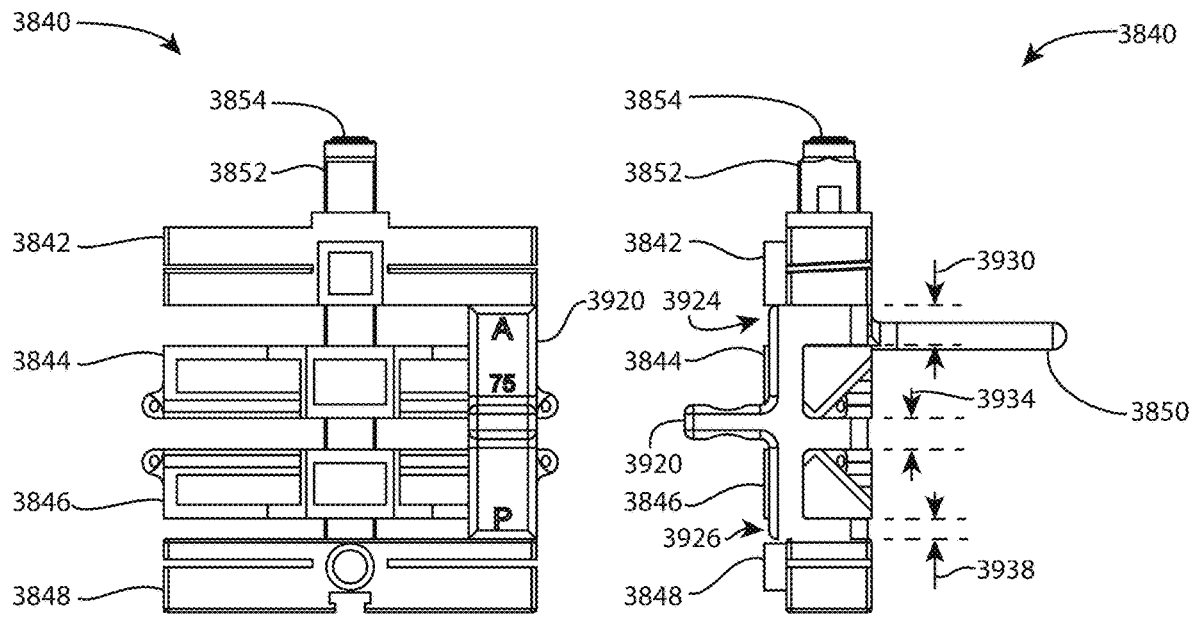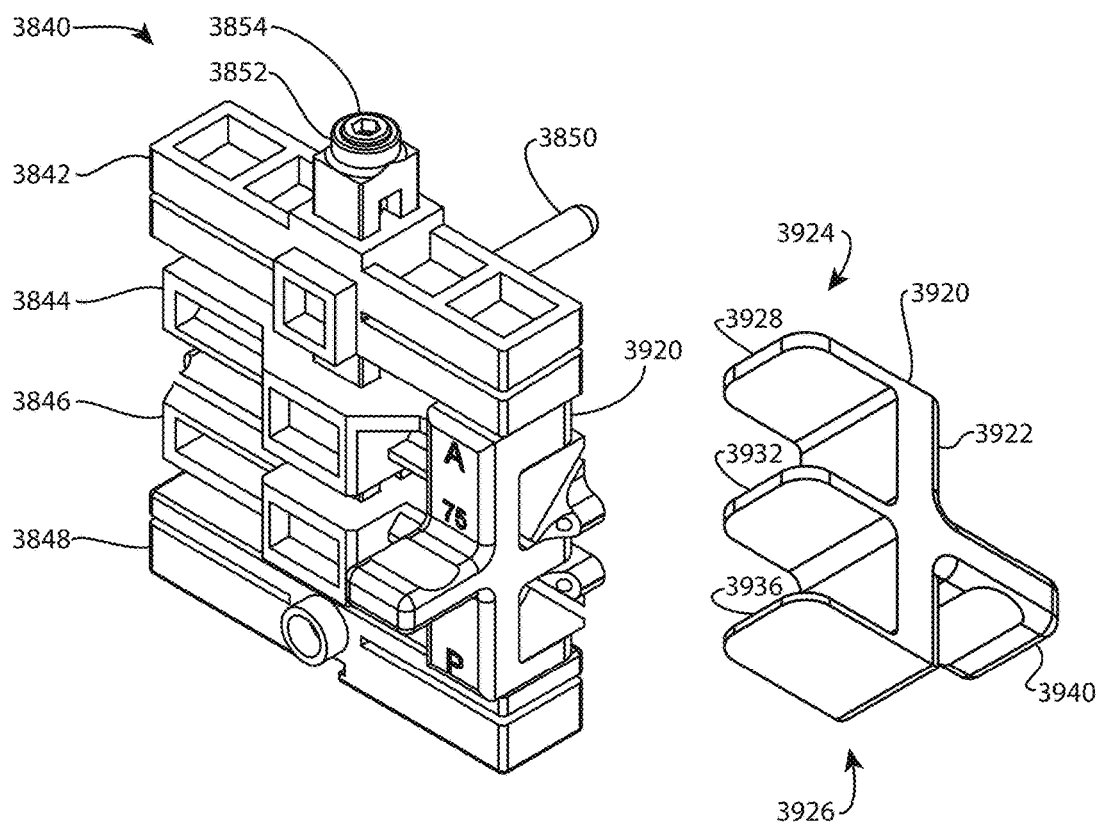

KNEE INSTRUMENTS AND METHODS

CROSS-REFERENCE TO RELATED APPLICATIONS

The present application claims the benefit of

U.S. Provisional Application Ser. No. 62/640,006, entitled KNEE INSTRUMENTS AND METHODS, filed on Mar. 7, 2018.

The present application is related to:

U.S. patent application Ser. No. 15/630,555, entitled KNEE INSTRUMENTS AND METHODS, filed on Jun. 22, 2017, which is pending.

U.S. patent application Ser. No. 15/630,555 claims the benefit of:

U.S. Provisional Application Ser. No. 62/353,553, entitled KNEE INSTRUMENTS AND METHODS, filed on Jun. 22, 2016.

U.S. patent application Ser. No. 15/630,555 is a continuation-in-part of:

U.S. patent application Ser. No. 15/081,828, entitled KNEE INSTRUMENTS AND METHODS, filed on Mar. 25, 2016, which is pending.

U.S. patent application Ser. No. 15/081,828 claims the benefit of:

U.S. Provisional Patent Application No. 62/302,787, entitled KNEE INSTRUMENTS AND METHODS, filed on Mar. 2, 2016; and U.S. Provisional Patent Application No. 62/138,307, entitled KNEE INSTRUMENTS AND METHODS, filed on Mar. 25, 2015.

The foregoing are incorporated by reference as though set forth herein in their entirety.

TECHNICAL FIELD

The present disclosure relates to instruments and methods to improve femoral and tibial alignment during knee arthroplasty. More specifically, the present disclosure relates to an adjustable femoral pin guide assembly, an adjustable distal femoral cut guide assembly, an adjustable four-in-one cut guide assembly that may be particularly adapted as a single use disposable item, an adjustable foot holder assembly, an adjustable femoral sizing guide assembly, a static four-in-one cut guide, an Achilles tendon alignment guide, and a multi-pin guide assembly.

BACKGROUND

The success of knee arthroplasty is largely dependent upon the accuracy of the distal femoral and proximal tibial bone cuts or resections. When the resections are well aligned to the mechanical axis of the leg and patient knee geometry and orientation, the reconstructed knee functions better and lasts longer. The problem to be solved is to devise instruments and methods which provide exceptional accuracy in combination with simplicity, speed, and value.

SUMMARY

The various systems and methods of the present technology have been developed in response to the present state of the art, and in particular, in response to the problems and needs in the art that have not yet been fully solved by currently available knee arthroplasty instrument systems and methods. The systems and methods of the present technology may provide improved anatomical referencing, sizing, and alignment comparable to computerized navigation systems, at a fraction of the cost.

To achieve the foregoing, and in accordance with the technology as embodied and broadly described herein, in an aspect of the technology, a femoral pin guide assembly includes: a femoral rod extending along a central longitudinal rod axis; a base plate including three points for contacting a bone surface, wherein the three points establish a base plane, wherein the base plate includes a maximum dimension extending along a base axis, wherein the base axis is parallel to the base plane; and a drill sleeve rigidly fixed to the base plate, wherein the drill sleeve includes a through hole extending along a drill axis; wherein, in a view perpendicular to the base plane, the base axis forms an angle with the rod axis; wherein the base plate is movable relative to the femoral rod to change the angle.

In another aspect of the technology, a distal femoral cut guide for making a distal femoral resection includes: a body including a bone facing surface and a saw slot, wherein the saw slot extends through the bone facing surface; and a slide component coupled to the body, wherein the slide component includes a bone facing surface and extends between a first end and an opposite second end, wherein a first hole extends through the slide component bone facing surface at the first end, wherein a second hole extends through the slide component bone facing surface at the second end, wherein a slide axis extends between the centers of the first and second holes, wherein the slide component pivots relative to the saw slot about the center of the first hole; wherein the distal femoral cut guide includes a first setting in which the slide axis is parallel to the saw slot; wherein the distal femoral cut guide includes a second setting in which the slide axis forms an angle with the saw slot, wherein the angle is greater than zero degrees.

In yet another aspect of the technology, a four-in-one femoral cut guide system for knee arthroplasty includes: a four-in-one cut guide including: an anterior cut guide with an anterior resection saw slot; an anterior chamfer guide with an anterior chamfer saw slot; a posterior chamfer guide with a posterior chamfer saw slot; and a posterior cut guide with a posterior resection saw slot; wherein the four-in-one cut guide includes an unlocked configuration in which the anterior cut guide, anterior chamfer guide, and posterior chamfer guide are independently movable relative to the posterior cut guide along an anterior-posterior direction, and a locked configuration in which the anterior cut guide, anterior chamfer guide, posterior chamfer guide, and posterior cut guide are all fixed relative to each other.

Embodiments of this aspect may include one or more of the following attributes. The system, further including: a spacer for engagement with the four-in-one cut guide, wherein the spacer includes an anterior arm including a first anterior-posterior thickness, a middle arm including a second anterior-posterior thickness, and a posterior arm including a third anterior-posterior thickness, wherein the anterior, middle, and posterior arms are coupled to a spacer body; wherein when the spacer is engaged with the four-in-one cut guide, the anterior arm extends between the anterior cut guide and the anterior chamfer guide, the middle arm extends between the anterior chamfer guide and the posterior chamfer guide, and the posterior arm extends between the posterior chamfer guide and the posterior cut guide. The system, further including: a spacer for engagement with the four-in-one cut guide, wherein the spacer includes first, second, third, and fourth end effectors coupled to a spacer body, wherein the second end effector is posterior to the first end effector, wherein the third end effector is posterior to the second end effector, wherein the fourth end effector is posterior to the third end effector; wherein when the spacer is engaged with the four-in-one cut guide, the first end effector couples to the anterior cut guide, the second end effector couples to the anterior chamfer guide, the third end effector couples to the posterior chamfer guide, and the fourth end effector couples to the posterior cut guide.

In yet another aspect of the technology, a foot holder assembly includes: a foot support including a first rail, wherein the first rail extends along a proximal-distal direction; a frame including a first channel, wherein the first channel is slidingly engaged with the first rail, wherein the frame extends anteriorly from the first channel, wherein the frame includes a slot that extends along a medial-lateral direction; a clamp assembly slidingly engaged with the frame slot, wherein the clamp assembly includes a second channel that extends along an anterior-posterior direction; and a tibial target including a second rail, wherein the second rail is slidingly engaged with the second channel.

In yet another aspect of the technology, a four-in-one femoral cut guide system for knee arthroplasty includes: a femoral sizing guide including medial and lateral paddles for contacting posterior aspects of medial and lateral femoral condyles, a slider for contacting a distal aspect of the femur, and a stylus for contacting an anterior aspect of the femur, wherein the slider includes a hole extending along a proximal-distal direction, wherein the slider is movable along a medial-lateral direction relative to the medial and lateral paddles to center the slider hole in the medial-lateral width of the femur; and a four-in-one cut guide including an anterior resection saw slot, an anterior chamfer saw slot, a posterior chamfer saw slot, a posterior resection saw slot, and a cut guide hole centered in the medial-lateral width of the four-in-one cut guide, wherein the cut guide hole corresponds to the slider hole.

In yet another aspect of the technology, a foot holder assembly includes: a foot support including a posterior window; and an Achilles tendon alignment sub-assembly coupled to the foot support and including an Achilles receiver including an anterior notch for receiving an Achilles tendon of a patient, wherein the Achilles tendon alignment sub-assembly is movable between an anterior state and a posterior state, wherein in the anterior state, the Achilles receiver protrudes anteriorly through the window, wherein in the posterior state, the Achilles receiver is retracted posteriorly relative to the anterior state.

Embodiments of this aspect may include a target sub-assembly coupled to the foot support and including a target, wherein the target is anterior to the Achilles receiver in the anterior state, wherein the target is aligned with the anterior notch.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 1 is an oblique view of a femoral pin guide assembly coupled to a femoral extension rod assembly;

FIG. 2 is another oblique view of the femoral pin guide assembly and femoral extension rod assembly of FIG. 1 from a different direction;

FIG. 26 is an exploded oblique view of the femoral four-in-one cut guide assembly of FIG. 22;

FIG. 27 is another exploded oblique view of the femoral four-in-one cut guide assembly of FIG. 22 from a different direction;

FIG. 28 is a front view of the femoral four-in-one cut guide assembly of FIG. 22 with a spacer;

FIG. 29 is a side view of the femoral four-in-one cut guide assembly and spacer of FIG. 28;

FIG. 30 is an oblique view of the femoral four-in-one cut guide assembly and spacer of FIG. 28;

FIG. 31 is an oblique view of the spacer of FIG. 28;

DETAILED DESCRIPTION

Figure 3:
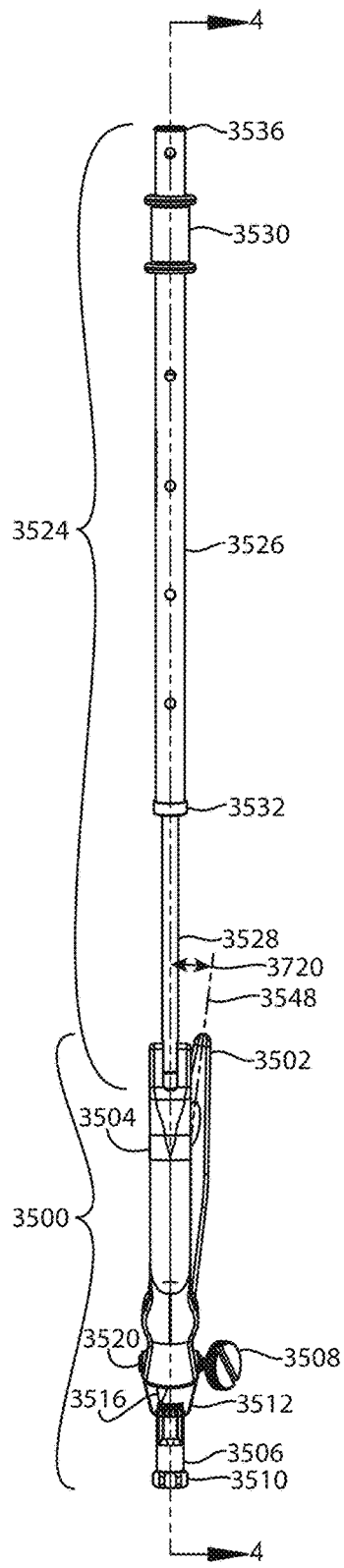
FIG. 3 is a top view of the femoral pin guide assembly and femoral extension rod assembly of FIG. 1.
Figure 4:
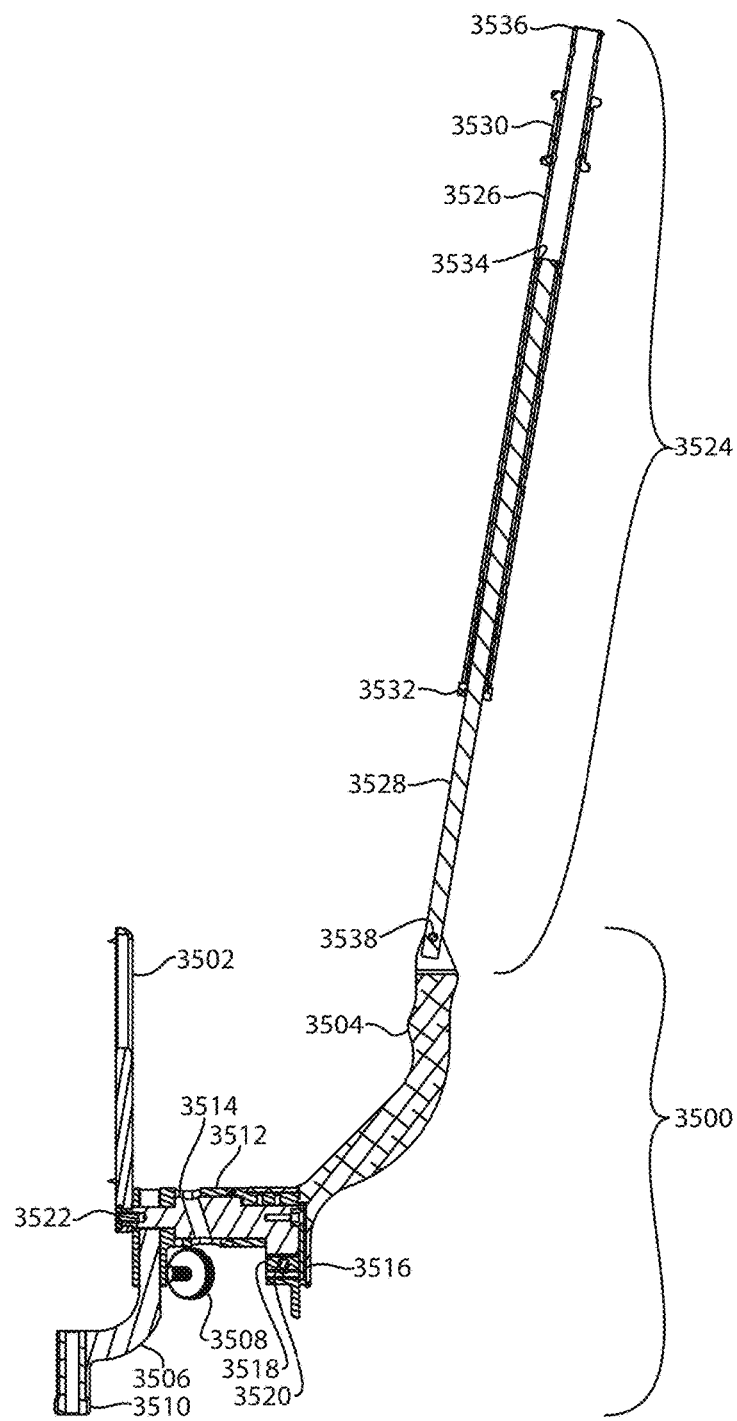
FIG. 4 is a cross-sectional view of the femoral pin guide assembly and femoral extension rod assembly of FIG. 1, taken along section line 4-4 of FIG. 3.
Figure 5:
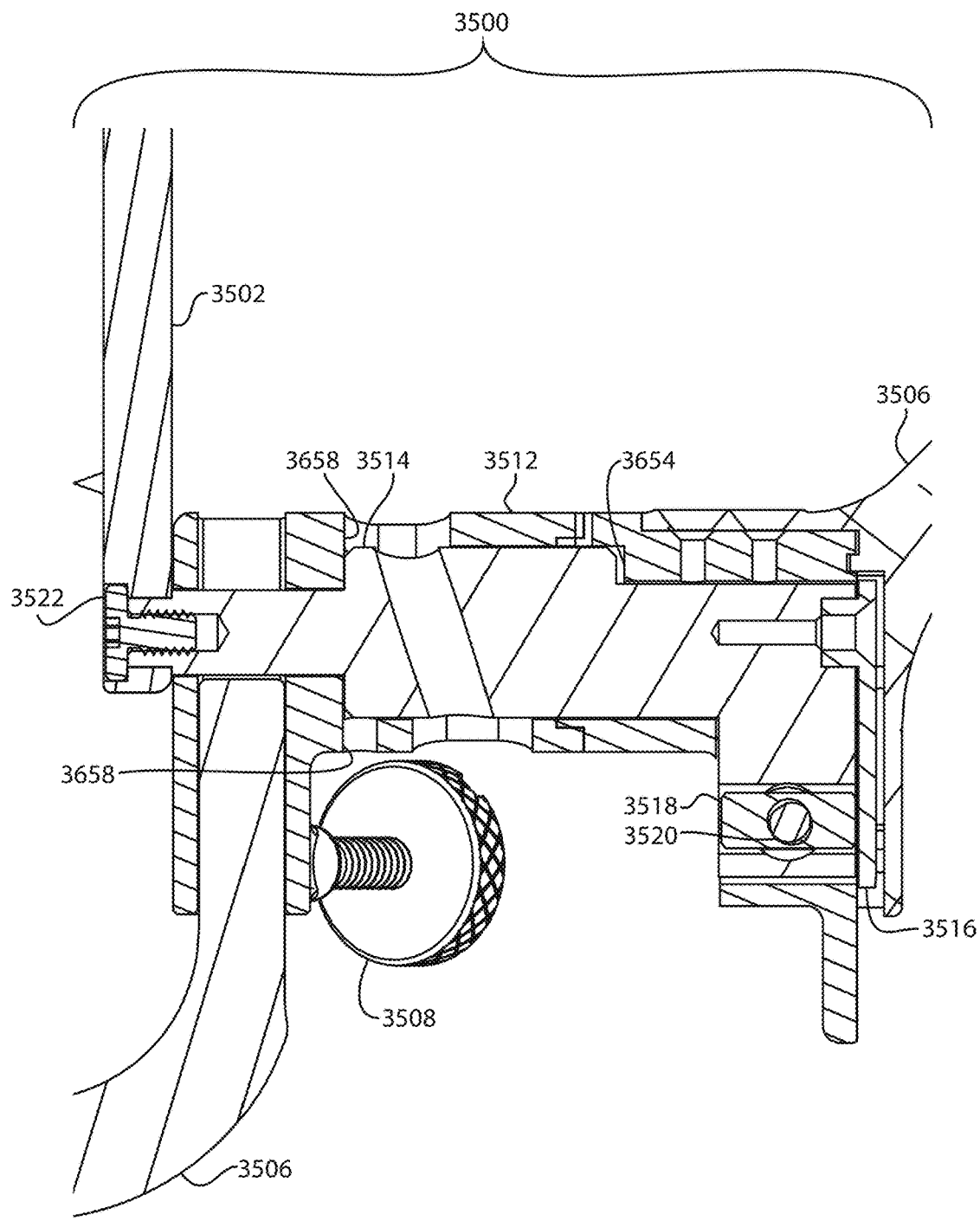
FIG. 5 is a cross-sectional detail view of a portion of the femoral pin guide assembly of FIG. 4.
Figure 6:
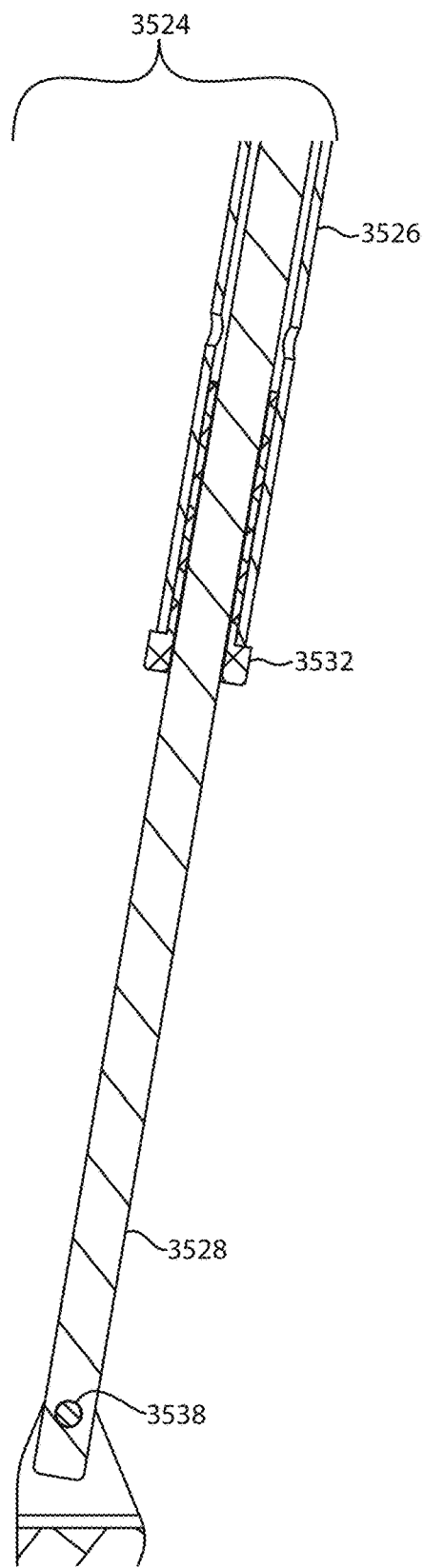
FIG. 6 is a cross-sectional detail view of a distal portion of the femoral extension rod assembly of FIG. 4.
Figure 7:
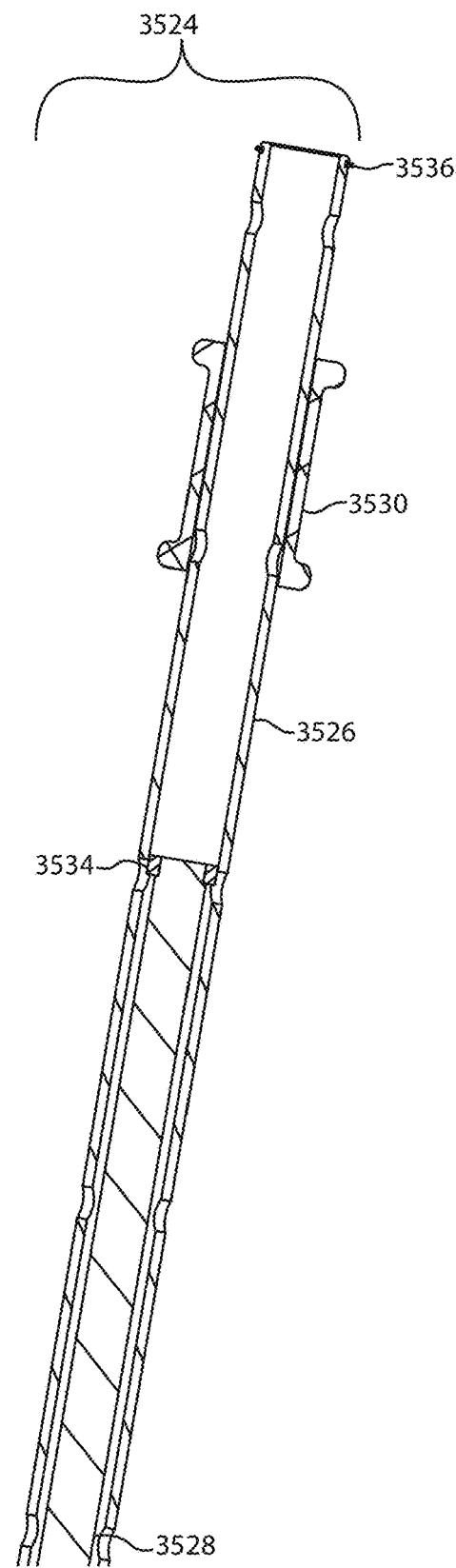
FIG. 7 is a cross-sectional detail view of a proximal portion of the femoral extension rod assembly of FIG. 4.
Figure 8:
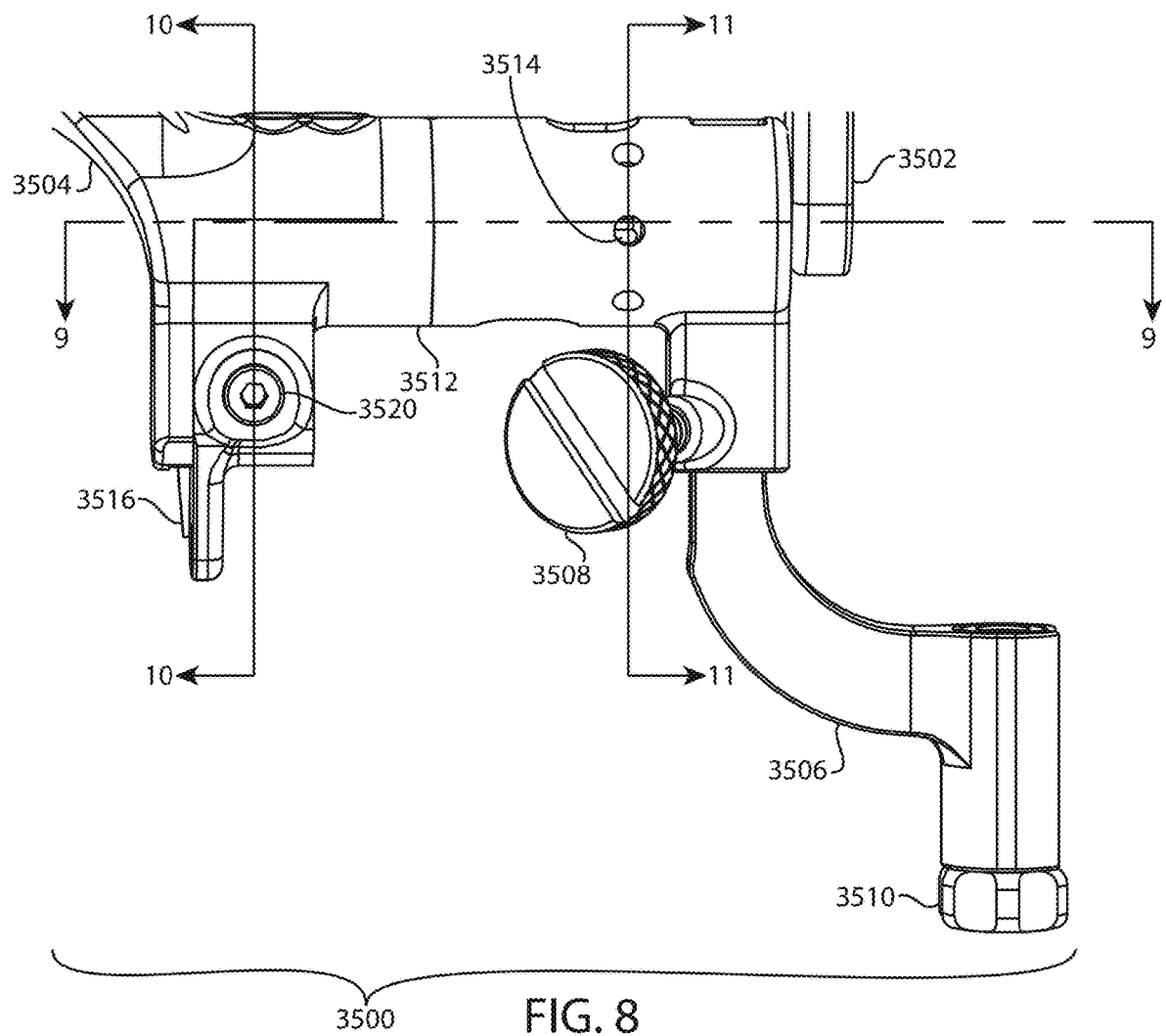
FIG. 8 is a side detail view of a portion of the femoral pin guide assembly of FIG. 1.
Figure 9:
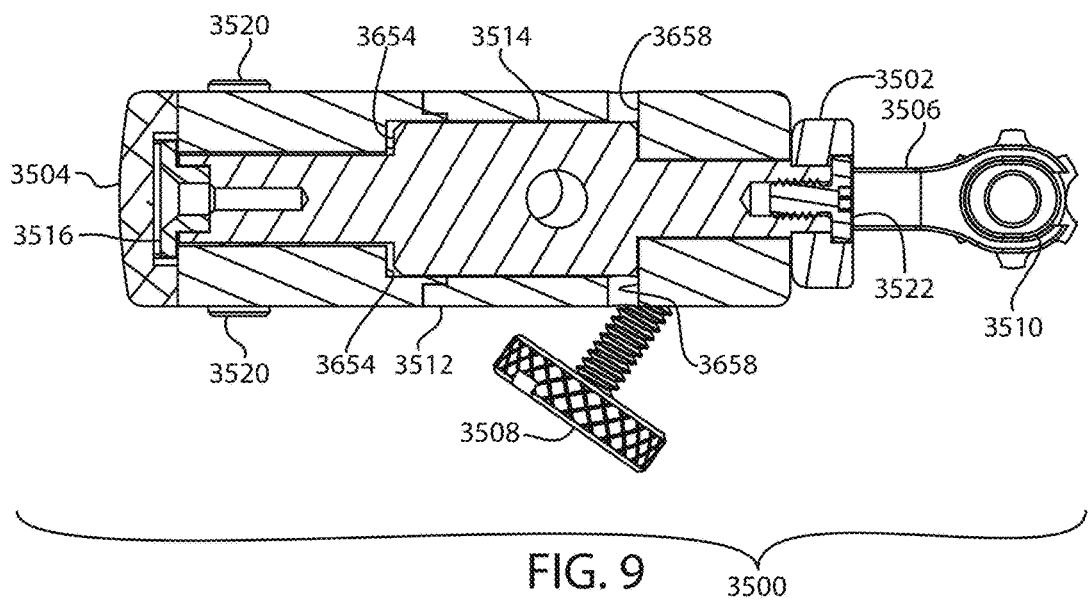
FIG. 9 is a cross-sectional view of the femoral pin guide assembly of FIG. 1, taken along section line 9-9 of FIG. 8.
Figures 10, 11:
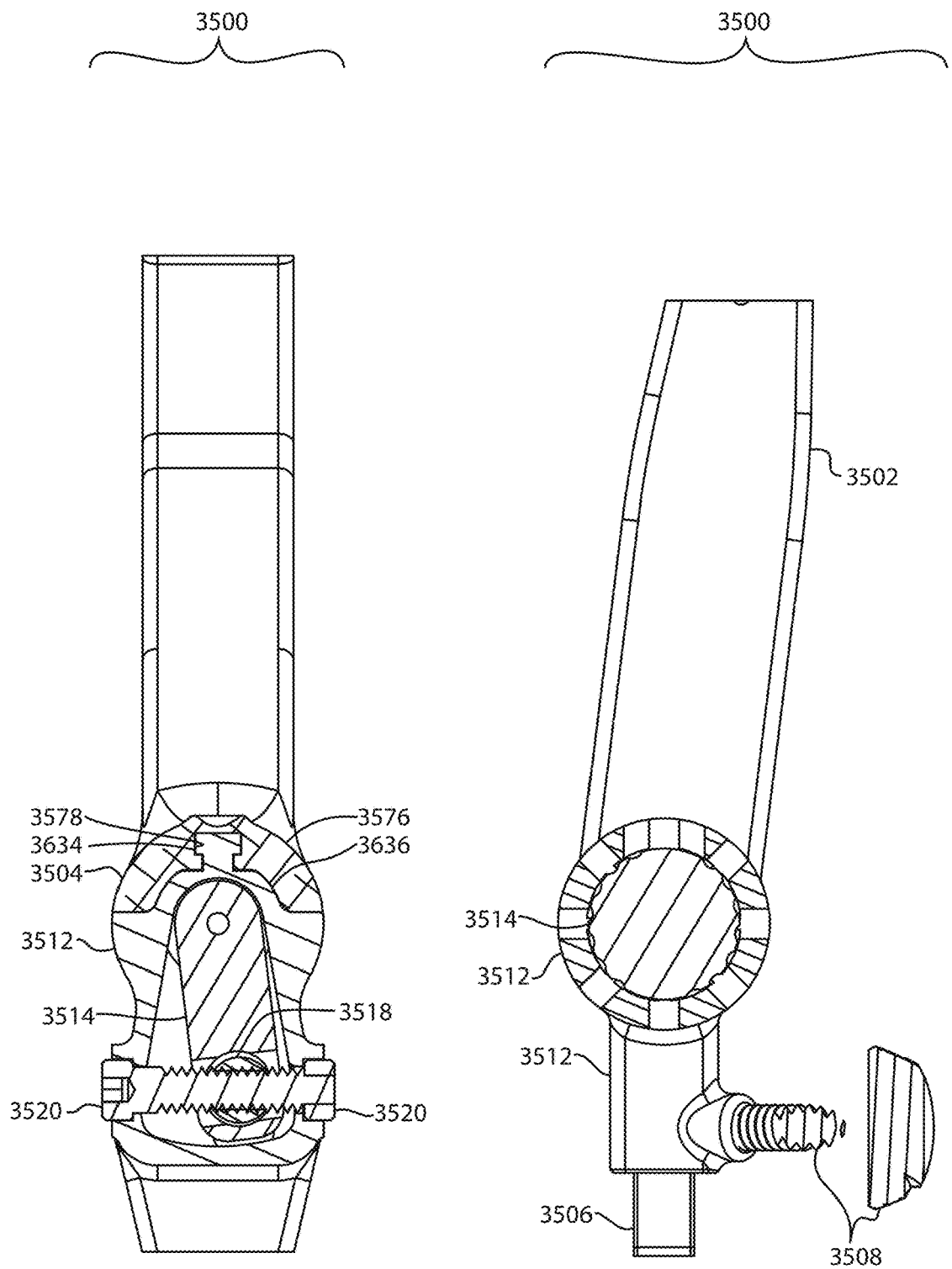
FIG. 10 is a cross-sectional detail view of a portion of the femoral pin guide assembly of FIG. 1, taken along section line 10-10 of FIG. 8.
FIG. 11 is a cross-sectional detail view of a portion of the femoral pin guide assembly of FIG. 1, taken along section line 11-11 of FIG. 8.
Figure 12:
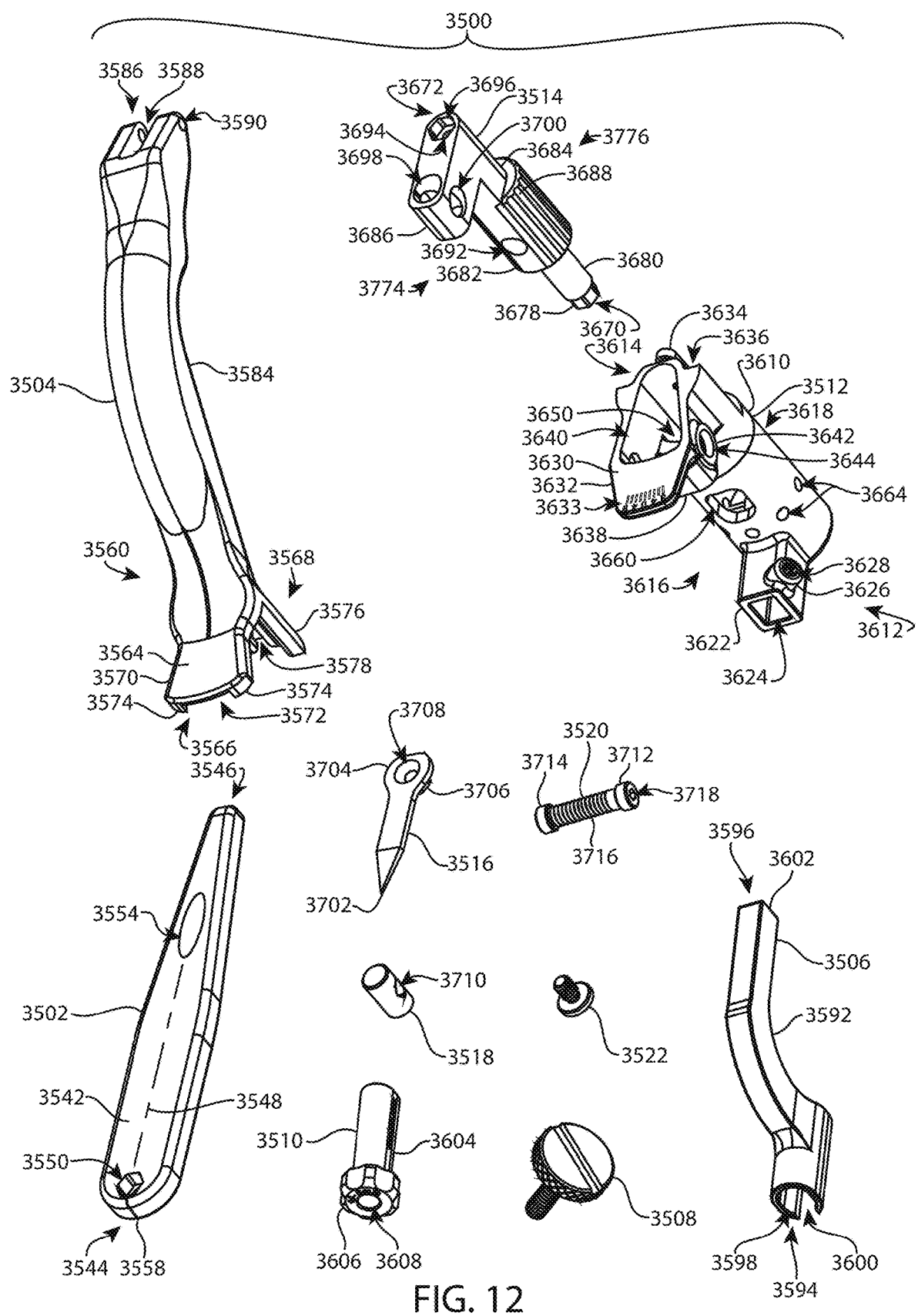
FIG. 12 is an oblique exploded view of the femoral pin guide assembly of FIG. 1.
Figure 13:
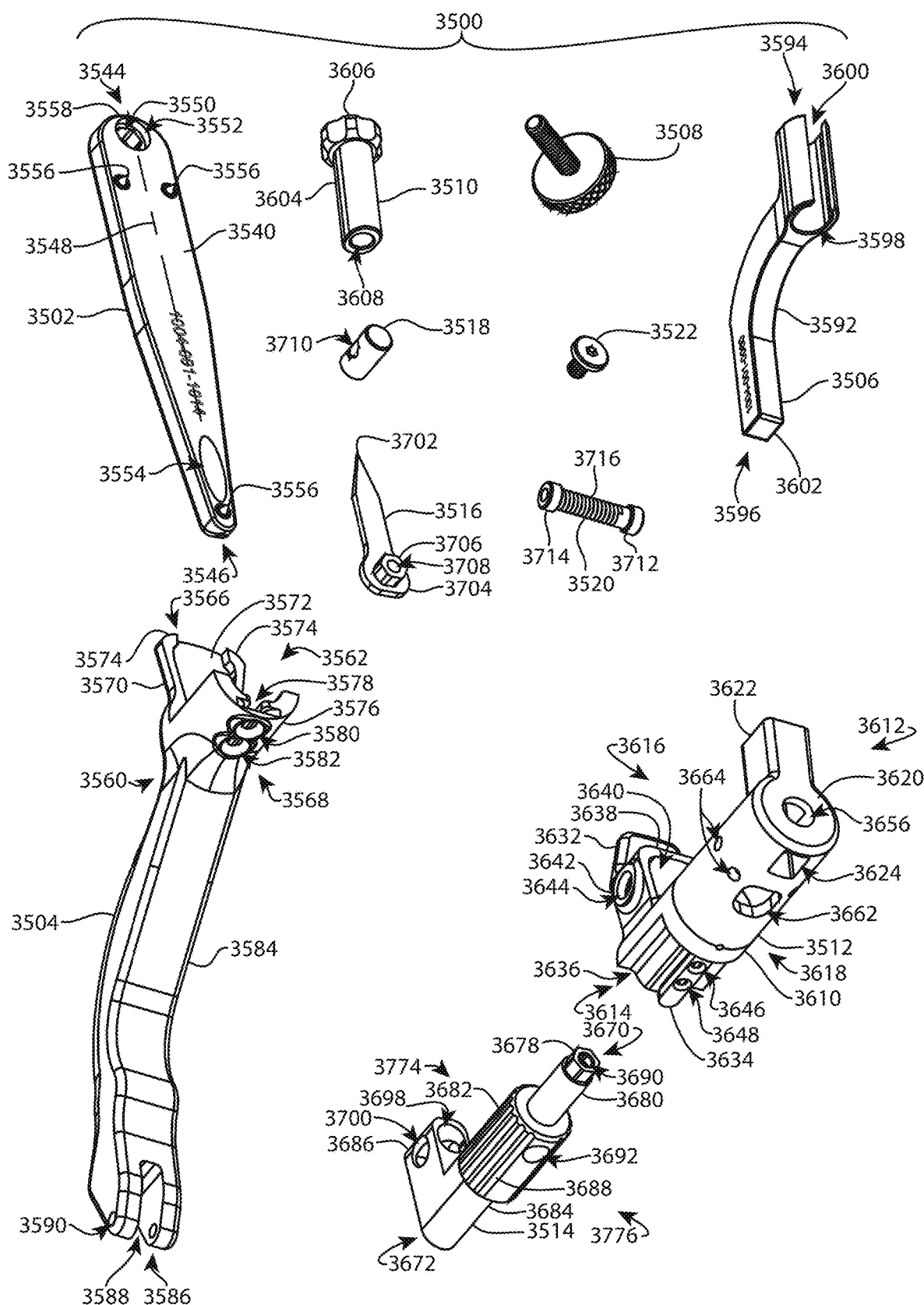
FIG. 13 is another oblique exploded view of the femoral pin guide assembly of FIG. 1 from a different direction.
Figure 14:
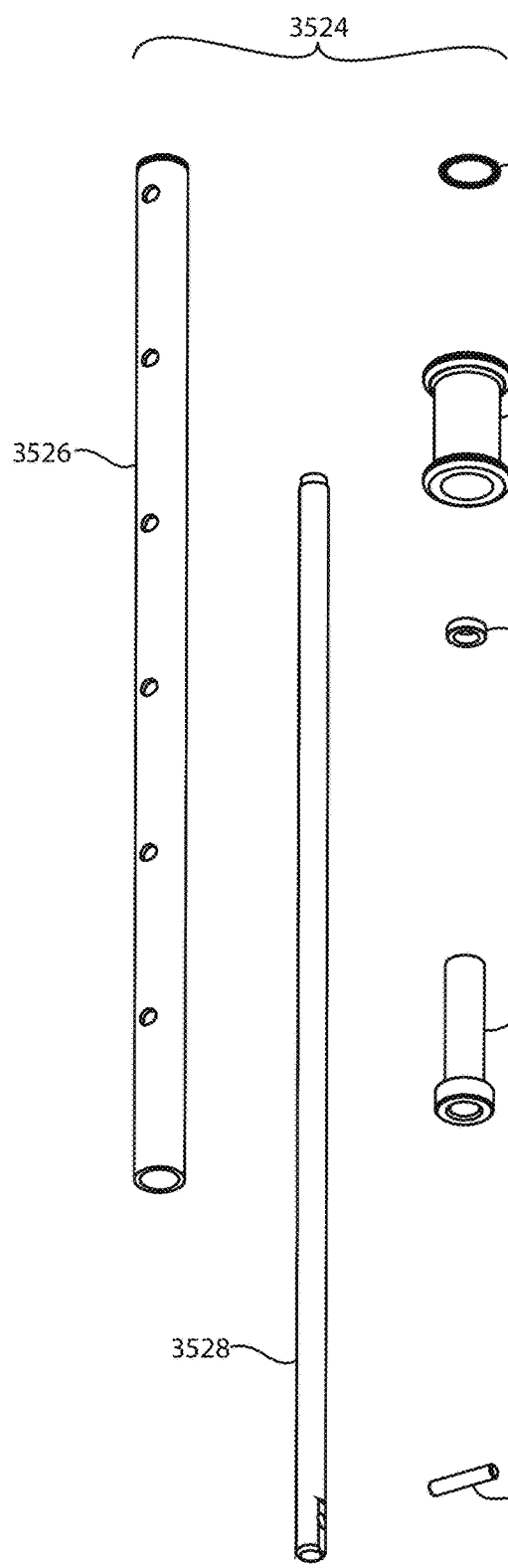
FIG. 14 is an oblique exploded view of the femoral extension rod assembly of FIG. 1.
Figure 15:
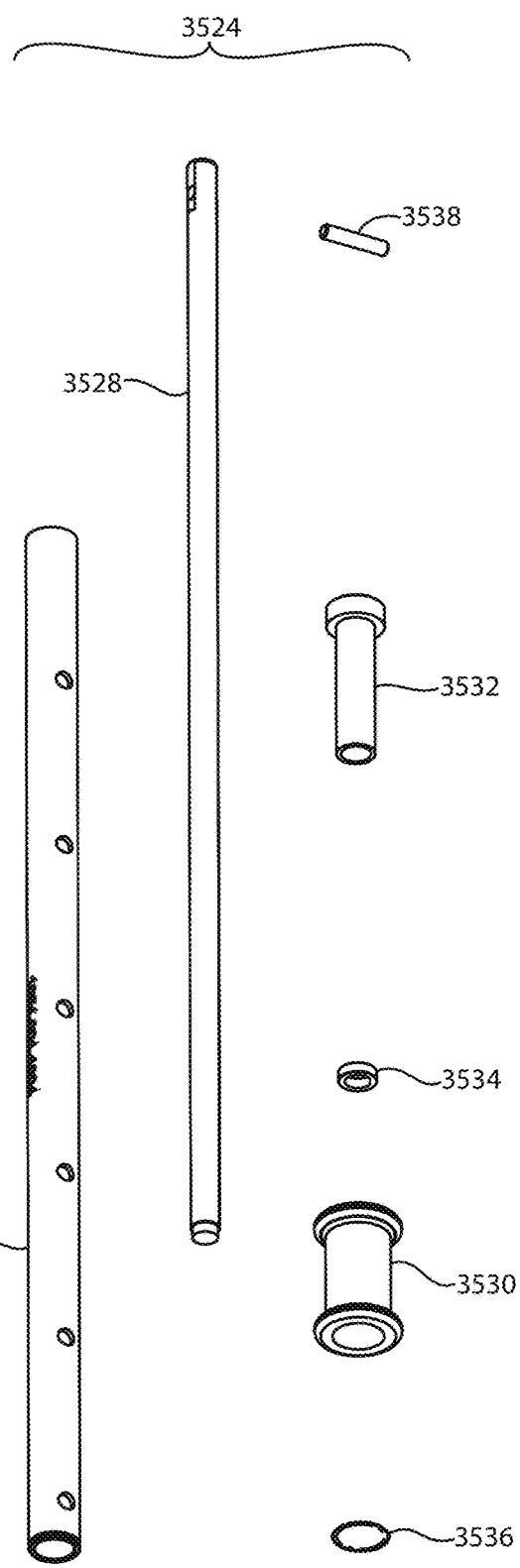
FIG. 15 is another oblique exploded view of the femoral extension rod assembly of FIG. 1 from a different direction.
Figure 16:
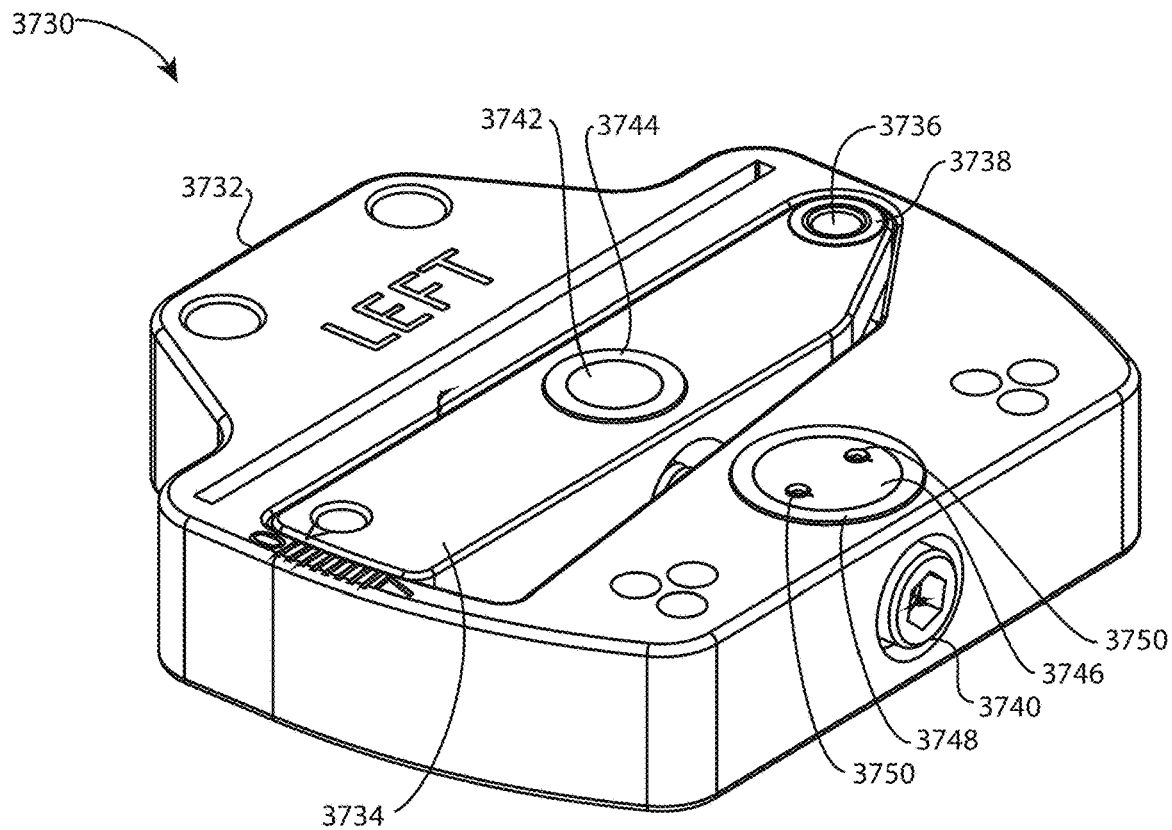
FIG. 16 is an oblique view of a distal femoral cut guide.
Figure 17:
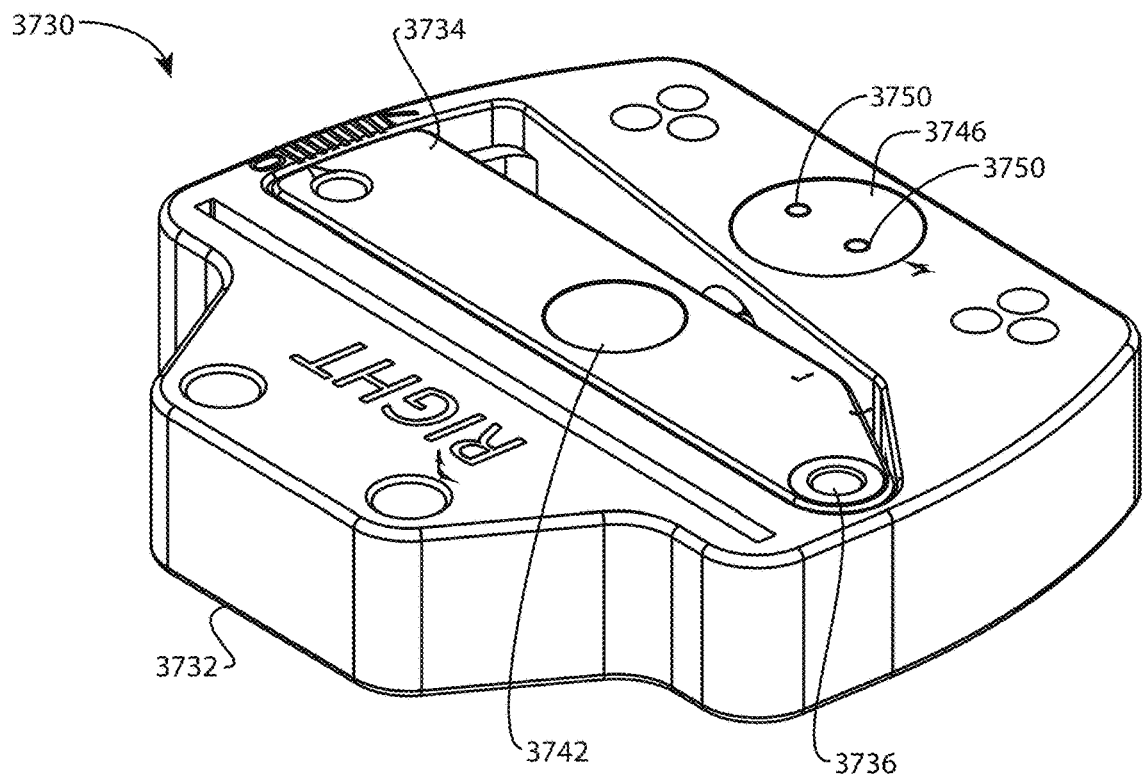
FIG. 17 is another oblique view of the distal femoral cut guide of FIG. 16 from a different direction.
Figure 18:
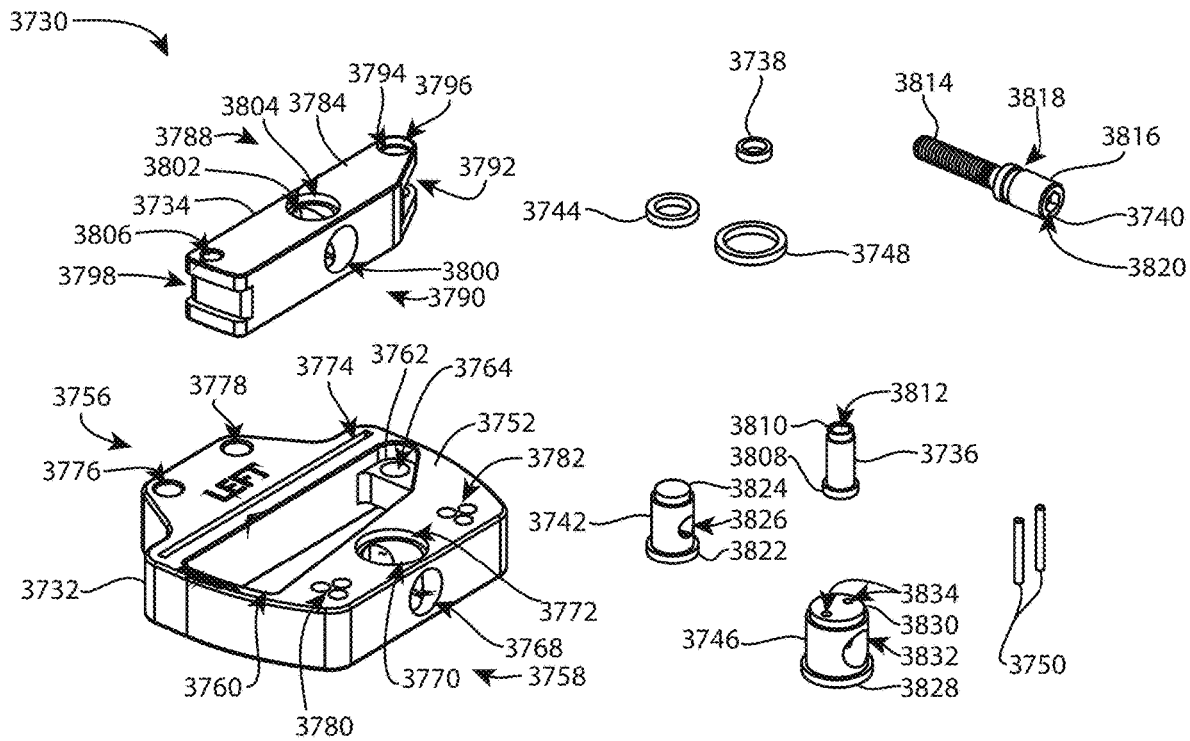
FIG. 18 is an exploded oblique view of the distal femoral cut guide of FIG. 16.
Figure 19:
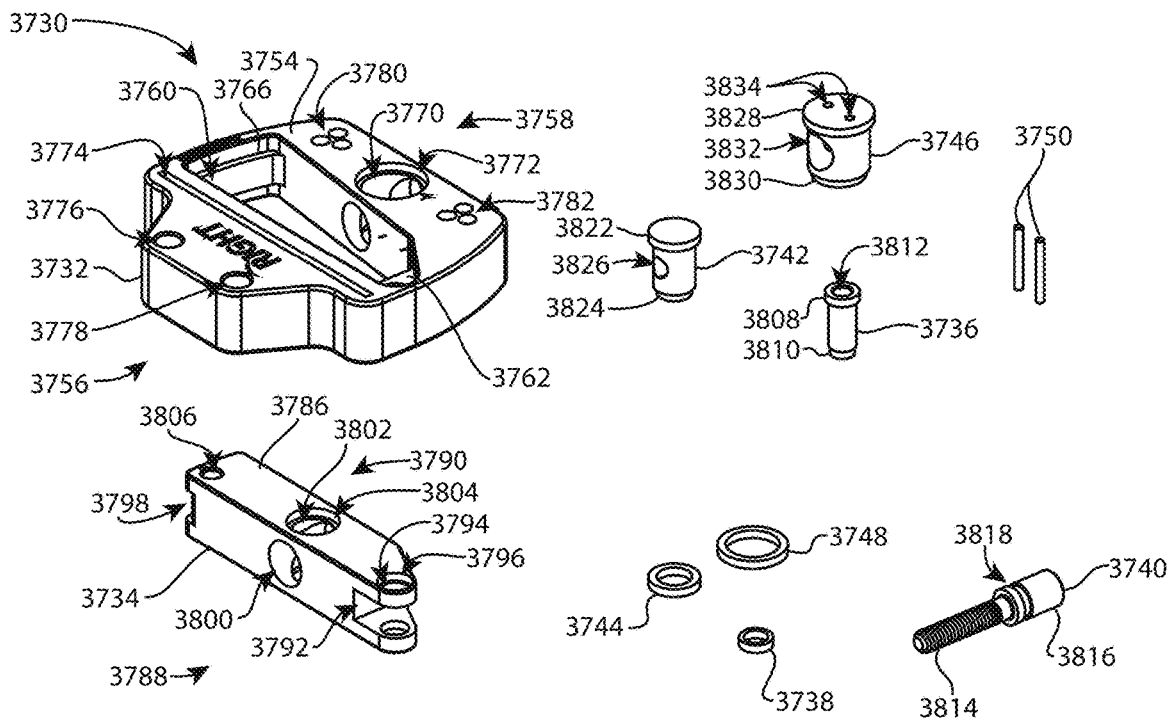
FIG. 19 is another exploded oblique view of the distal femoral cut guide of FIG. 16 from a different direction.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot.

Standard terminology related to knee arthroplasty is employed in this specification with the ordinary and customary meanings. Varus means deviation of the distal part of the leg below the knee inward, resulting in a bowlegged appearance. Valgus means deviation of the distal part of the leg below the knee outward, resulting in a knock-kneed appearance.

Referring to FIGS. 1-15, a femoral pin guide assembly 3500 may include a base 3502, a handle 3504, a pin guide 3506, a thumbscrew 3508, and a pin sleeve 3510. The femoral pin guide assembly may also include a housing 3512, a shaft 3514, a pointer 3516, a screw pin 3518, an adjuster screw 3520, and a foot screw 3522.

The base 3502 is an elongated plate with a bone contacting surface 3540 and an opposite top surface 3542. The base 3502 has a distal portion 3544 and a proximal portion 3546 which tapers to a proximal tip which is narrower than the distal portion. A longitudinal axis 3548 extends along the length of the base 3502 between the distal and proximal portions 3544, 3546; only a portion of the axis 3548 is shown for clarity. The base 3502 includes a through hole 3550 through the distal portion 3544 between the bone contacting surface 3540 and the top surface 3542. The hole 3550 in this example has a non-circular cross-sectional shape, illustrated as a hexagon. A pocket 3552 is recessed into the bone contacting surface 3540 around the hole 3550. The pocket 3552 may be described as a counterbore around the hole 3550. The base 3502 includes a through hole 3554 through the proximal portion 3546 between the bone contacting surface 3540 and the top surface 3542. The hole 3554 in this example extends obliquely through the base 3502 from a proximal location at the bone contacting surface 3540 to a distal location at the top surface 3542. The base 3502 may include one or more frictional elements, such as spikes 3556 protruding from the bone contacting surface 3540. The spikes 3556 in this example are integral with the base 3502, but in other examples the spikes may be separate set screws with sharp leading tips inserted into corresponding holes in the base 3502. The bone contacting surface 3540 includes a distal edge 3558.

The handle 3504 includes a base portion 3560 with a bone facing side 3562 and an opposite top side 3564. The base portion 3562 has a distal portion 3566 and a proximal portion 3568. The distal portion 3566 includes a generally flat, distally-extending plate 3570 that becomes wider in the medial-lateral direction as it extends distally. A pocket 3572 is formed in the bone facing side of the distal portion 3566. The pocket 3572 generally follows the outer profile of the distal portion 3566. Side walls 3574 extend distally along each side of the pocket 3572. The pocket 3572 may extend through the distal aspect of the distal portion 3566 between the side walls 3574. The proximal portion 3568 includes a generally arcuate, posterior-extending wall 3576. The wall 3576 may extend perpendicular to the plate 3570. A T-slot 3578 is formed in the distal side of the wall 3576 and extends in the anterior-posterior direction. The T-slot 3578 may extend through the posterior aspect of the proximal portion 3568. Two holes 3580, 3582 are shown extending through the wall 3576 and the T-slot in a proximal-distal direction. A stalk 3584 protrudes from the top side 3564 of the base portion 3562 between the distal and proximal portions 3566, 3568. The stalk 3584 terminates in a proximal free end 3586 with a slot 3588 and a through hole 3590. The slot 3588 may extend through the free end 3586 in the anterior-posterior direction. The through hole 3590 may extend through the free end 3586 in the medial-lateral direction, and may extend across the slot 3588.

The pin guide 3506 has a generally arcuate body 3592 that extends between a distal portion 3594 and a proximal portion 3596. The distal portion 3594 includes a longitudinal hole 3598 with a longitudinal slot 3600. The hole 3598 and slot 3600 extend in the distal-proximal direction. The hole 3598 in this example has a non-circular cross-sectional shape, such as the oval shape shown. The cross-sectional shape of the hole 3598 is elongated along the anterior-posterior direction. The proximal portion 3596 terminates in a free end 3602 which is illustrated with a non-circular cross-sectional shape. A rectangular cross-sectional shape is shown.

The pin sleeve 3510 includes a shaft 3604 with an enlarged head 3606 at one end and a longitudinal through hole 3608. The shaft 3604 in this example has a non-circular cross-sectional shape that is complementary to the hole 3598 of the pin guide 3506, such as the oval shaft 3604 shown. The complementary oval cross-sectional shapes enable the hole 3598 to receive the shaft 3604 in two orientations, 180 degrees apart. The hole 3608 may be centered in the cross-sectional shape of the shaft 3604 as shown, or the hole 3608 may be offset from the center. Preferably, the hole 3608 may be offset along the major axis of the oval cross-sectional shape. In this arrangement, when the shaft 3604 is inserted into the hole 3598 in one orientation, the hole 3608 is offset anteriorly, and when the shaft 3604 is inserted into the hole 3598 in the second orientation, the hole 3608 is offset posteriorly. This arrangement enables the user (surgeon) to adjust the location of the hole 3608 anterior or posterior to the nominal location (at the center of the cross-sectional shape of the shaft 3604), which ultimately adjusts the location of the anterior femoral resection anterior or posterior to the nominal location. A set of pin sleeves may be provided, each with the hole 3608 in a different location relative to the nominal location centered in the cross-sectional shape of the shaft 3604.

The housing 3512 includes a generally cylindrical body 3610 that extends between a posterior end 3612, or bone facing end, and an anterior end 3614. The body 3610 has a distal side 3616 and a proximal side 3618. The body 3610 may be fabricated as a single component part, and will be described this way. Optionally, the body may be fabricated as multiple component parts which are coupled together.

The posterior end 3612 of the housing 3512 couples to the base 3502, pin guide 3506, and thumbscrew 3508. The posterior end 3612 may terminate in a posterior surface 3620. The surface 3620 may be planar, and may extend perpendicular to a central longitudinal axis of the cylindrical body 3610. A first boss 3622 may extend from the distal side 3616 of the posterior end 3612. The boss 3622 surrounds a socket 3624 with a non-circular cross-sectional shape that is complementary to the free end 3602 of the pin guide 3506. A rectangular cross-sectional shape is shown. The socket 3624 may extend through the housing 3512 in a proximal-distal direction. A second boss 3626 may extend outwardly transversely or perpendicularly from the first boss 3622. The boss 3626 surrounds an internally threaded socket 3628 that is complementary to external threads of the thumbscrew 3508. The socket 3628 intersects the socket 3624.

The anterior end 3614 of the housing 3512 couples to the handle 3504. The anterior end 3614 may terminate in an anterior surface 3630. The surface 3630 may be planar, and may extend perpendicular to a central longitudinal axis of the cylindrical body 3610. A plate 3632 may extend from the distal side 3616 of the anterior end 3614 and may share the surface 3630. Indicia 3633 may be provided on the surface 3630. Indicia 3633 are shown in the distal region of surface 3630 where it extends along the plate 3632. A T-rail 3634 is formed in the proximal side 3618 of the anterior end 3614 and extends in the anterior-posterior direction. The T-rail is complementary to the T-slot 3578 of the handle 3504. A recess 3636 may extend around the T-rail 3634, and may be complementary to the wall 3576 of the handle 3504. See FIG. 10. Two holes 3646, 3648 are shown extending through the T-rail 3634 in a proximal-distal direction. A wall 3638 may extend posteriorly from the posterior side of the plate 3632 on the distal side 3616 of the anterior end 3614. The wall 3638 may loop outwardly from the body 3610 to encircle a generally wedge-shaped pocket 3640 that extends posteriorly through the anterior surface 3630 into the housing 3512. Short bilateral bosses 3642 may protrude from the wall 3638 along the medial-lateral direction. A hole 3644 may extend through the housing 3512 through the bosses 3642; each end of the hole 3644 may include a counterbore.

The pocket 3640 may be one of a series of four cavities or hole segments arranged along the anterior-posterior length of the housing 3512. Posterior to the pocket 3640, a non-circular hole segment 3650 may extend from the posterior end of the wall 3638 to a location just posterior to the T-rail 3634 and/or recess 3636. The proximal profile of the hole segment 3650 may match the proximal profile of the pocket 3640 and hole segment 3650 may have a circular distal profile. Posterior to the hole segment 3650, a circular hole segment 3652 may extend to a location just anterior to the boss 3622. The hole segment 3652 may be concentric with the circular distal profile of the hole segment 3650. An undercut or shoulder 3654 may be formed at the intersection of the hole segments 3650, 3652, around the proximal profile. See FIGS. 5 and 9. Posterior to the hole segment 3652, another circular hole segment 3656 may extend through the posterior surface 3620. The hole segments 3652, 3656 may be concentric, and hole segment 3656 may have a smaller inside diameter than hole segment 3652. An undercut or shoulder 3658 may be formed all around at the intersection of the hole segments 3652, 3656. See FIGS. 5 and 9.

A distal window 3660 extends through the distal side 3616 of the housing 3512 to intersect the hole segment 3652. A proximal window 3662 extends through the proximal side 3618 of the housing 3512 to intersect the hole segment 3652. The proximal window 3662 may be posterior to the distal window 3660. The posterior end of the proximal window 3662 may be at the same level as the shoulder 3658. A circular array of holes 3664 extend through the housing at a level between the boss 3622 and the distal window 3660.

The shaft 3514 is a generally L-shaped part that extends between a posterior end 3670, or bone facing end, and an anterior end 3772. The shaft 3514 has a distal side 3774 and a proximal side 3776. The shaft 3514 may include five segments 3678, 3680, 3682, 3684, 3686 along its length between the posterior end 3670 and the anterior end 3772.

The posterior end 3670 terminates with the first segment 3678, which may have a non-circular external cross-sectional shape for torque transmission, such as the hexagonal shape shown. The second segment 3680 may have a circular external cross-sectional shape with an outer diameter that is the same as, or greater than, the major dimension across the first segment 3678. The third segment 3682 may have a circular external cross-sectional shape with an outer diameter that is greater than the outer diameter of the second segment 3680. The first, second, and third segments may be concentric. The third segment 3682 may include a circular array of longitudinal grooves 3688. The grooves 3688 may be present around the left, proximal 3776, and right sides, and absent from the distal side 3774 as shown. The fourth segment 3684 may have an overall non-circular external cross-sectional shape with flat left and right sides, however the cross-sectional shape may include a distal circular portion and a proximal circular portion with a smaller radius than the distal circular portion. The distal and proximal circular portions may be concentric with each other and with the first, second, and third segments 3678, 3680, 3682. The radius of the distal circular portion may be the same as the radius of the third segment 3682. The anterior end 3772 terminates with the fifth segment 3686, which may have an overall non-circular external cross-sectional shape with flat left and right sides, however the cross-sectional shape may include a proximal circular portion that may be concentric with the first, second, and third segments 3678, 3680, 3682 as well as the distal and proximal circular portions of the fourth segment 3684. The fifth segment 3686 may be elongated in the distal direction so as to extend distally past the outer diameter of the third segment to form the lower transverse element of the L-shape.

A threaded hole 3690 may extend longitudinally into the posterior end 3670, through the first segment 3678, and into the second segment 3680. The hole 3690 is complementary to external threads of the foot screw 3522. A hole 3692 may through the third segment 3682 between the distal and proximal sides 3774, 3776 along an oblique distal-anterior to proximal-posterior direction. A threaded hole 3694 may extend longitudinally into the anterior end 3772 and the fifth segment 3686. The hole 3694 may include a non-circular counterbore 3696 for torque transmission, such as the hex socket shown. A hole 3698 may extend through the distal free end of the fifth segment 3686 along the anterior-posterior direction. The hole 3698 may be oval as shown, elongated along the proximal-distal direction. A hole 3700 may extend through the distal free end of the fifth segment 3686 along the left-right direction. The holes 3698, 3700 may intersect each other.

The pointer 3516 may be an elongated plate or sheet metal part with a pointed distal tip 3702 and an opposite head 3704. The head 3704 may be wider than the rest of the pointer 3516. A boss 3706 extends from the distal side of the head 3704. The boss 3706 may have a non-circular cross-sectional shape for torque transmission, such as the hex boss shown. The boss 3706 is complementary to the counterbore 3696 of the shaft 3514. A hole 3708 may extend through the head 3704 and boss 3706 along the proximal-distal direction, and may include a proximal countersink.

The screw pin 3518 may be a cylindrical part with a centrally located internally threaded transverse through hole 3710. The outer diameter of the screw pin 3518 is complementary to the hole 3698 of the shaft 3514.

The adjuster screw 3520 may be an elongated generally cylindrical part with enlarged heads 3712, 3714 at each end and a threaded shaft 3716 between the heads. At least one head 3712, 3714 includes a torque fitting 3718 such as the hex socket shown. The adjuster screw 3520 may be fabricated as a single component part. Optionally, the adjuster screw 3520 may be fabricated as multiple component parts which are coupled together, for example a conventional screw with a separate nut equivalent to head 3714. The threaded shaft 3716 is complementary to the hole 3700 of the shaft 3514 and the threaded hole 3710 of the screw pin 3518.

The femoral pin guide assembly 3500 may be assembled by performing the following steps. These steps may be performed in any order.

Inserting the shaft 3514 into the housing 3512 so that the first segment 3678 protrudes through the posterior surface 3620, the second segment 3680 is received in the hole segment 3656, and the fifth segment 3686 is received in the pocket 3640.

Inserting the screw pin 3518 into the hole 3698 of the shaft 3514 so that the hole 3710 is aligned with the hole 3700.

Inserting the adjuster screw 3520 through the hole 3644 of the housing 3512, the hole 3700 of the shaft 3514, and threading the shaft 3716 into the hole 3710 of the screw pin 3518 so that the heads 3712, 3714 are received in the counterbores of the hole 3644. Preferably, the adjuster screw 3520 is made in two parts, a conventional screw and a separate nut, for ease of assembly.

Inserting the boss 3706 of the pointer 3516 into the counterbore 3696 of the shaft 3514 so that when the fifth segment 3686 is against the left or right side of the pocket 3640, the distal tip 3702 aligns with the corresponding mark of the indicia 3633, and when the fifth segment 3686 is centered left-right in the pocket 3640, the distal tip 3702 aligns with the zero mark of the indicia 3633. A fastener (not shown) may be inserted through the hole 3708 of the pointer 3516 and threaded into the hole 3694 of the shaft 3514 to secure the pointer to the shaft.

Sliding the T-rail 3634 of the housing 3512 into the T-slot 3578 of the handle 3504 so that the recess 3636 receives the wall 3576. Fasteners (not shown) may be inserted through the holes 3580, 3582 and threaded into the holes 3646, 3648 to secure the handle 3504 to the housing 3512.

Inserting the first segment 3678 of the shaft 3514 into the hole 3550 of the base 3502 so that the top surface 3542 faces the posterior surface 3620 of the housing 3512 and the base 3502 and pointer 3516 are in line with each other.

Inserting the foot screw 3522 through the hole 3550 of the base 3502 and into the threaded hole 3690 of the shaft 3514 to secure the base 3502 to the shaft 3514.

Inserting the shaft 3604 of the pin sleeve 3510 into the hole 3598 of the pin guide 3506 so that the head 3606 extends distally from the distal portion 3594 and the hole 3608 is in the desired location (anterior or posterior to the nominal location).

Inserting the free end 3602 of the pin guide 3506 into the socket 3624 of the housing 3512 so that the distal portion 3594 extends distally and posteriorly from the housing 3512.

Threading the thumbscrew 3508 into the threaded socket 3628 of the housing 3512 and into contact with the free end 3602 of the pin guide 3506 to releasably secure the pin guide 3506 to the housing 3512.

When the femoral pin guide assembly 3500 is operatively assembled, rotating the adjuster screw 3520 causes the screw pin 3518 to translate left-right along the adjuster screw 3520 within the pocket 3640 of the housing 3512. This causes the shaft 3514, with the attached pointer 3516 and base 3502, to move along with the screw pin 3518 relative to the housing 3512. The pin guide 3506 may be coupled to the housing 3512 by performing the last two steps above, and uncoupled from the housing by reversing those steps. The pin sleeve 3510 may be removed from the pin guide 3506, reoriented if desired, and reinserted.

The femoral pin guide assembly 3500 may be coupled to, or may include, a femoral extension rod assembly 3524 which may include an outer rod 3526, an inner rod 3528, a spool 3530, a sleeve 3532, a ring 3534, a retaining ring 3536, and a pin 3538. The femoral extension rod assembly 3524 may be the same as, or similar to, the femoral extension rod assembly 506, 1506, and/or 2506 of U.S. patent application Ser. No. 15/630,555.

The femoral extension rod assembly 3524 may be assembled by performing the assembly steps described for the femoral extension rod assembly 506, 1506, and/or 2506 of U.S. patent application Ser. No. 15/630,555.

When the femoral extension rod assembly 3524 is operatively assembled, the inner rod 3528 with attached ring 3534 telescopes inside the outer rod 3526 with attached sleeve 3532 and retaining ring 3536. The spool 3530 is free to slide along the outer rod 3526 between the sleeve 3532 and the retaining ring 3536.

The femoral pin guide assembly 3500 and the femoral extension rod assembly 3524 may be assembled by inserting the end of the inner rod 3528 with the hole (FIGS. 4, 6, 14, and 15) into the slot 3588 of the handle 3504, aligning the inner rod hole with the hole 3590, and inserting the pin 3538 through the holes to form a hinge.

Referring to FIG. 3, when the femoral pin guide assembly 3500 and the femoral extension rod assembly 3524 are operatively assembled, in a top view, an angle 3720 is formed between the longitudinal axis 3548 of the base 3502 and the central longitudinal axis of the femoral extension rod assembly 3524, represented by section line 4-4 of FIG. 3. In the current embodiment, the angle 3720 is variable by turning the adjuster screw 3520. This is advantageous because the angle between the mechanical axis of the leg (femoral extension rod assembly axis) and the anatomical shaft axis of the femur (base axis) is variable from one patient to the next. The angle 3720 may be adjusted so that when the femoral extension rod assembly axis is aligned with the mechanical axis of the leg, the base axis 3548 is simultaneously aligned with the femoral shaft axis. This ensures that the bone contacting surface 3540 (and/or a theoretical bone contacting plane established by the spikes 3556) of the base 3502 makes good contact with the distal anterior femoral cortical surface for the best possible alignment of the base relative to the femur.

Referring to FIGS. 16-21, an adjustable distal femoral cut guide assembly 3730 may include a body 3732, a slide 3734, a pivot pin 3736, a pivot pin collar 3738, a screw 3740, a screw pin 3742, a screw pin collar 3744, an adjuster pin 3746, an adjuster pin collar 3748, and a screw retainer pin 3750. Two screw retainer pins 3750 are shown.

The body 3732 is a flat plate part with opposite first and second bone-facing surfaces 3752, 3754, a distal side 3756, and a proximal side 3758. A generally wedge-shaped window 3760 extends through the body 732 between the bone-facing surfaces 3752, 3754. The window 3760 receives the slide 3734. A first shelf 3762 extends across the narrow end of the window 3760 along the proximal-distal direction and is recessed from each bone-facing surface 3752, 3754. A hole 3764 extends through the shelf 3762 in the same direction as the window 3760. The hole 3764 receives the pivot pin 3736. A second shelf 3766 extends across the wide end of the window 3760 along the proximal-distal direction and is recessed from each bone-facing surface 3752, 3754. The first and second shelves 3762, 3766 may be recessed identically. A hole 3768 extends into the proximal side 3758, approximately centered in the width of the body 3732, and intersects the window 3760. The hole 3768 receives the screw 3740. A hole 3770 extends through the body 3732 between the bone-facing surfaces 3752, 3754 and between the proximal side 3758 and the window 3760. The hole 3770 intersects the hole 3768. The hole 3770 receives the adjuster pin 3746. The hole 3770 may have counterbores 3772 at the first and second bone-facing surfaces 3752, 3754 to receive a head of the adjuster pin 3746 or the adjuster pin collar 3748. A saw slot 3774 and holes 3776, 3778 extend through the distal portion of the body 3732 between the bone-facing surfaces 3752, 3754, with the saw slot between the holes and the window 3760. Bilateral hole clusters 3780, 3782 extend through the proximal portion of the body 3732 between the bone-facing surfaces 3752, 3754, on either side of the hole 3770.

The slide 3734 is an elongated generally rectangular part with opposite first and second bone-facing surfaces 3784, 3786, a distal side 3788, and a proximal side 3790. A first slot 3792 extends across a tapered first end of the slide 3734 along the proximal-distal direction and is complementary to the first shelf 3762 of the body 3732. A hole 3794 extends through the slide 3734 between the first and second bone-facing surfaces 3784, 3786 and across the slot 3792. The hole 3794 receives the pivot pin 3736. The hole 3794 may have counterbores 3796 at the first and second bone-facing surfaces 3784, 3786 to receive a head of the pivot pin 3736 or the pivot pin collar 3738. A second slot 3798 extends across an opposite end of the slide 3734 along the proximal-distal direction and is complementary to the second shelf 3766 of the body 3732. A hole 3800 extends through the slide 3734 between the distal and proximal sides 3788, 3790, approximately centered in the length of the slide. The hole 3800 receives the screw 3740. A hole 3802 extends through the slide 3734 between the first and second bone-facing surfaces 3784, 3786. The hole 3802 intersects the hole 3800. The hole 3802 receives the screw pin 3742. The hole 3802 may have counterbores 3804 at the first and second bone-facing surfaces 3784, 3786 to receive a head of the screw pin 3742 or the screw pin collar 3744. A hole 3806 extends through the slide 3734 between the first and second bone-facing surfaces 3784, 3786 near the distal side 3788 and the second slot 3798.

The pivot pin 3736 is a cylindrical part with an enlarged head 3808 at one end, a reduced diameter section 3810 at the other end, and a longitudinal through hole 3812. The pivot pin collar 3738 is a ring that is complementary to the reduced diameter section 3810 of the pivot pin 3736.

The screw 3740 has an externally threaded distal shaft 3814 and an enlarged head 3816 opposite the shaft 3814. A groove 3818 encircles the head 3816 near the junction with the shaft 3814. The head 3816 includes a torque fitting 3820, such as the hex socket shown.

The screw pin 3742 is a cylindrical part with an enlarged head 3822 at one end, a reduced diameter section 3824 at the other end, and a central transverse internally threaded hole 3826. The hole 3826 receives the shaft 3814 of the screw 3740. The screw pin collar 3744 is a ring that is complementary to the reduced diameter section 3824 of the screw pin 3742.

The adjuster pin 3746 is a cylindrical part with an enlarged head 3828 at one end, a reduced diameter section 3830 at the other end, a central transverse hole 3832, and bilateral longitudinal holes 3834. The holes 3834 intersect the hole 3832. The adjuster pin collar 3748 is a ring that is complementary to the reduced diameter section 3830 of the adjuster pin 3746.

The adjustable distal femoral cut guide assembly may be assembled by performing the following steps. These steps may be performed in any order.

Inserting the slide 3734 into the window 3760 of the body 3732 so that the first shelf 3762 is received in the first slot 3792, the second shelf 3766 is received in the second slot 3798, and the distal sides 3756, 3788 face the same direction.

Inserting the pivot pin 3736 into the hole 3794 of the slide 3734 and the hole 3764 of the body 3732 so that the head 3808 is received in a counterbore 3796.

Coupling the pivot pin collar 3738 to the reduced diameter section 3810 of the pivot pin 3736 so that the pivot pin collar 3738 is received in the other counterbore 3796.

Inserting the screw pin 3742 into the hole 3802 of the slide 3734 so that the head 3822 is received in a counterbore 3804 and the hole 3826 is aligned with the hole 3800.

Coupling the screw pin collar 3744 to the reduced diameter section 3824 of the screw pin 3742 so that the screw pin collar 3744 is received in the other counterbore 3804.

Inserting the adjuster pin 3746 into the hole 3770 of the body 3732 so that the head 3828 is received in a counterbore 3772 and the hole 3832 is aligned with the hole 3768.

Coupling the adjuster pin collar 3748 to the reduced diameter section 3830 of the adjuster pin 3746 so that the adjuster pin collar 3748 is received in the other counterbore 3772.

Inserting the screw 3740 into the hole 3768 of the body 3732, the hole 3832 of the adjuster pin 3746, the hole 3800 of the slide 3734, and threading the shaft 3814 into the hole 3826 of the screw pin 3742.

Inserting the screw retainer pins 3750 into the holes 3834 of the adjuster pin 3746 and the groove 3818 of the screw 3740 to make the screw captive to the body 3732.

Figure 20:
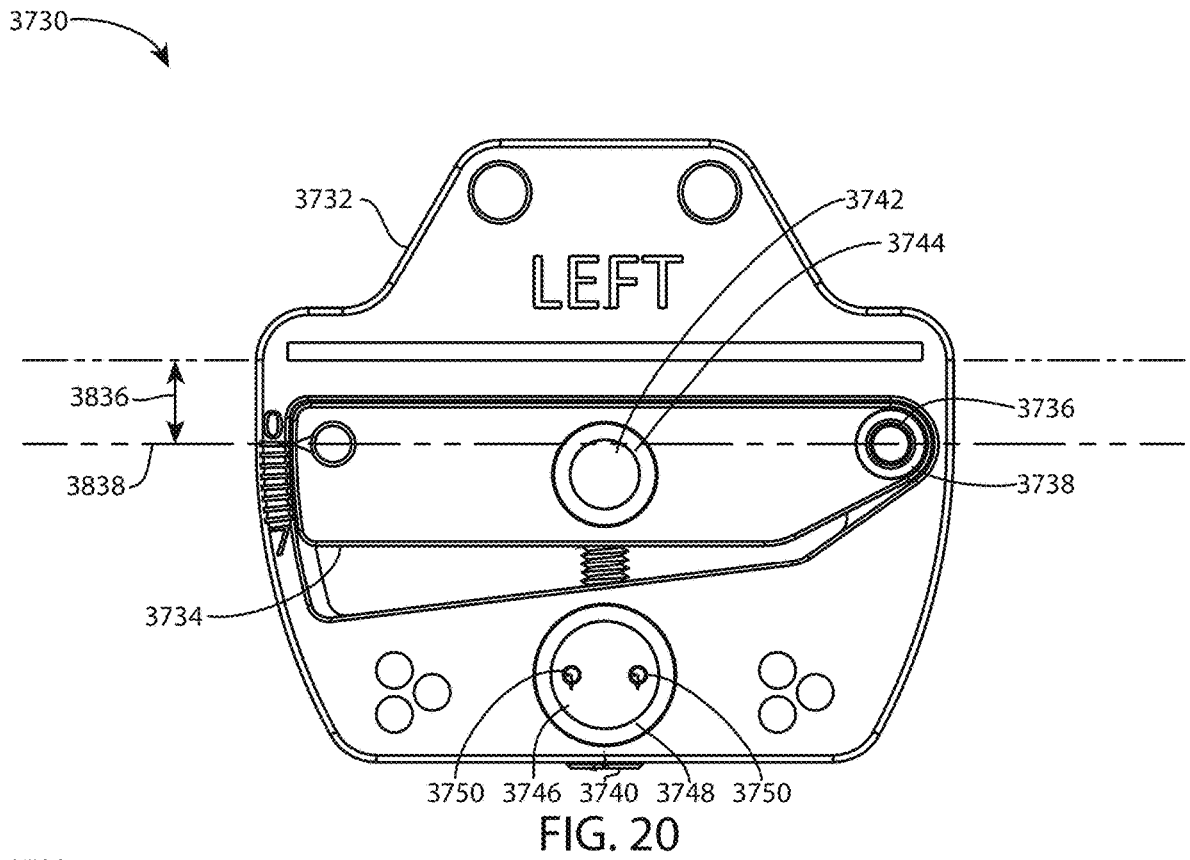
FIG. 20 is a top view of the distal femoral cut guide of FIG. 16 set to zero degrees.
Figure 21:
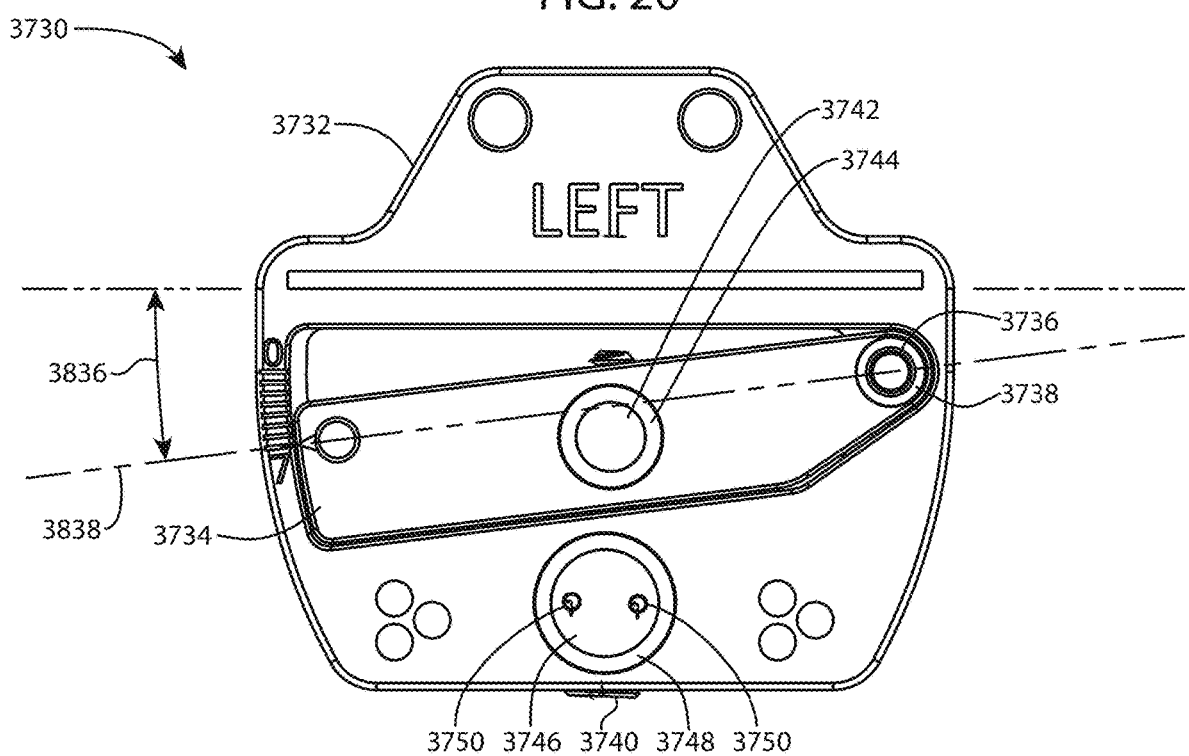
FIG. 21 is a top view of the distal femoral cut guide of FIG. 16 set to seven degrees.
Figure 22:
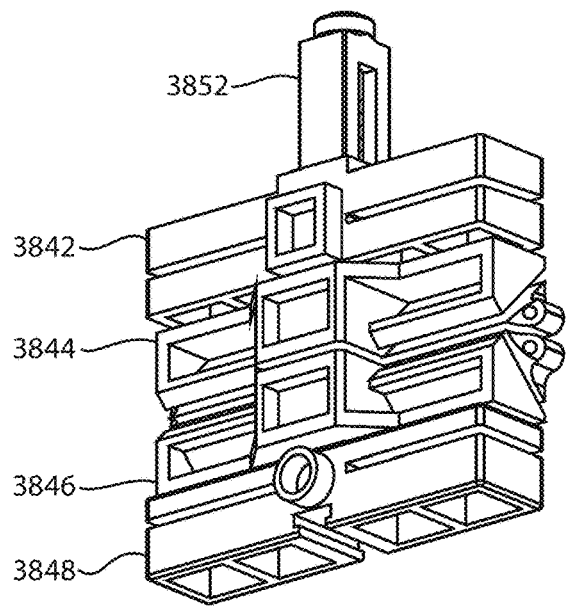
FIG. 22 is an oblique view of a femoral four-in-one cut guide assembly.
Figure 23:
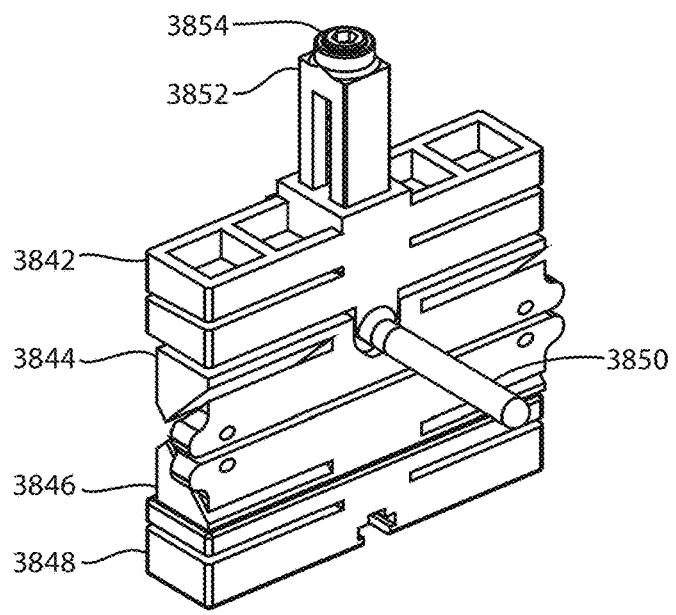
FIG. 23 is another oblique view of the femoral four-in-one cut guide assembly of FIG. 22 from a different direction.
Figures 24A, 24B:
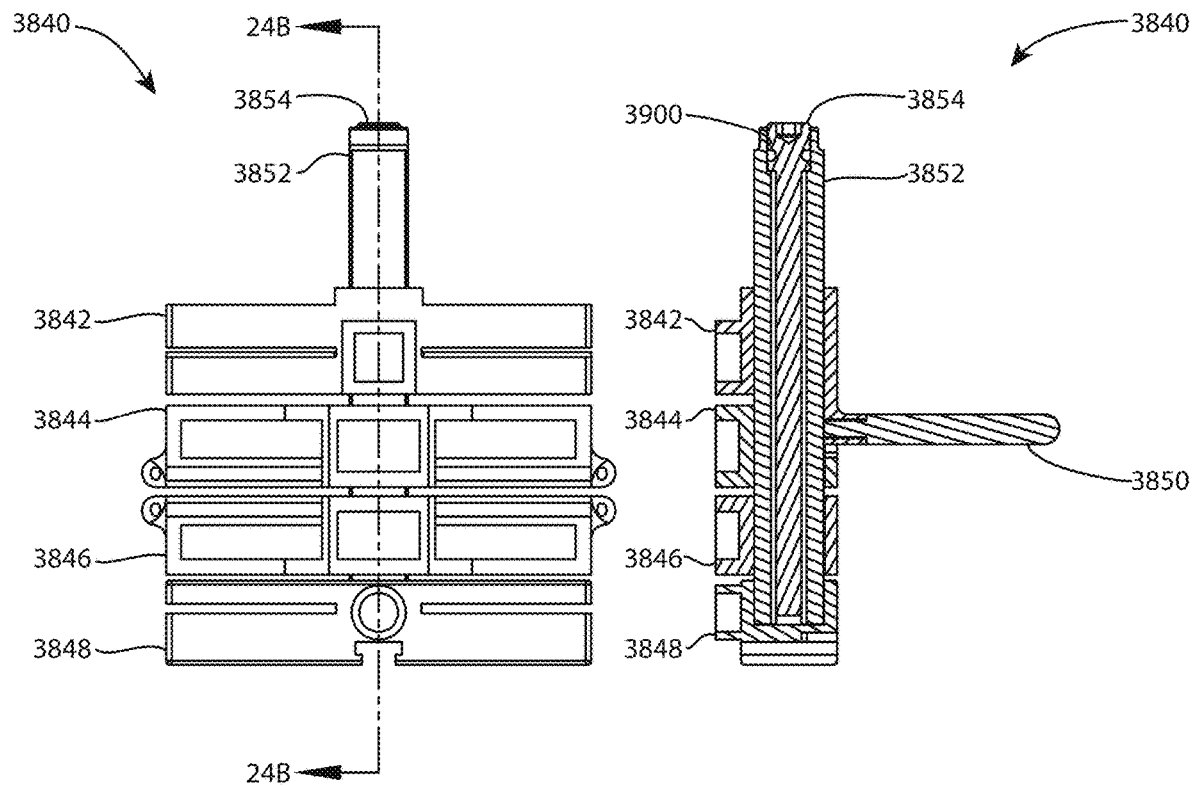
FIG. 24A is a front view of the femoral four-in-one cut guide assembly of FIG. 22.
FIG. 24B is a cross-sectional view of the femoral four-in-one cut guide assembly of FIG. 22 taken along section line 24B-24B of FIG. 24A.
Figures 25A, 25B:
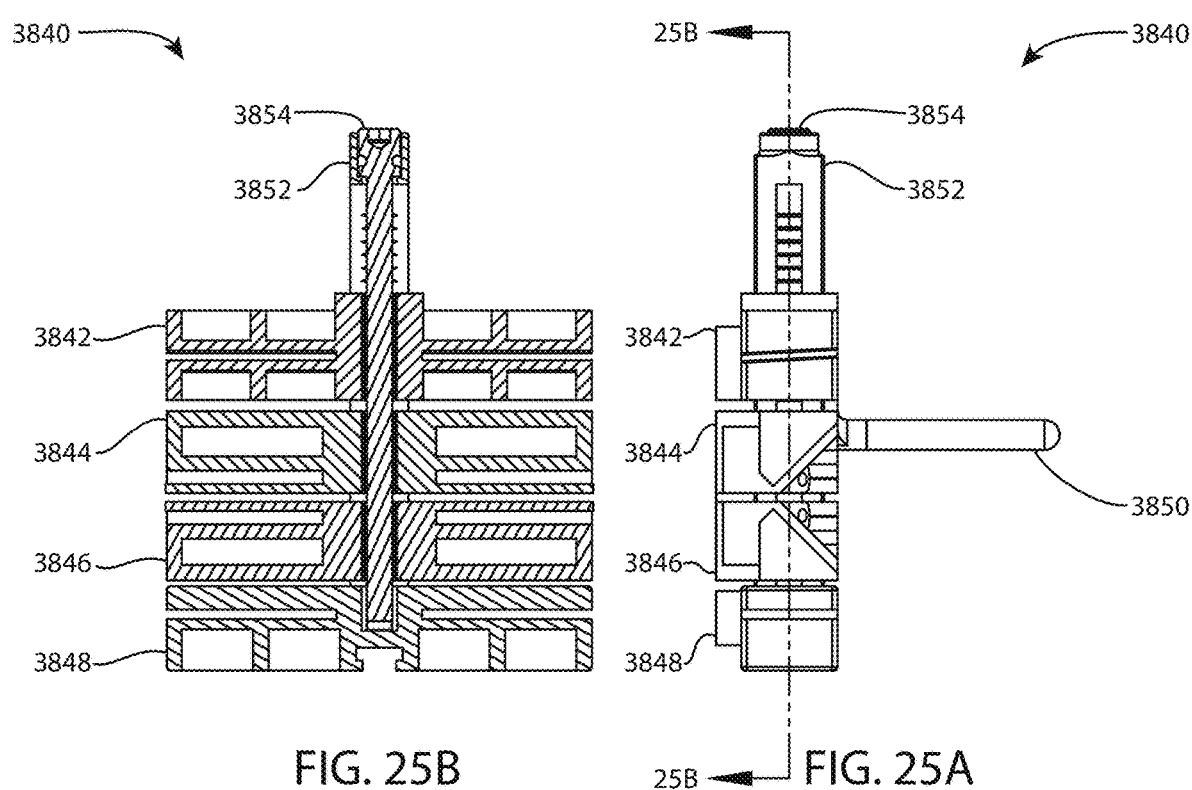
FIG. 25A is a side view of the femoral four-in-one cut guide assembly of FIG. 22.
FIG. 25B is a cross-sectional view of the femoral four-in-one cut guide assembly of FIG. 22 taken along section line 25B-25B of FIG. 25A.

When the adjustable distal femoral cut guide assembly 3730 is operatively assembled, rotating the screw 3740 causes the screw pin 3742 to translate proximal-distal along the shaft 3814. This causes the slider to pivot around the pivot pin 3736 within the window 3760 of the body 3732, which changes the angle 3836 between the saw slot 3774 of the body and an axis 3838 between the holes 3794, 3806 of the slide 3734. FIG. 20 shows the adjustable distal femoral cut guide assembly 3730 in a first state in which the angle 3836 is zero and the saw slot 3774 is parallel to the axis 3838. FIG. 21 shows the adjustable distal femoral cut guide assembly 3730 in a second state in which the angle 3836 is 7 degrees. This is advantageous in situations where the varus/valgus angle of the knee needs to be adjusted relative to the zero degree nominal condition.

The operatively assembled adjustable distal femoral cut guide assembly may be used, for example, in the steps shown in FIGS. 134 and 136 of U.S. patent application Ser. No. 15/630,555.

Referring to FIGS. 22-31, an adjustable femoral four-in-one cut guide assembly 3840 may include an anterior cut guide 3842, an anterior chamfer guide 3844, a posterior chamfer guide 3846, a posterior cut guide 3848, a post 3850, a rail or housing 3852, and a screw or locking element 3854. The illustrated adjustable femoral four-in-one cut guide assembly 3840 may be particularly adapted to be a single-use disposable instrument with most or all of its parts made mostly or entirely of plastic. The adjustable femoral four-in-one cut guide assembly 3840 may share certain characteristics with the femoral four-in-one cut guide assembly 3010 of U.S. patent application Ser. No. 15/630,555.

The anterior cut guide 3842 includes an H-shaped hole 3856 that extends through the anterior cut guide 3842 along the anterior-posterior direction. The narrow middle portion of the hole 3856 corresponding to the crossbar of the H-shape may include optional internal threads or ridges as shown. A saw slot 3858 extends through the anterior cut guide 3842 along the proximal-distal direction intended for the anterior femoral resection. The saw slot may be reinforced with metal. The saw slot 3858 may be divided into left and right portions as shown to maintain the structural integrity of the anterior cut guide 3842 in the vicinity of the hole 3856. An optional distal pocket 3860 or other connection feature may be present on the distal side of the anterior cut guide 3842. A square pocket 3860 is shown. A tab 3886 may extend posteriorly from the proximal side of the anterior cut guide 3842. The tab 3886 may include a hole 3888 that extends in the proximal-distal direction. The hole 3888 receives a reduced-diameter portion of the post 3850. Optionally, the tab 3886 may be integrally formed with the post 3850.

The anterior chamfer guide 3844 includes an H-shaped hole 3862 that extends through the anterior chamfer guide 3844 along the anterior-posterior direction. The narrow middle portion of the hole 3862 corresponding to the crossbar of the H-shape may include optional internal threads or ridges as shown. A saw slot 3864 extends through the anterior chamfer guide 3844 along a distal-posterior to proximal-anterior direction intended for the anterior femoral chamfer. The saw slot may be reinforced with metal. The saw slot 3864 may be divided into left and right portions as shown. An optional distal pocket 3866 or other connection feature may be present on the distal side of the anterior chamfer guide 3844. The pocket 3866 may be a different size and/or shape than the pocket 3860. A rectangular pocket 3866 is shown. Bilateral holes 3868 may be provided along the left and right sides of the anterior chamfer guide 3844. A notch 3890 may be formed in the anterior proximal portion of the anterior chamfer guide 3844. The notch 3890 receives the tab 3886 of the anterior cut guide 3842.

The posterior chamfer guide 3846 includes an H-shaped hole 3870 that extends through the posterior chamfer guide 3846 along the anterior-posterior direction. The narrow middle portion of the hole 3870 corresponding to the crossbar of the H-shape may include optional internal threads or ridges as shown. A saw slot 3872 extends through the posterior chamfer guide 3846 along a distal-anterior to proximal-posterior direction intended for the posterior femoral chamfer. The saw slot may be reinforced with metal. The saw slot 3872 may be divided into left and right portions as shown. An optional distal pocket 3874 or other connection feature may be present on the distal side of the posterior chamfer guide 3846. The pocket 3874 may be a different size and/or shape than either pocket 3860 or 3866. Another rectangular pocket 3874 is shown, which may be dimensionally different from pocket 3866. Bilateral holes 3876 may be provided along the left and right sides of the posterior chamfer guide 3846.

The posterior cut guide 3848 includes a blind H-shaped hole 3878 that extends into the anterior side of the posterior cut guide 3848 along the anterior-posterior direction. A saw slot 3880 extends through the posterior cut guide 3848 along the proximal-distal direction intended for the posterior femoral resection. The saw slot may be reinforced with metal. The saw slot 3880 may be divided into left and right portions as shown to maintain the structural integrity of the posterior cut guide 3848 in the vicinity of the hole 3878. An optional distal pocket 3882 or other connection feature may be present on the distal side of the posterior cut guide 3848. The pocket 3882 may be a different size and/or shape than any of the pockets 3860, 3866, or 3874. A circular pocket 3882 is shown. An undercut channel 3884 may be provided on the posterior aspect of the posterior cut guide 3848 and extending through the posterior cut guide 3848 along the proximal-distal direction, to receive the undercut rail 3062 of the latch mechanism 3026 of U.S. patent application Ser. No. 15/630,555, so that the adjustable femoral four-in-one cut guide assembly 3840 of the present application can be coupled to the proximal tibial cut guide 3012 of U.S. patent application Ser. No. 15/630,555 as shown in FIGS. 137A-D 141A-142 of U.S. patent application Ser. No. 15/630,555.

The post 3850 is a cylindrical part with a reduced diameter section 3892 at one end. The reduced diameter section 3892 is complementary to the hole 3888 of the anterior cut guide 3842.

The rail or housing 3852 is an elongated generally rectangular part that extends between an anterior end 3894 and a posterior end 3896. The anterior end 3894 includes a short circular portion, and the remainder of the housing 3852 has a rectangular or square exterior cross-sectional shape. A longitudinal hole 3898 extends through the housing 3852 between the anterior and posterior ends 3894, 3896. The hole 3898 may include a counterbore 3900 (FIG. 24B) in the anterior end 3894. A longitudinal slot 3902 extends into the housing 3852 from the posterior end 3896 and extends anteriorly to a location just posterior to the short circular portion at the anterior end 3894. The slot 3902 thus separates the housing 3852 into bilateral proximal and distal prongs 3904. The slot is narrower than the hole 3898.

The screw or locking element 3854 is an elongated generally cylindrical part with an enlarged anterior head 3906 at one end and a shaft 3908 extending from the head. A groove 3910 encircles the head 3906 near the junction with the shaft 3908. The head 3906 includes a torque fitting 3912, such as the hex socket shown. The shaft 3908 includes bilateral teeth 3914 extending from opposite sides of the shaft; otherwise the shaft 3908 is smooth. In one example, this arrangement may be achieved by externally threading the shaft 3908 and then removing the threads on opposite sides of the shaft.

The adjustable femoral four-in-one cut guide assembly 3840 may be assembled by performing the following steps. These steps may be performed in any order.

Inserting the reduced diameter section 3892 of the post 3850 in the hole 3888 of the anterior cut guide 3842. The post 3850 may be permanently fixed to the anterior cut guide 3842.

Inserting the locking element 3854 in the hole 3898 of the housing 3852 so that the head 3906 is received in the counterbore 3900 and the bilateral teeth 3914 are positioned next to the prongs 3904. Optionally, one or more pins (not shown) may be driven through the housing 3852 and the groove 3910 to make the locking element 3854 captive to the housing. Preferably, holes are made in the housing before driving the pins.

Inserting the housing 3852 with locking element 3854 through the hole 3856 of the anterior cut guide 3842, the hole 3862 of the anterior chamfer guide 3844, the hole 3870 of the posterior chamfer guide 3846, and into the hole 3878 of the posterior cut guide 3848 so that all of the distal sides of the guides face the same way and all of the anterior sides of the guides face the same way. The housing 3852 may snap into, or otherwise become fixed in, the hole 3878.

When the adjustable femoral four-in-one cut guide assembly 3840 is operatively assembled, the locking element, anterior cut guide, anterior chamfer guide, posterior chamfer guide, and posterior cut guide are all captive to the housing. The anterior cut guide, anterior chamfer guide, and posterior chamfer guide are each independently slidable along the housing 3852 relative to the posterior cut guide 3848 while the teeth 3914 of the locking element 3854 face the inner sides of the prongs 3904. The locking element 3854 is rotatable within the housing 3852. When the locking element 3854 is rotated so that the smooth sides of the shaft 3908 face the inner sides of the prongs 3904 and the teeth 3914 are exposed in the slot 3902, the teeth 3914 engage the narrow middle portions of the H-shaped holes 3856, 3862, 3870 thereby locking the positions of the anterior cut guide, anterior chamfer guide, posterior chamfer guide, and posterior cut guide relative to the locking element and housing. Optionally, the locking element teeth engage complementary teeth in the narrow middle portions of the H-shaped holes. In another arrangement, the narrow middle portions of the H-shaped holes are initially smooth, and turning the locking element causes its teeth to cut into the narrow middle portions to achieve locking.

Referring to FIGS. 28-31, a spacer 3920 may be used with the adjustable femoral four-in-one cut guide assembly 3840 to set the adjustable femoral four-in-one cut guide assembly 3840 to match a particular femoral implant size. The spacer 3920 establishes the proper spacing between the anterior cut guide, anterior chamfer guide, posterior chamfer guide, and posterior cut guide.

The spacer 3920 may have a body 3922 that extends between an anterior end 3924 and a posterior end 3926. The body 3922 is shown as a generally rectangular solid. An anterior arm 3928 extends proximally from the anterior end 3924 and has an anterior-posterior thickness 3930. A middle arm 3932 extends proximally from a middle portion of the body 3922 and has an anterior-posterior thickness 3934. A posterior arm 3936 extends proximally from the posterior end 3926 and has an anterior-posterior thickness 3938. The anterior-posterior space between the anterior and middle arms 3928, 3932 is large enough to receive the anterior chamfer guide 3844. The anterior-posterior space between the middle and posterior arms 3932, 3936 is large enough to receive the posterior chamfer guide 3846. A handle 3940 extends distally from the body 3922.

A set of spacers may be provided for use with the adjustable femoral four-in-one cut guide assembly 3840, each spacer corresponding to a unique size of femoral implant component.

The anterior arm 3928 of the spacer k3920 may be inserted between the anterior cut guide 3842 and the anterior chamfer guide 3844. The anterior chamfer guide 3844 may be received in the anterior-posterior space between the anterior and middle arms 3928, 3932. The middle arm 3932 may be inserted between the anterior chamfer guide 3844 and the posterior chamfer guide 3846. The posterior chamfer guide 3846 may be received in the anterior-posterior space between the middle and posterior arms 3932, 3936. The posterior arm 3936 may be inserted between the posterior chamfer guide 3846 and the posterior cut guide 3848. Optionally, a compressive force may be applied to the anterior side of the anterior cut guide 3842 and the posterior side of the posterior cut guide 3848, over the arms 3928, 3932, 3936. The locking element 3854 may be rotated 90 degrees to engage the teeth 3914 and the narrow middle portions of the H-shaped holes 3856, 3862, 3870 to lock all parts of the adjustable femoral four-in-one cut guide assembly 3840 to the desired size. The spacer 3920 may be removed before the adjustable femoral four-in-one cut guide assembly 3840 is coupled to the distal femur.

In an alternate embodiment, the spacer may engage the pockets 3860, 3866, 3874, 3882 provided on the anterior aspects of the anterior cut guide 3842, anterior chamfer guide 3844, posterior chamfer guide 3846, and posterior cut guide 3848. This may be advantageous when the spacer is made of plastic, as the pockets may allow the spacer arms to be larger than they would otherwise be if the arms fit between the cut guides. This may be advantageous for smaller size femoral components, regardless of the material of the spacer, where the gaps between the guides are small.

Referring to FIGS. 32-39, a foot holder assembly 3950 may include a foot receiver 3952, a lower bar 3954, a bridge 3956, a target mounting block 3958, a dovetail lock 3960, a target 3962, and a thumbscrew 3964. The target 3962 may include a slide 3966 and a cup 3968. The foot holder assembly 3950 may also include a post 3970, a pin 3972, a thumbscrew 3974, a rail 3976, and a screw 3978. Two posts 3970, pins 3972, and thumbscrews 3974 are shown. Three screws 3978 are shown. The foot holder assembly 3950 may share certain characteristics with the foot holder assemblies 1870, 2870 of U.S. patent application Ser. No. 15/630,555.

Figure 34:
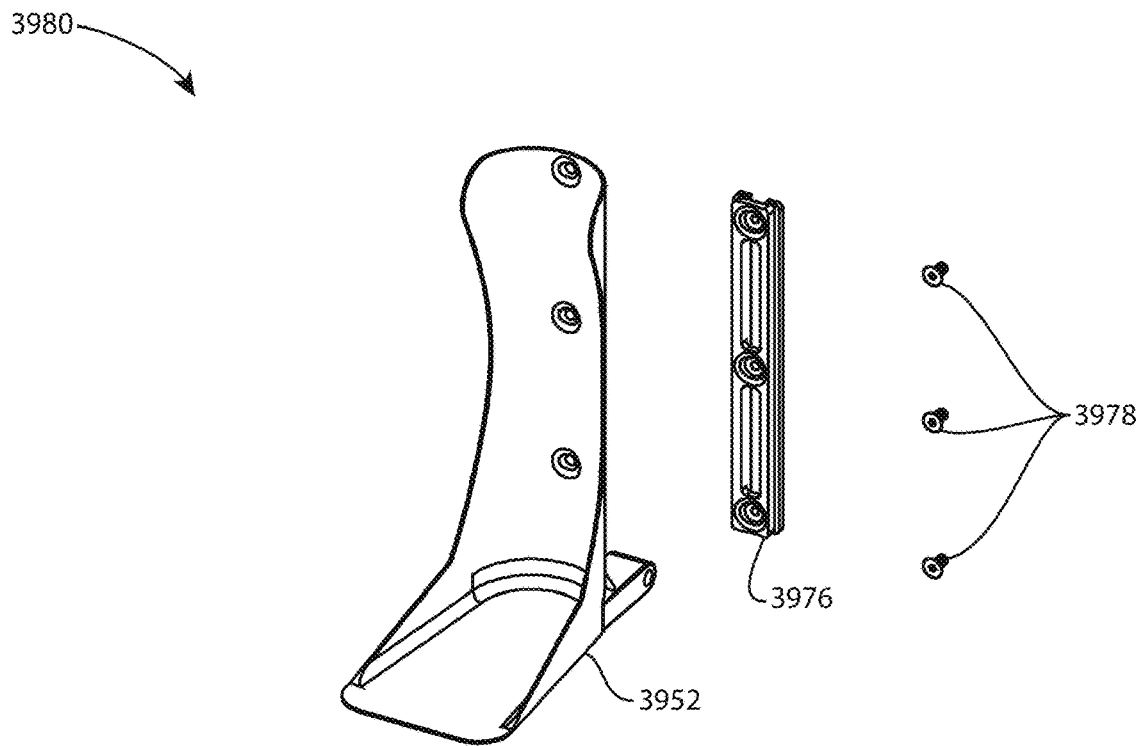
FIG. 34 is an oblique exploded view of a boot sub-assembly of the foot holder assembly of FIG. 32.
Figure 35:
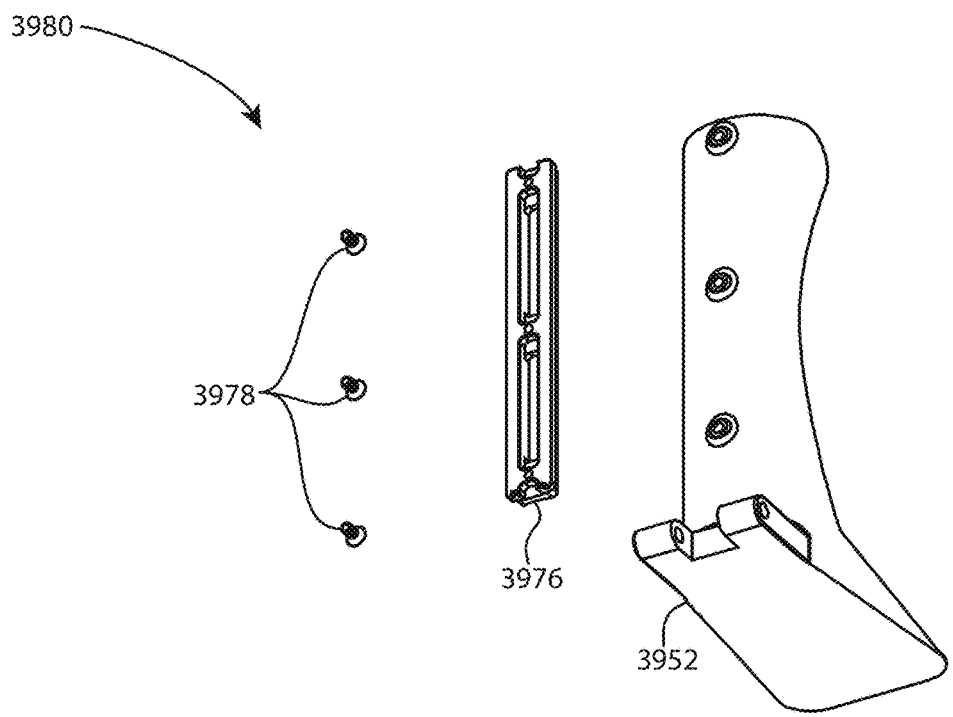
FIG. 35 is another oblique exploded view of the boot sub-assembly of FIG. 34 from a different direction.

Referring to FIGS. 34-35, the foot receiver 3952, rail 3976, and screw(s) 3978 may be coupled together to form a foot receiver sub-assembly 3980 of the foot holder assembly 3950. The rail 3976 is secured longitudinally to the back side of the foot receiver 3952 with one or more screws 3978. The rail 3976 has a T- or dovetail-shape in cross section.

Figure 36:
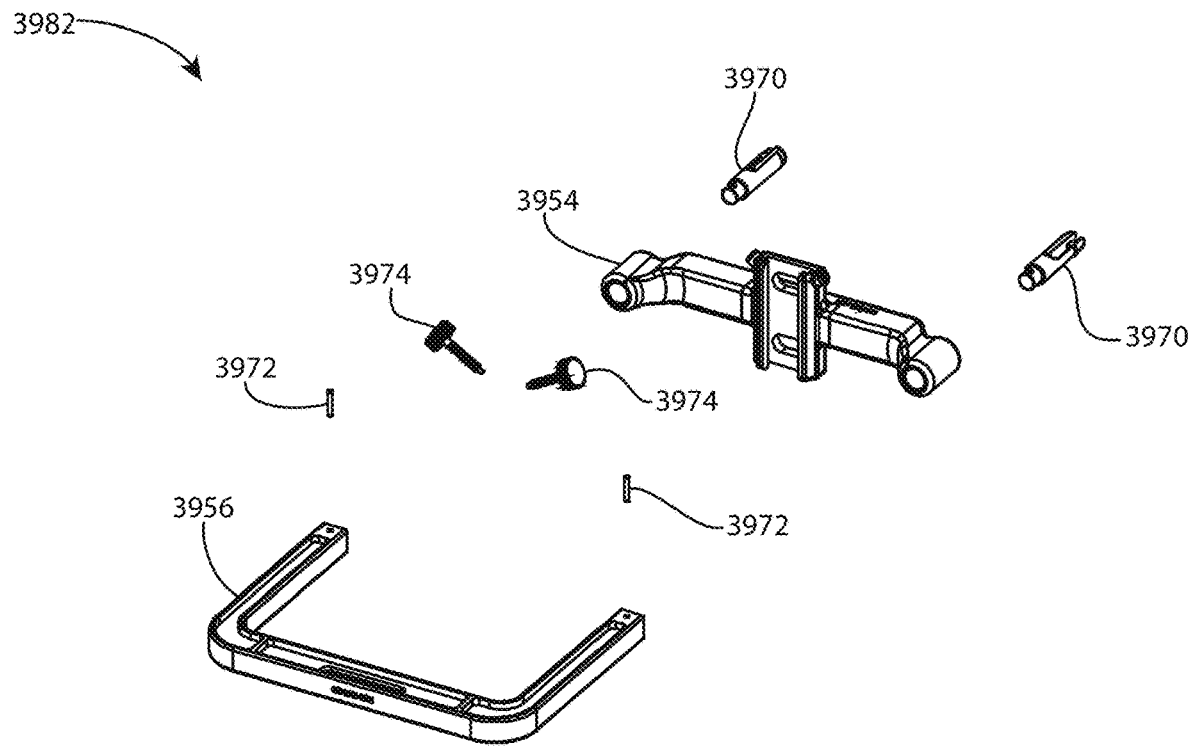
FIG. 36 is an oblique exploded view of a bridge sub-assembly of the foot holder assembly of FIG. 32.
Figure 37:
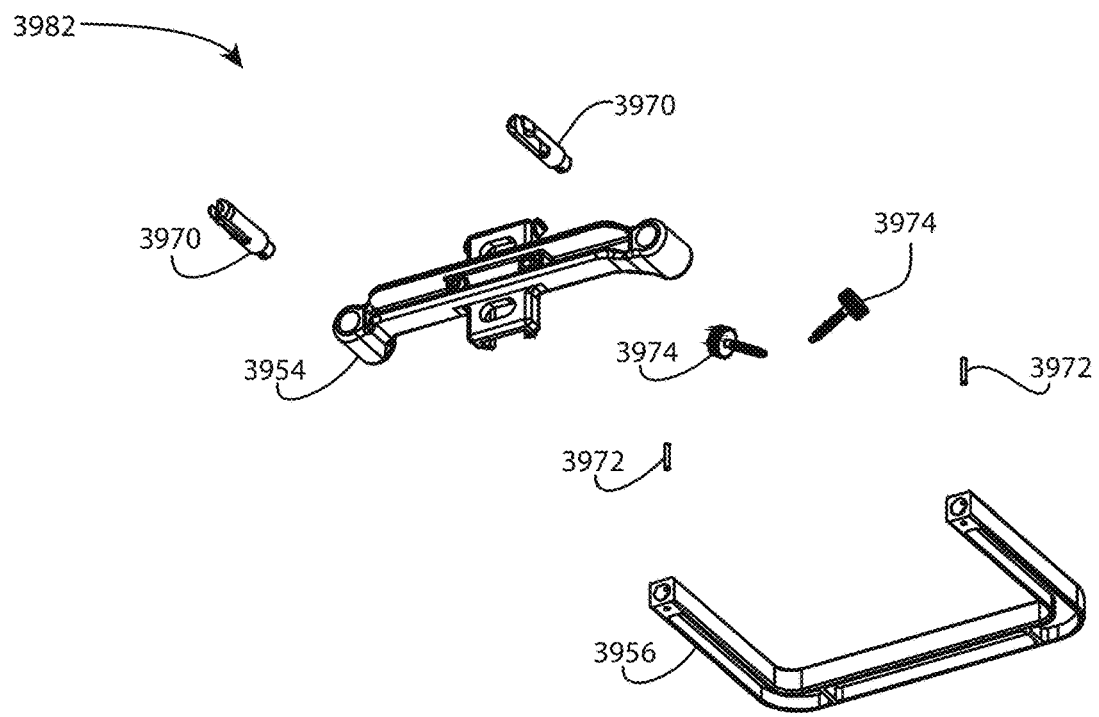
FIG. 37 is another oblique exploded view of the bridge sub-assembly of FIG. 36 from a different direction.

Referring to FIGS. 36-37, the bridge 3956, lower bar 3954, post(s) 3970, pin(s) 3972, and thumbscrew(s) 3974 may be coupled together to form a bridge sub-assembly 3982 of the foot holder assembly 3950. A post 3970 is inserted into each end of the bridge 3956 and secured with a pin 3972. The outward-facing ends of the posts 3970 are split to enable the posts 3970 to function as spring biased retainers for the lower bar 3954. A post 3970 is inserted into each end of the lower bar 3954. The lower bar 3954 includes a central groove feature which has complementary undercut geometry to the rail 3976 of the foot receiver sub-assembly 3980. The thumbscrews 3974 thread into oblique threaded sockets on either side of the groove feature.

Figure 38:
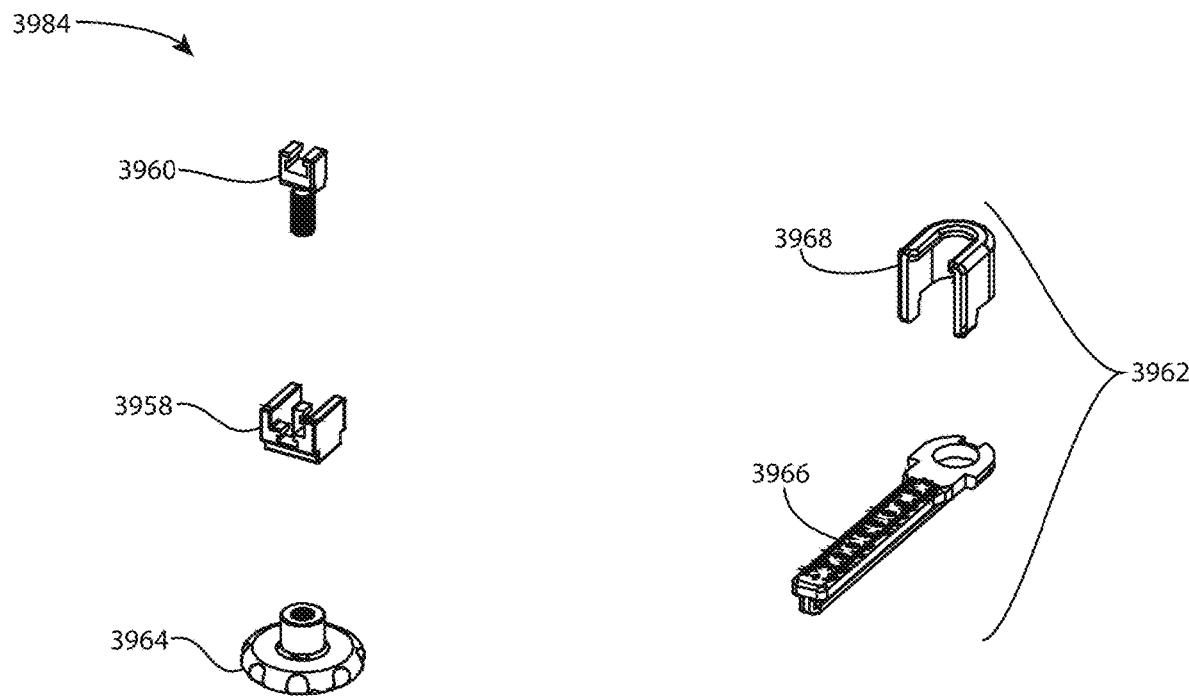
FIG. 38 is an oblique exploded view of a target sub-assembly of the foot holder assembly of FIG. 32.
Figure 39:
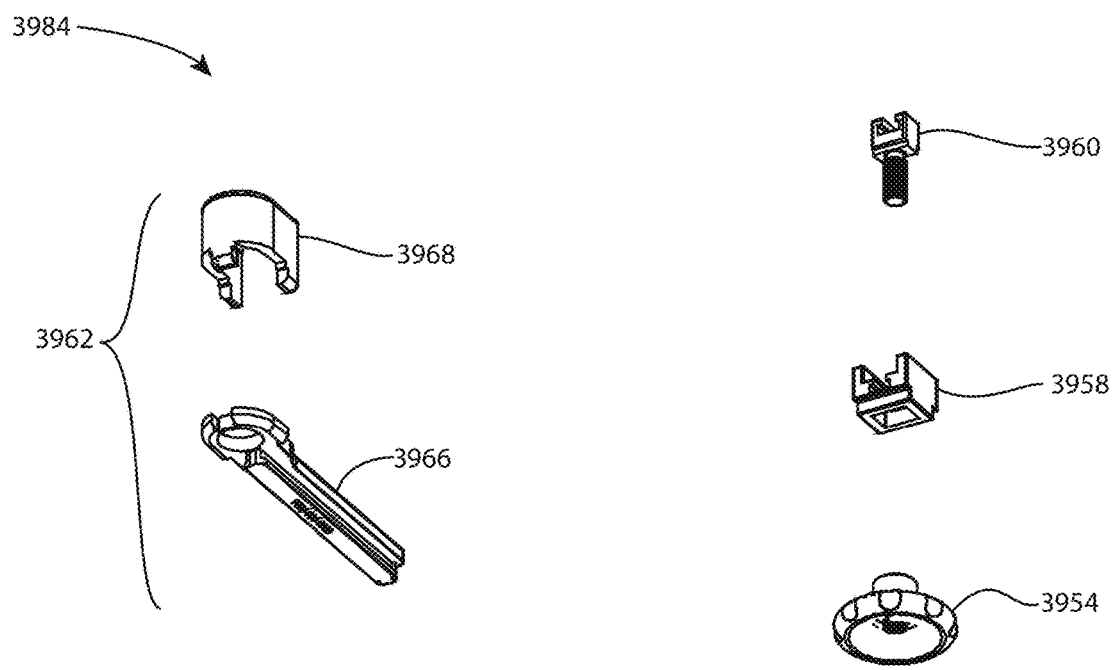
FIG. 39 is another oblique exploded view of the target sub-assembly of FIG. 38 from a different direction.
Figures 40, 41:
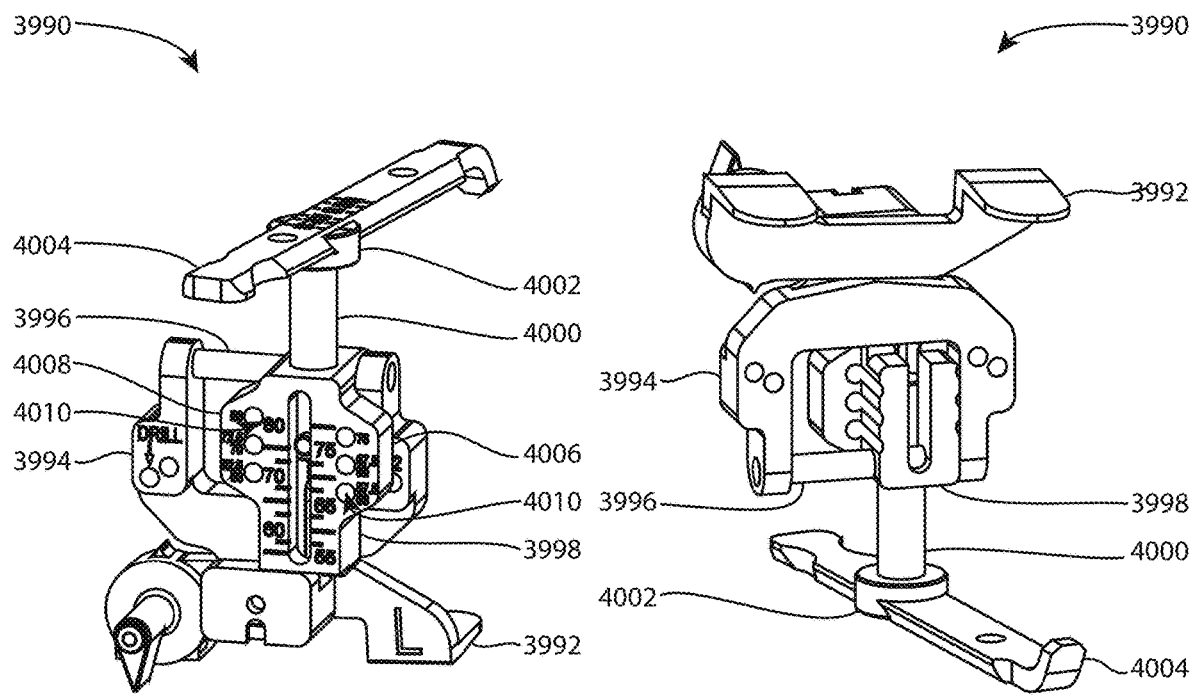
FIG. 40 is an oblique view of a femoral sizing guide.
FIG. 41 is another oblique view of the femoral sizing guide of FIG. 40 from a different direction.

Referring to FIGS. 38-39, the target 3962, slide 3966, cup 3968, target mounting block 3958, dovetail lock 3960, and thumbscrew 3964 may be coupled together to form a target sub-assembly 3984 of the foot holder assembly 3950. The slide 3966 and cup 3968 may be coupled together to make the target 3962, or formed as a single component part. The threaded shaft of the dovetail lock 3960 is inserted through a hole in the target mounting block 3958 and threaded into the thumbscrew 3964. When the dovetail lock 3960 and the target mounting block 3958 are coupled together, they share substantially the same T-slot geometry. The slide 3966 is inserted into the T-slot of the dovetail lock and target mounting block. The dovetail lock 3960 is movable relative to the target mounting block 3958 to apply or release a locking force to the slide 3966.

The foot holder assembly 3950 may be assembled by performing the following steps and/or the preceding steps for the three sub-assemblies. These steps may be performed in any order.

Figure 32:
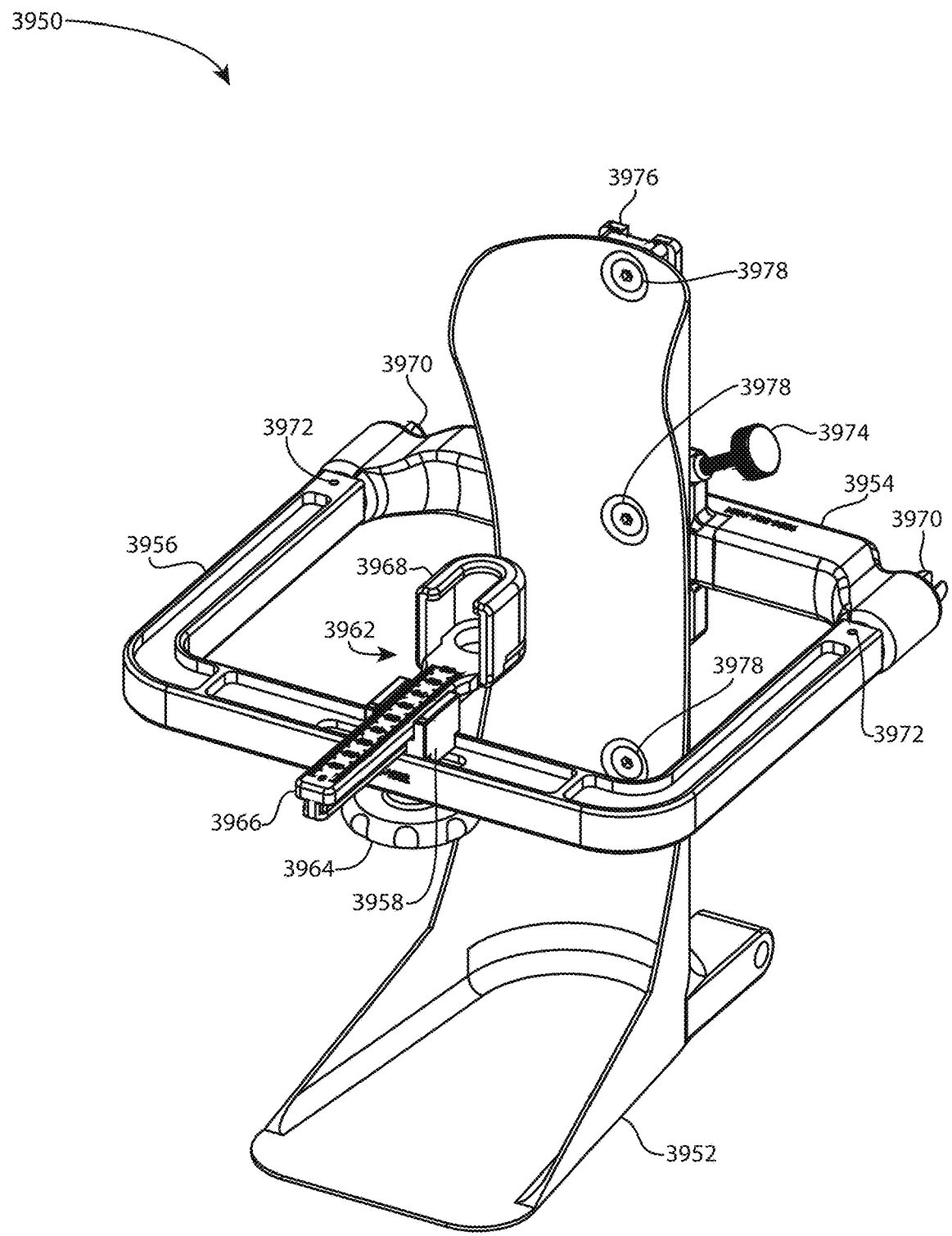
FIG. 32 is an oblique view of a foot holder assembly.
Figure 33:
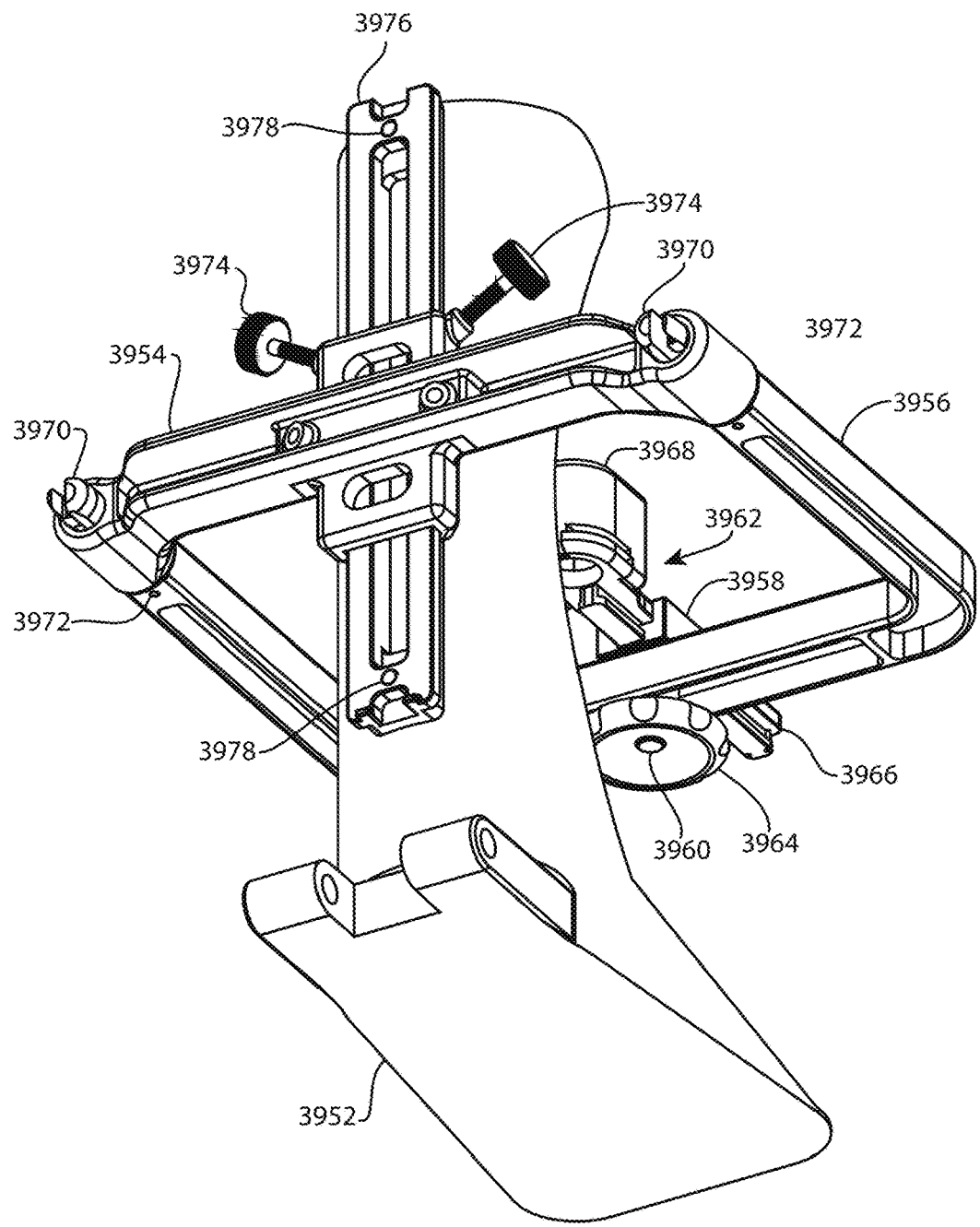
FIG. 33 is another oblique view of the foot holder assembly of FIG. 32 from a different direction.

Coupling the foot receiver sub-assembly 3980 and the bridge sub-assembly 3982 together by sliding the groove feature of the lower bar 3954 of the bridge sub-assembly 3982 over the rail 3976 of the foot receiver sub-assembly 3980. Preferably, the thumbscrews 3974 are proximal as shown in FIGS. 32-33.

Coupling the target 3962, slide 3966, cup 3968, target mounting block 3958, and dovetail lock 3960 as described for the target sub-assembly 3984, inserting the threaded shaft of the dovetail lock 3960 through a transverse slot of the bridge 3956 so that the cup 3968 is proximal to the bridge 3956 and facing the lower bar 3954, and threading the thumbscrew 3964 onto the threaded shaft of the dovetail lock 3960.

When the foot holder assembly 3950 is operatively assembled, it provides three degrees of freedom in translation of the target 3962: superior-inferior along the rail 3976, anterior-posterior along the slide 3966, and medial-lateral along the bridge slot. This version of the foot holder assembly 3950 provides sufficient three-dimensional adjustment to enable the user (surgeon) to position the cup 3968 of the target over the distal end of the tibia or over the anterior tibial spine, which nominally extends along the proximal ⅔ of the tibia, is well-centered relative to the mechanical axis of the leg in this region, and is typically easy to identify. The anterior-posterior adjustment may be employed to fine tune the resection angle of the proximal tibial plateau.

Referring to FIGS. 40-43, a femoral sizing guide assembly 3990 may include a base 3992, a body 3994, a rod 3996, a slide 3998, a post 4000, a post cap 4002, and an anterior feeler or stylus 4004. The femoral sizing guide assembly 3990 is a modification of a conventional femoral sizing guide.

The conventional femoral sizing guide is used to determine the size of the distal femur and to prepare proximal-distal post holes in the distal femur. The post holes receive proximally extending posts of a conventional four-in-one cut guide. This mounting scheme does not facilitate adjustment of the external rotation of the four-in-one cut guide. In order to adjust external rotation, the four-in-one cut guide is removed from the distal femur, new post holes are prepared, and the four-in-one cut guide is reattached to the distal femur using the new post holes.

The femoral sizing guide assembly 3990 is modified to provide a set of drill holes for placing a distal femoral pin upon which a modified four-in-one cut guide may be mounted and rotationally adjusted according to the principles developed by the inventors named in the current application.

The slide 3998 has been modified to include left and right panels 4006, 4008 that increase the medial-lateral width of the slide relative to the conventional design. Each panel 4006, 4008 includes one or more holes 4010 that extend through the slide 3998 along a proximal-distal direction. The example shows three holes 4010 in each panel 4006, 4008, arranged in a linear array along the anterior-posterior direction. Indicia are included to identify the hole that corresponds to a particular size femoral implant component.

Figures 42, 43:
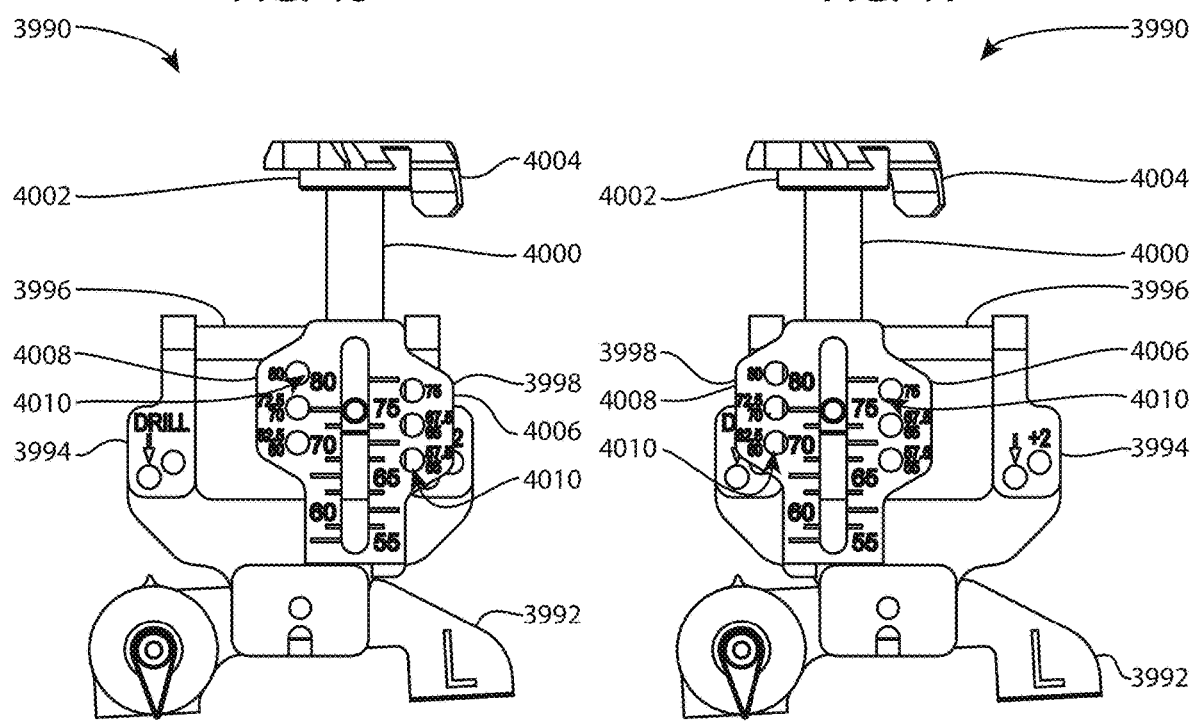
FIG. 42 is a front view of the femoral sizing guide of FIG. 40 with a sliding element in a first position.
FIG. 43 is another front view of the femoral sizing guide of FIG. 40 with a sliding element in a second position.

When the femoral sizing guide assembly 3990 is operatively assembled, the slide 3998 slides along the rod 3996 in the medial-lateral direction. FIG. 42 shows that when the slide 3998 is all the way towards the "L" paddle, the holes 4010 in panel 4008 are centered in the medial-lateral width of the femoral sizing guide assembly 3990. FIG. 43 shows that when the slide 3998 is all the way in the other direction away from the "L" paddle, the holes 4010 in panel 4006 are centered in the medial-lateral width of the femoral sizing guide assembly 3990. The holes 4010 are staggered to correspond to six femoral implant sizes.

The operatively assembled femoral sizing guide assembly 3990 may be used to place a distal femoral pin, similar to the steps shown in FIGS. 96A-B, 98-100, 128A-B, and 130-132 of U.S. patent application Ser. No. 15/630,555, albeit with different apparatus. The femoral sizing guide assembly 3990 establishes the correct implant size (and corresponding four-in-one cut guide size) and anterior-posterior position for the four-in-one cut guide and implant, and the distal femoral pin facilitates setting the external rotation of the four-in-one cut guide and implant independent of referencing the posterior aspects of the femoral condyles.

Figure 44:
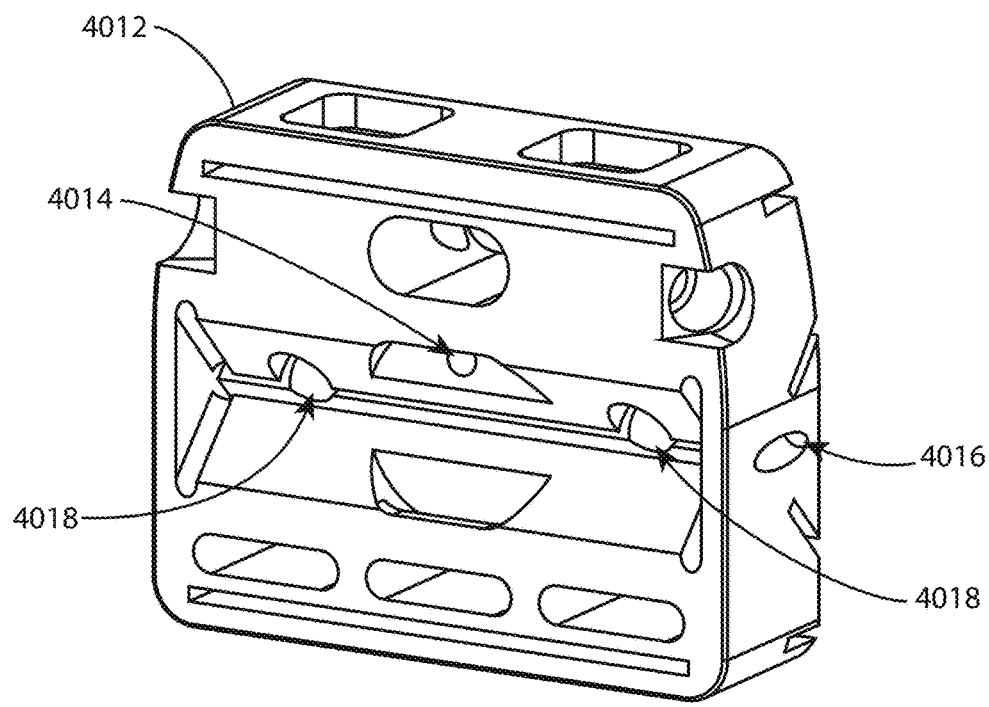
FIG. 44 is an oblique view of a four-in-one cut guide.
Figure 45:
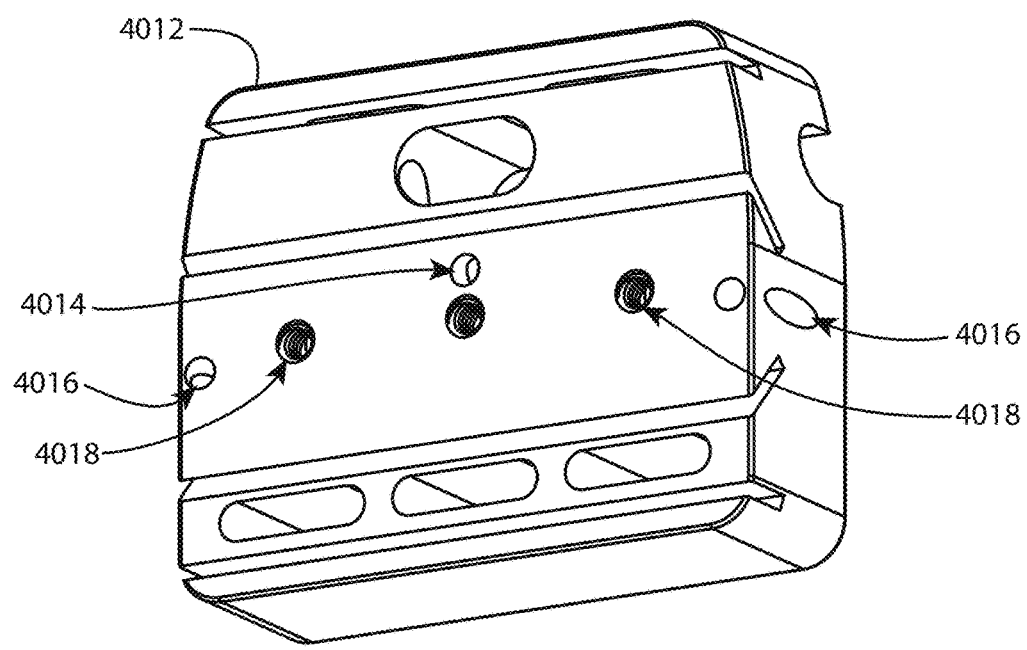
FIG. 45 is another oblique view of the four-in-one cut guide of FIG. 44 from a different direction.
Figure 46:
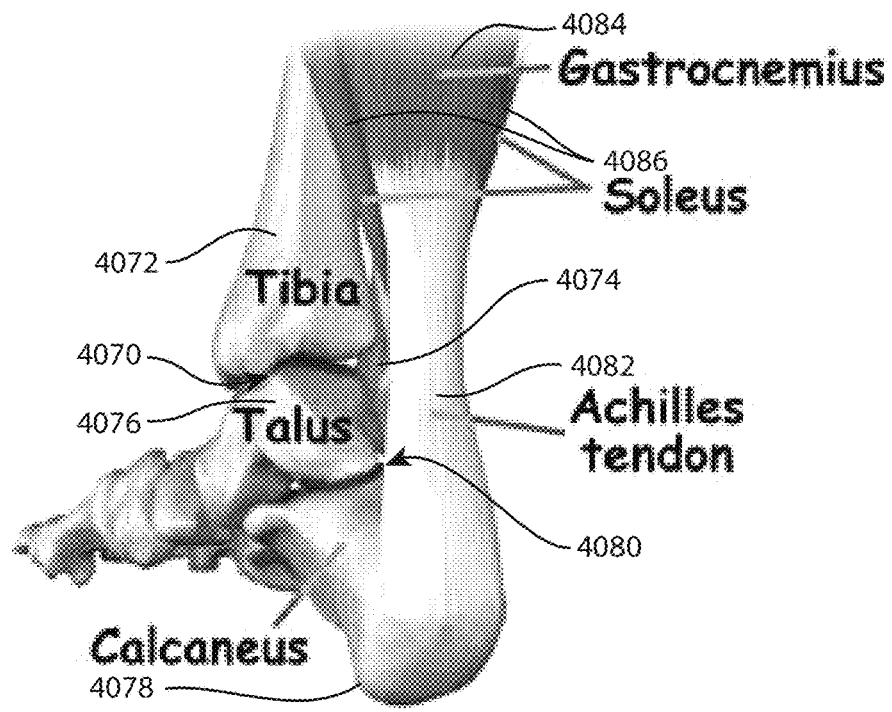
FIG. 46 is an oblique view of an ankle joint from a posterior-medial direction.
Figure 47:
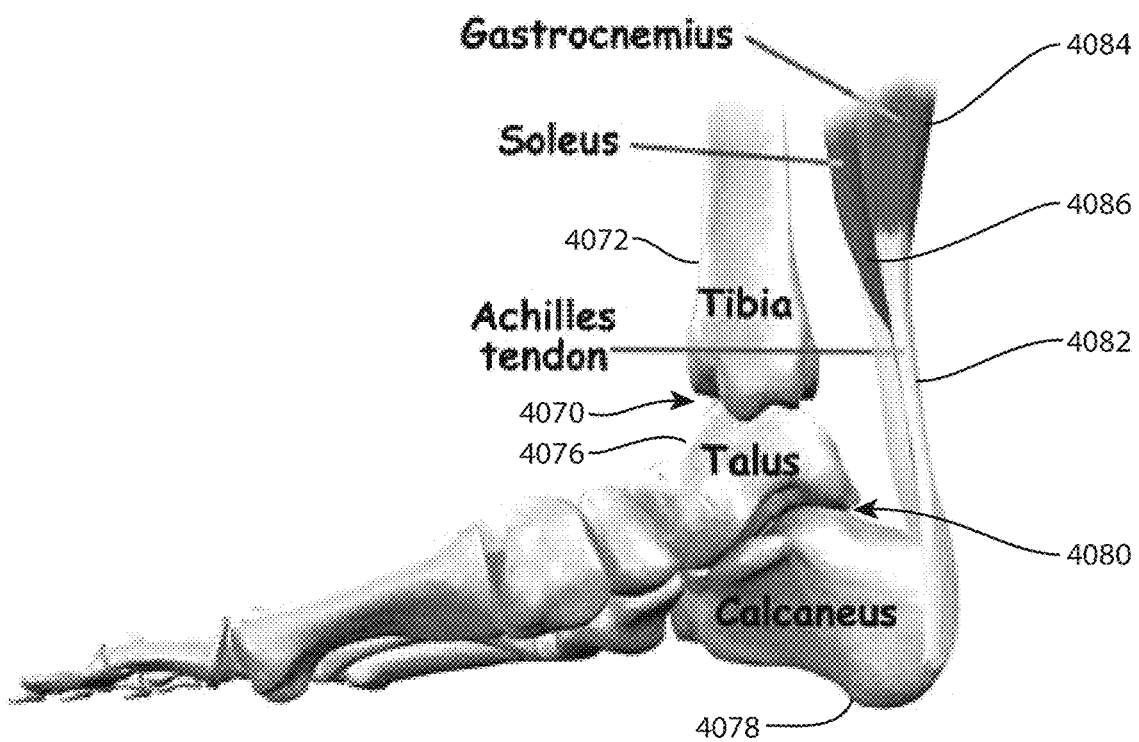
FIG. 47 is a medial view of an ankle joint.
Figure 48:
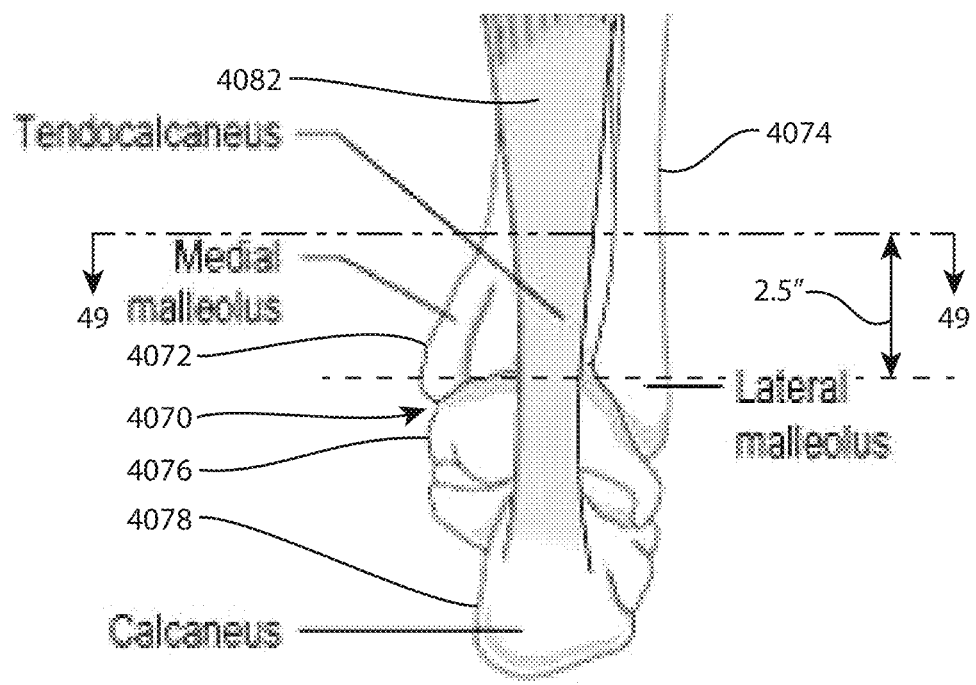
FIG. 48 is a posterior view of an ankle joint.

Referring to FIGS. 44-45, a conventional four-in-one cut guide 4012 has been modified to remove a pair of proximally-extending posts which corresponded to the holes shown in FIG. 42 near the indicia "DRILL" and in FIG. 43 near the indicia "+2." The four-in-one cut guide 4012 has also been modified to add a central through hole 4014 that extends in the proximal-distal direction. The four-in-one cut guide 4012 includes a first pair of bilateral smooth holes 4016 that extend obliquely through the guide and converge proximally, and a second pair of bilateral threaded holes 4018 that extend along the proximal-distal direction. In use, the four-in-one cut guide 4012 may initially be mounted to the distal femur by sliding the hole 4014 over a single central distal pin. The distal femoral pin may have been placed using the femoral sizing guide assembly 3990, the femoral pin guide assembly 3500, or other means. The four-in-one cut guide 4012 may be rotated about the distal femoral pin until the correct external rotation is achieved. Bilateral pins may then be driven through the holes 4016 and/or 4018 to fix the four-in-one cut guide 4012 to the femur.

Referring to FIGS. 46-49, bones and selected soft tissues of an ankle joint 4070 are shown. The ankle joint 4070 includes distal portions of a tibia 4072 and a fibula 4074 which articulate against a proximal portion of a talus 4076. The talus 4076 articulates against a calcaneus 4078 at a subtalar joint 4080. An Achilles tendon 4082 inserts into the middle part of the posterior superior aspect of the calcaneus 4078 and extends proximally to join a gastrocnemius muscle 4084, a soleus muscle 4086, and a plantaris muscle (not shown). These muscles act through the Achilles tendon 4082 to cause plantar flexion of the foot. For this reason, in normal anatomy the Achilles tendon 4082 is aligned directly posterior to the center of the ankle joint 4070 (FIG. 49), in other words, in line with the mechanical axis of the leg in this region. The Achilles tendon 4082 also happens to be readily palpable in most patients, making it easy to identify. For these reasons, the Achilles tendon 4082 may be a useful anatomical reference for finding the middle of the ankle joint 4070 in the process of aligning a tibial extension rod to the tibia. Fluoroscopy, radiographs, or other imaging may be unnecessary. Examples of tibial extension rods may be found in U.S. patent application Ser. Nos. 15/630,555 and 15/081,828, which are incorporated herein by reference in their entirety: at least tibial extension rods 313, 511, 1511, 2511.

While the preceding paragraph discusses the Achilles tendon 4082 with respect to normal anatomy, there may be circumstances where the relationship between the Achilles tendon 4082, the center of the ankle joint 4070, and the mechanical axis of the leg/tibia is disturbed due to bony deformity, ankle joint 4070 or subtalar joint problems, or derangement of the Achilles tendon 4082. For this reason, apparatus with adjustability may be preferable to apparatus with fixed relationships.

Referring to FIGS. 50-63, a foot holder assembly 4100 may include a foot holder sub-assembly 4102 or boot sub-assembly, a bridge sub-assembly 4104, a target sub-assembly 4106, and an Achilles tendon alignment guide sub-assembly 4108. These sub-assemblies may be functional, or they may represent groupings of parts for descriptive purposes. The foot holder assembly 4100 may share certain characteristics with the foot holder assembly 3950 and/or the foot holder assemblies 1870, 2870 of U.S. patent application Ser. No. 15/630,555.

Figure 53:
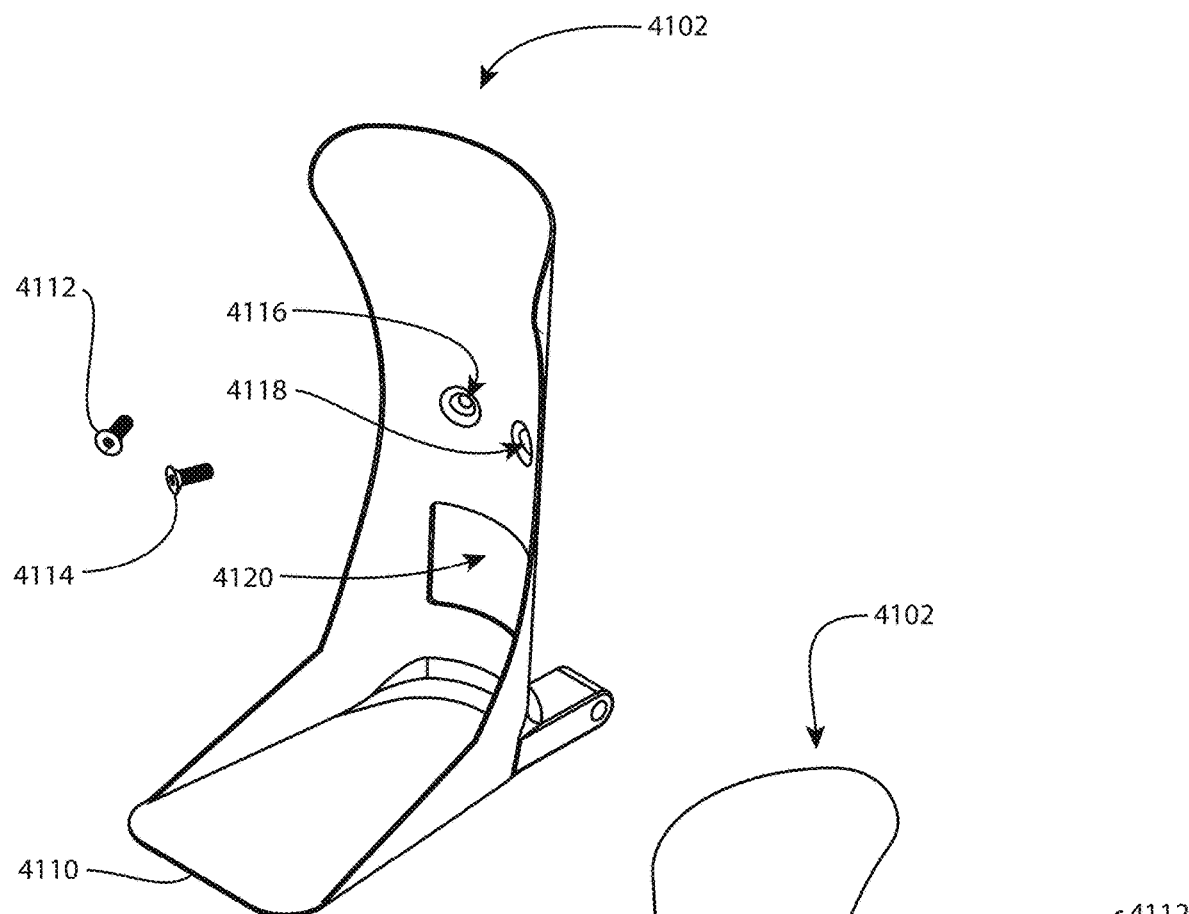
FIG. 53 is an oblique exploded view of a boot sub-assembly of the foot holder assembly of FIG. 51.
Figure 54:
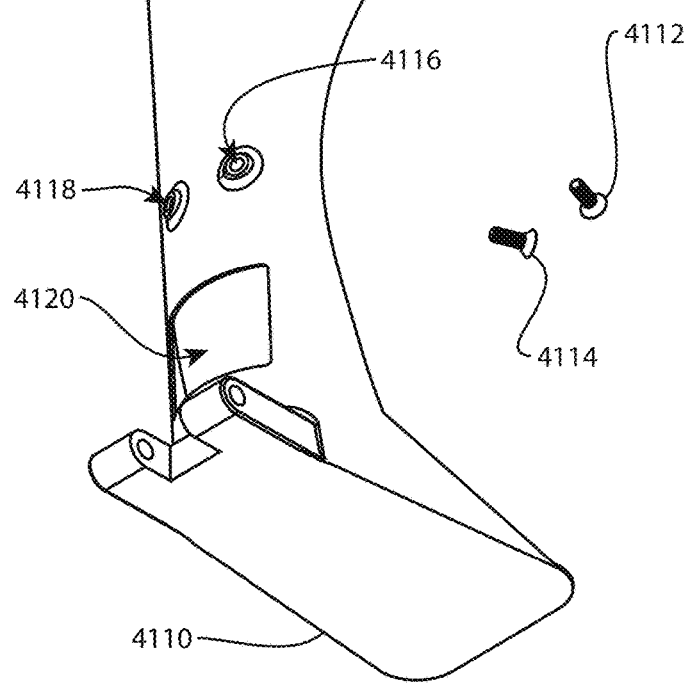
FIG. 54 is another oblique exploded view of the boot sub-assembly of FIG. 53 from a different direction.

Referring to FIGS. 53-54, the foot holder sub-assembly 4102 or boot sub-assembly may include a foot receiver 4110 or boot and a fastener. Two fasteners 4112, 4114 are shown.

The foot receiver 4110 may include holes 4116, 4118 which receive the fasteners 4112, 4114. The holes 4116, 4118 may be located in a proximal portion of the foot receiver 4110. The foot receiver 4110 may include a window 4120, which in this example is located in a distal portion of the foot receiver. The window 4120 may extend through the foot receiver 4110 along an anterior-posterior direction. The window 4120 may be rectangular as shown, or another shape which may be complementary to the Achilles tendon alignment guide sub-assembly 4108. It is contemplated that the foot receiver 4110 may include an optional hinge or flexible region (not shown) in the vicinity of the patient's ankle so that the patient's foot may be dorsiflexed or plantar flexed while secured within the foot receiver 4110.

Figure 55A:
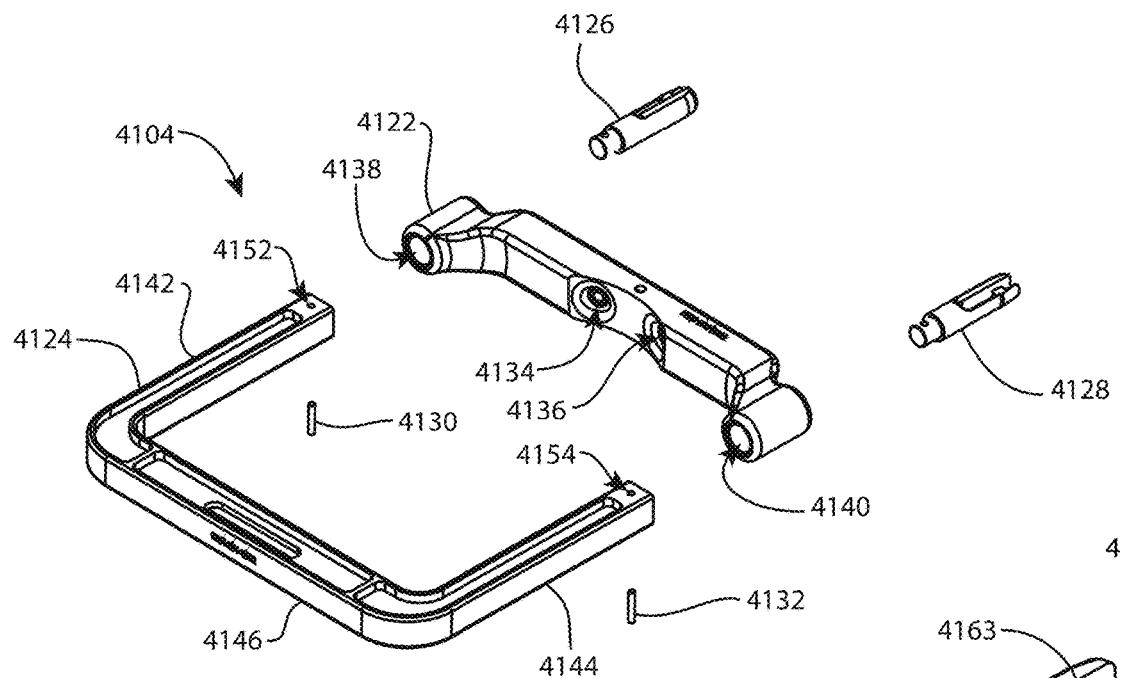
FIG. 55A is an oblique exploded view of a bridge sub-assembly of the foot holder assembly of FIG. 51.
Figure 55B:
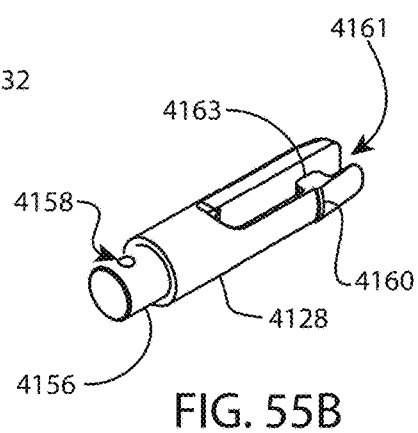
FIG. 55B is an enlarged detail view of a post of the bridge sub-assembly of FIG. 55A.
Figure 56:
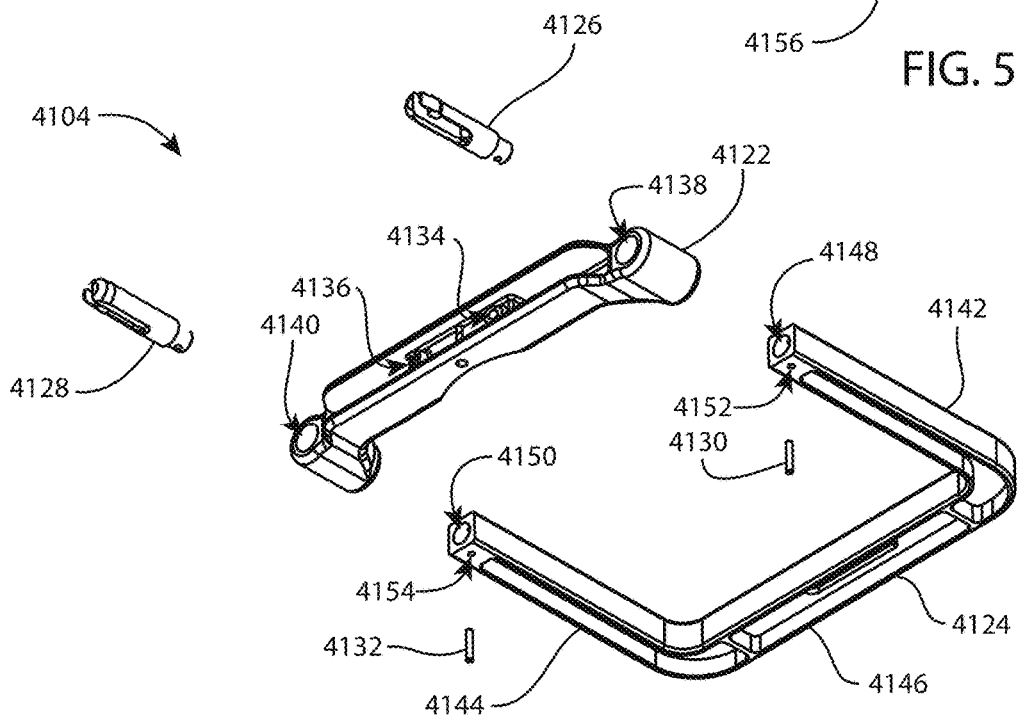
FIG. 56 is another oblique exploded view of the bridge sub-assembly of FIG. 55 from a different direction.

Referring to FIGS. 55-56, the bridge sub-assembly 4104 may include a bar 4122, a bridge 4124, posts 4126, 4128, and pins 4130, 4132.

The bar 4122 may include holes 4134, 4136 which receive the fasteners 4112, 4114 of the foot holder sub-assembly. The holes 4134, 4136 may be located in a central portion of the bar 4122. The bar 4122 may includes holes 4138, 4140 which receive the posts 4126, 4128. The holes 4138, 4140 may be located at each end of the bar 4122. The holes 4138, 4140 may extend parallel to each other along an anterior-posterior direction.

The bridge 4124 may be a generally C- or U-shaped part with first and second arms 4142, 4144 extending from a transverse body 4146. The arms 4142, 4144 may include holes 4148, 4150 which receive the posts 4126, 4128. The holes 4148, 4150 may extend parallel to each other along an anterior-posterior direction. The holes 4148, 4150 may be smaller in diameter than the holes 4138, 4140 of the bar 4122. The arms 4142, 4144 may include holes 4152, 4154 which receive the pins 4130, 4132. The holes 4152, 4154 may extend parallel to each other along a superior-inferior direction.

The posts 4126, 4128 may be identical. Referring to FIG. 55B, post 4128 may be a generally cylindrical part with an anterior boss 4156 which fits into hole 4150 of the bridge 4124. A hole 4158 may extend transversely through the boss 4156, and may receive the pin 4132. The remainder of the post 4128 posterior to the boss 4156 may have a larger diameter than the boss, and may fit into hole 4140 of the bar 4122. A lip 4160 may protrude transversely outwardly from a posterior portion of the post 4128, at least on one side as shown. A slot 4161 may extend anteriorly into the posterior end of the post 4128. A motion stop 4163 may be formed within the slot 4161 to limit its closure and/or expansion.

Figure 52:
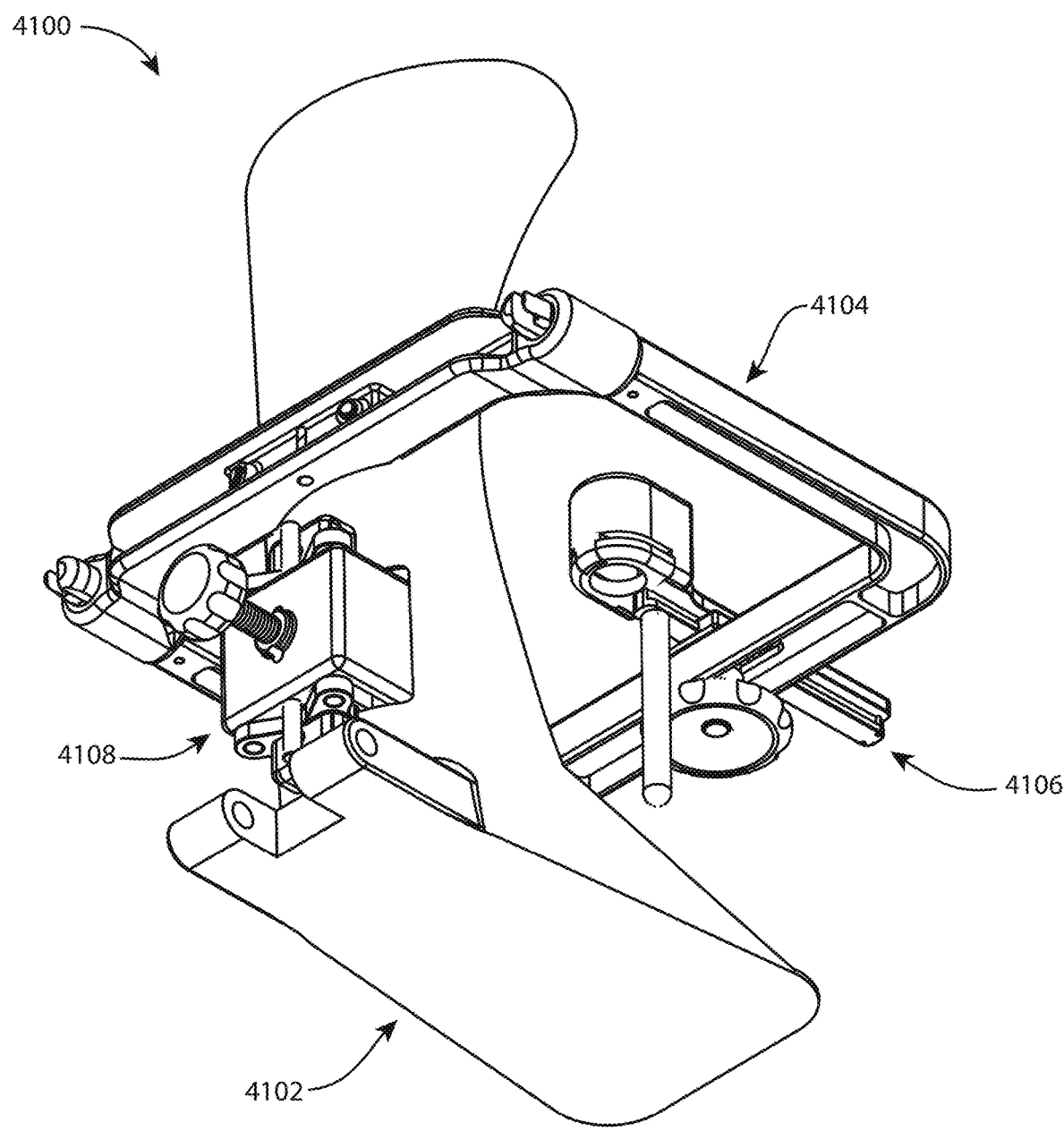
FIG. 52 is an oblique view of the foot holder assembly of FIG. 51 from a different direction.

The bridge sub-assembly 4104 may be assembled by inserting boss 4156 of post 4126 into hole 4148 of the bridge 4124 and securing the pin 4130 in holes 4152, 4158; inserting boss 4156 of post 4126 into hole 4150 of the bridge 4124 and securing the pin 4132 in holes 4154, 4158; and inserting posts 4126, 4128 into holes 4138, 4140 of the bar 4122. The exterior lips 4160 of the posts 4126, 4128 may have enough friction against the inside diameters of the holes 4138, 4140 to removably couple the bar 4122 to the bridge 4124, but preferably, the lips 4160 pass completely through the holes 4138, 4140 and snap outwardly once through. The bar 4122 may be disconnected from the bridge 4124 by pinching the posterior tips of the posts 4126, 4128 so that the lips 4160 fit back through the holes 4138, 4140. The bar 4122 may be assembled to the foot receiver 4110 by orienting the bar relative to the foot receiver as shown in FIG. 52, inserting the fastener 4112 into the holes 4116, 4134, and inserting the fastener 4114 into the holes 4118, 4136 to fix the bar to the foot receiver. When the bridge sub-assembly 4104 is fully assembled, the bar 4122, bridge 4124, posts 4126, 4128, and pins 4130, 4132 are all fixed together. The bridge 4124, posts 4126, 4128, and pins 4152, 4154 may function together as a sub-assembly in use, and the bar 4122 may function as part of the foot holder sub-assembly 4102, remaining coupled to the foot receiver 4110.

Figure 57:
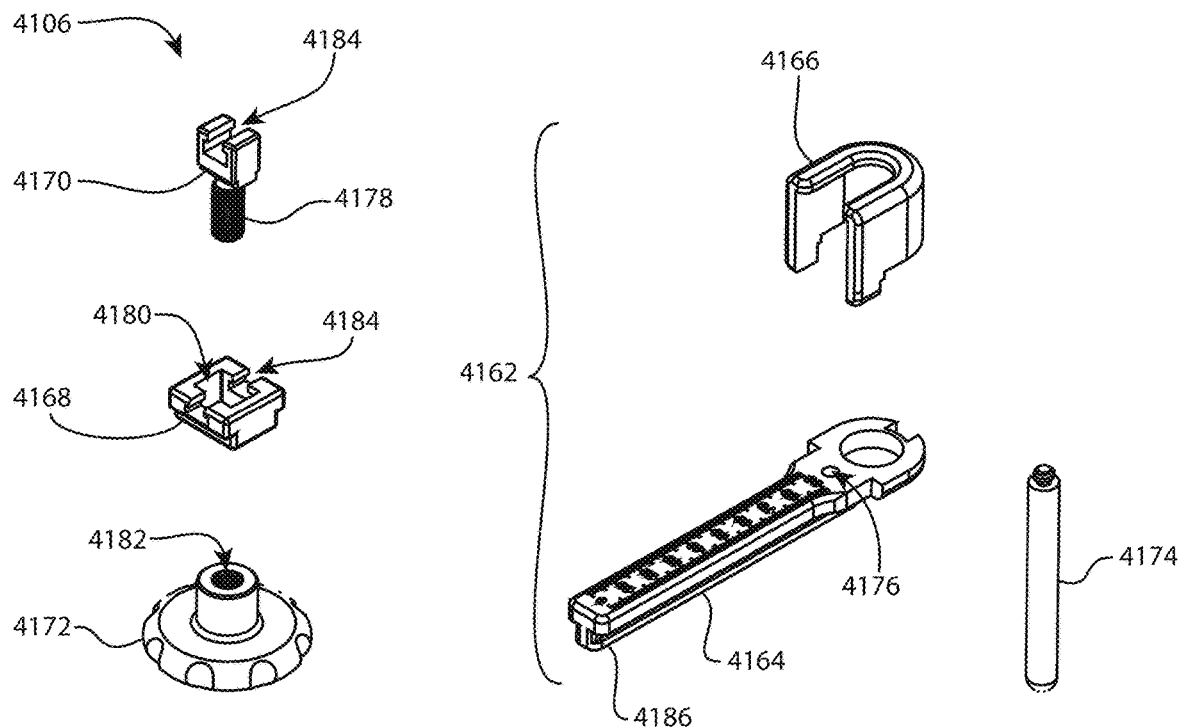
FIG. 57 is an oblique exploded view of a target sub-assembly of the foot holder assembly of FIG. 51.
Figure 58:
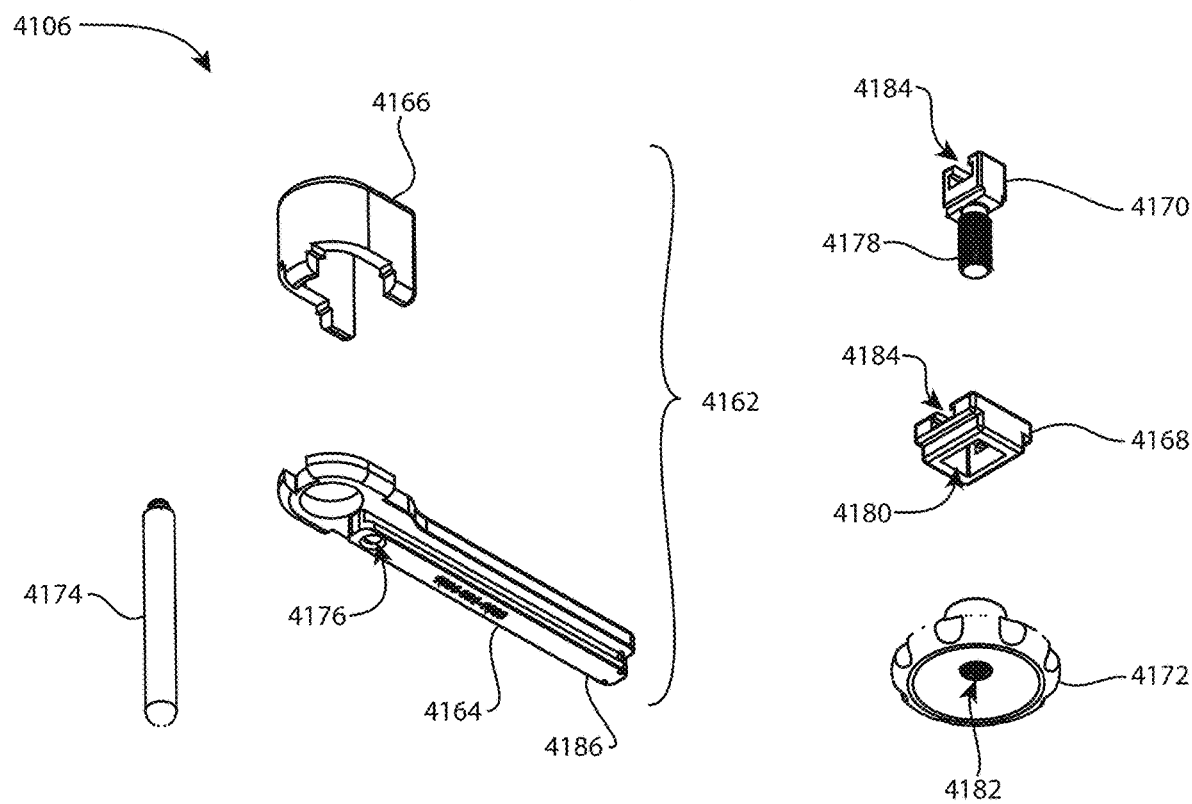
FIG. 58 is another oblique exploded view of the target sub-assembly of FIG. 57 from a different direction.
Figure 59:
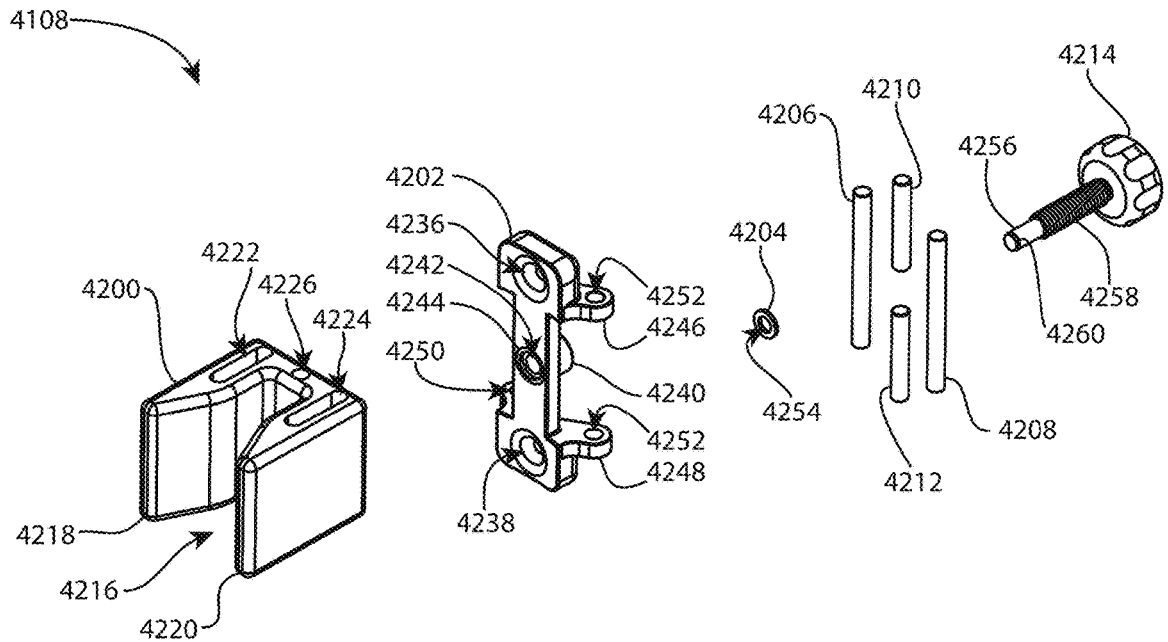
FIG. 59 is an oblique exploded view of an Achilles tendon alignment guide sub-assembly of the foot holder assembly of FIG. 51.
Figure 60:
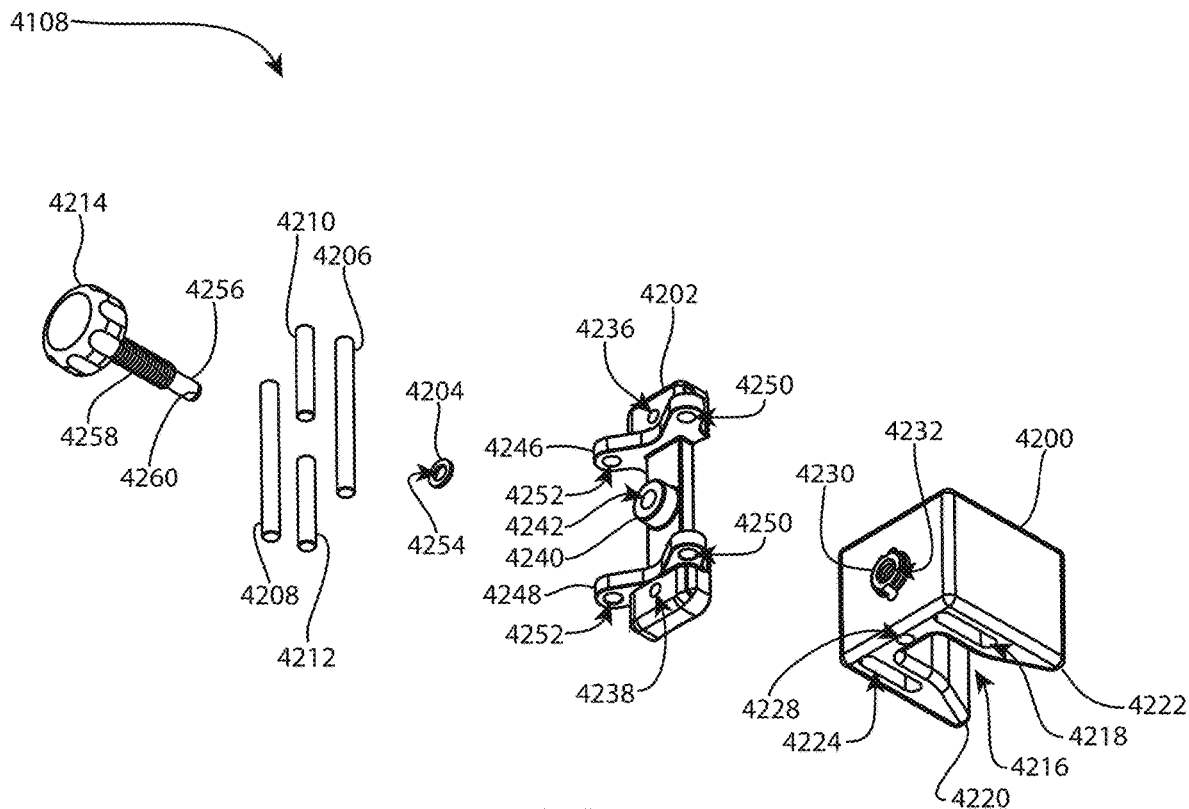
FIG. 60 is another oblique exploded view of the Achilles tendon alignment guide sub-assembly of FIG. 59 from a different direction.
Figure 61:
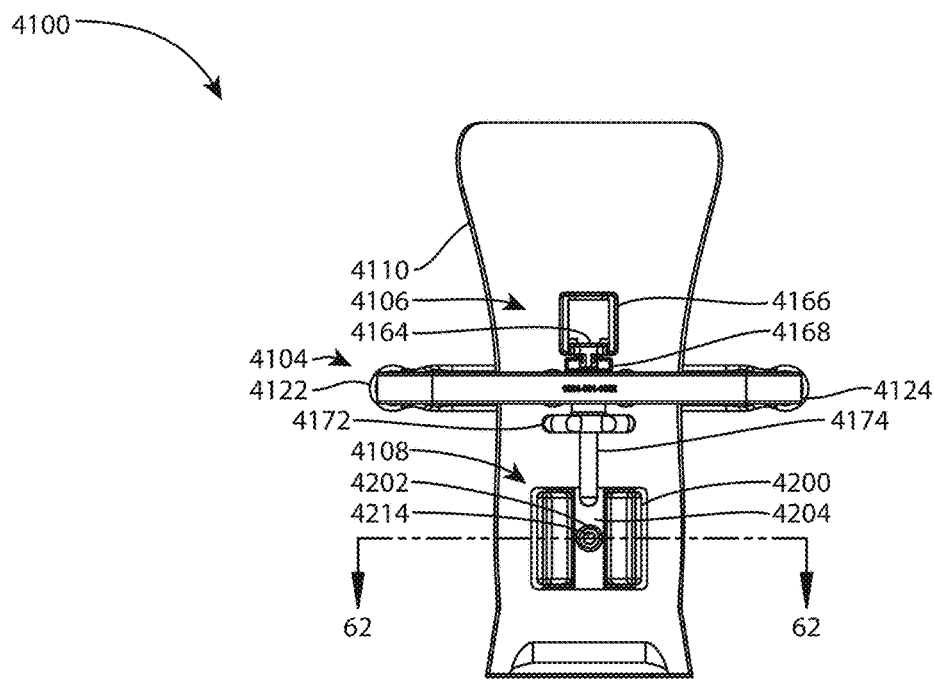
FIG. 61 is an anterior view of the foot holder assembly of FIG. 51.

Referring to FIGS. 57-58, the target sub-assembly 4106 may include a target 4162, slide 4164, cup 4166, target mounting block 4168, dovetail lock 4170, thumbscrew 4172, and post 4174. The slide 4164, cup 4166, and post 4174 may be coupled together to make the target 4162, or formed as a single component part. The post 4174 may thread into hole 4176 of the slide 4164 and extend inferiorly. A threaded shaft 4178 of the dovetail lock 4170 may be inserted through a hole 4180 in the target mounting block 4168 and threaded into a hole 4182 in the thumbscrew 4172. When the dovetail lock 4170 and the target mounting block 4168 are coupled together, they may share substantially the same T-slot geometry 4184. A T-rail 4186 of the slide 4164 may be inserted into the T-slot 4184 of the dovetail lock and target mounting block. The dovetail lock 4170 is movable relative to the target mounting block 4168 by twisting the thumbscrew 4172 to apply or release a locking force to the slide 4164. When the target sub-assembly 4106 is fully assembled, the target 4162 is movable relative to the target mounting block 4168, dovetail lock 4170, and thumbscrew 4172 along an anterior-posterior direction established by the T-slot 4184 and T-rail 4186. Tightening the thumbscrew 4172 locks the target 4162 in a position, and loosening the thumbscrew 4172 unlocks the target 4162 so that it can be moved.

Referring to FIGS. 59-63, the Achilles tendon alignment guide sub-assembly 4108 may include a body 4200 or Achilles receiver, a base 4202 or bracket, a collar 4204 or washer, pins 4206, 4208, 4210, 4212, and a thumbscrew 4214.

Figures 62, 63:
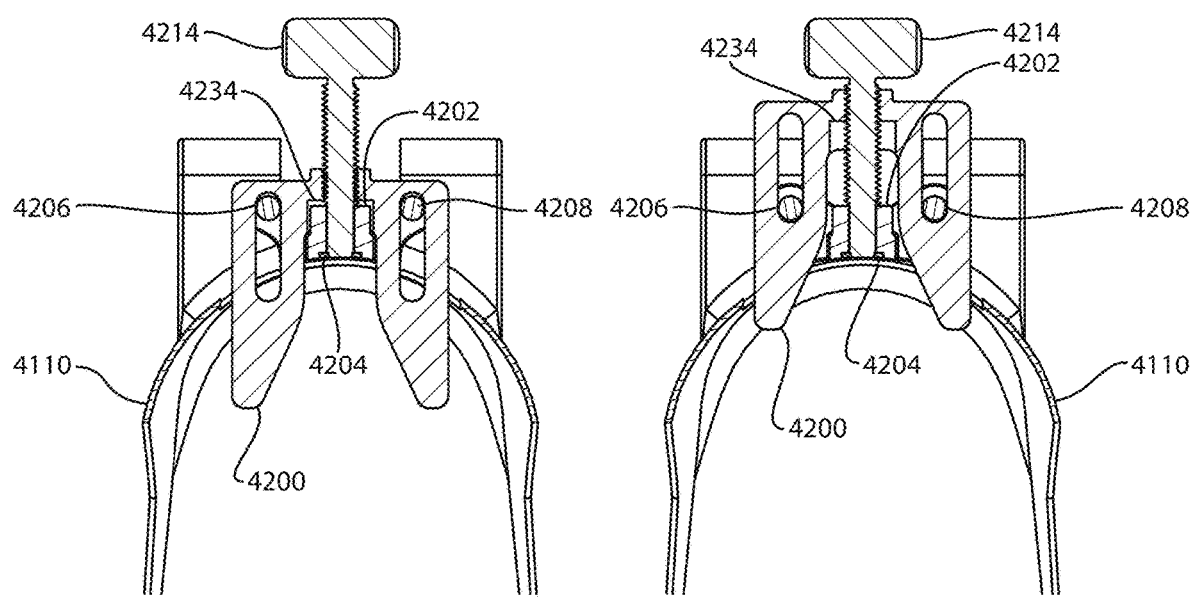
FIG. 62 is a cross-sectional view of the foot holder assembly of FIG. 51, taken along section line 62-62 of FIG. 61, with the Achilles tendon alignment guide sub-assembly in an anterior state.
FIG. 63 is a cross-sectional view of the foot holder assembly of FIG. 51, taken along section line 62-62 of FIG. 61, with the Achilles tendon alignment guide sub-assembly in a posterior state.

The body 4200 or Achilles receiver may include a notch 4216 which extends posteriorly into the body. The notch 4216 may be sized and shaped to receive an Achilles tendon of a patient. First and second arms 4218, 4220 may extend anteriorly on either (medial-lateral) side of the notch 4216. The body 4200 may have an overall C- or U-shape due to the notch 4216 and arms 4218, 4220. First and second slots 4222, 4224 may extend through the body 4200 along a superior-inferior direction, the slots being elongated along an anterior-posterior direction. The slots 4222, 4224 may receive the pins 4206, 4208. The slots 4222, 4224 may be located in posterior ends of the arms 4218, 4220. The slots 4222, 4224 may be parallel to each other. A hole 4226 may extend inferiorly into a central portion of the body 4200. The hole 4226 may receive the pin 4210. The hole 4226 may be parallel to the slots 4222, 4224. A hole 4228 may extend superiorly into a central portion of the body 4200, and may be coaxial with the hole 4226. The hole 4228 may receive the pin 4212. The holes 4226, 4228 may each extend less than halfway through the body 4200 along a superior-inferior direction. A boss 4230 may protrude posteriorly from a central portion of a posterior side of the body 4200. A threaded hole 4232 may extend through the boss 4230 and the body 4200 along an anterior-posterior direction. The threaded hole 4232 may receive a threaded shaft 4258 of the thumbscrew 4214. The anterior end of the threaded hole 4232, within the notch 4216, may include a counterbore 4234 (FIGS. 62-63).

The base 4202 or bracket may be elongated along a superior-inferior direction. The base 4202 may include a through hole 4236 that extends through a superior portion of the base 4202, and a through hole 4238 that extends through an inferior portion of the base 4202. The holes 4236, 4238 may extend along an anterior-posterior direction. A boss 4240 may protrude posteriorly from a central portion of a posterior side of the base 4202. A hole 4242 may extend through the boss 4240 and the base 4202 along an anterior-posterior direction. The hole 4242 may receive a non-threaded smooth shaft 4256 of the thumbscrew 4214. The anterior end of the hole 4242 may include a counterbore 4244. The base 4202 may include a protrusion 4246 that extends posteriorly from the posterior side of the base 4202 between the hole 4236 and the boss 4240, and a protrusion 4248 that extends posteriorly from the posterior side of the base 4202 between the hole 4238 and the boss 4240. Holes 4250, 4252 may extend through the protrusions 4246, 4248 along a superior-inferior direction. The holes 4250, 4252 may be bilaterally located on opposite sides of the superior-inferior linear array of holes 4236, 4238, 4242.

The collar 4204 or washer may include a through hole 4254.

The thumbscrew 4214 may include a non-threaded smooth shaft portion 4256 at the anterior tip, and a threaded shaft portion 4258 posterior to the smooth shaft portion. The smooth shaft portion 4256 may include a circumferential step-down 4260 or groove near its anterior tip end.

The Achilles tendon alignment guide sub-assembly 4108 may be assembled by inserting the pin 4210 in the hole 4226, inserting the pin 4212 in the hole 4228, inserting the base 4202 into the notch 4216 of the body 4200 so that the boss 4240 is received in the counterbore 4234, inserting the pin 4206 through the hole 4250 and slot 4222, inserting the pin 4208 through the hole 4252 and slot 4224, threading the threaded shaft portion 4258 of the thumbscrew into the hole 4232 so that the non-threaded smooth shaft portion 4256 is received in the hole 4242 with its tip protruding into the counterbore 4244, and receiving the step-down 4260 or groove in the hole 4254 of the collar 4204 so that the collar 4204 is received in the counterbore 4244. The pins 4210, 4212 may be fixed in holes 4226, 4228 by a press fit, welding or the like, or with fasteners such as set screws.

Referring to FIGS. 62-63, when the Achilles tendon alignment guide sub-assembly 4108 is assembled, rotating the thumbscrew 4214 clockwise and counterclockwise moves the body 4200 relative to the base 4202 along an anterior-posterior direction between an anterior state or position, FIG. 62, and a posterior state or position, FIG. 63. The anterior state may be used to directly reference the patient's Achilles tendon as the foot holder assembly 4100 is being coupled to the patient's lower leg and foot. Once the patient's lower leg and foot are secured within the foot holder assembly 4100, the Achilles tendon alignment guide sub-assembly 4108 may be moved to the posterior state to relieve pressure on the Achilles tendon 4082.

The foot holder assembly 4100 may be assembled by performing the following steps before, after, in addition to, or instead of the sub-assembly steps discussed above. These steps may be performed in any order.

Orienting the bar 4122 relative to the foot receiver 4110 as shown in FIG. 52, inserting the fastener 4112 through the hole 4116 and into the hole 4134, and inserting the fastener 4114 through the hole 4118 and into the hole 4136. The bar 4122 may be fixed to the foot receiver 4110 in this step.

Figure 51:
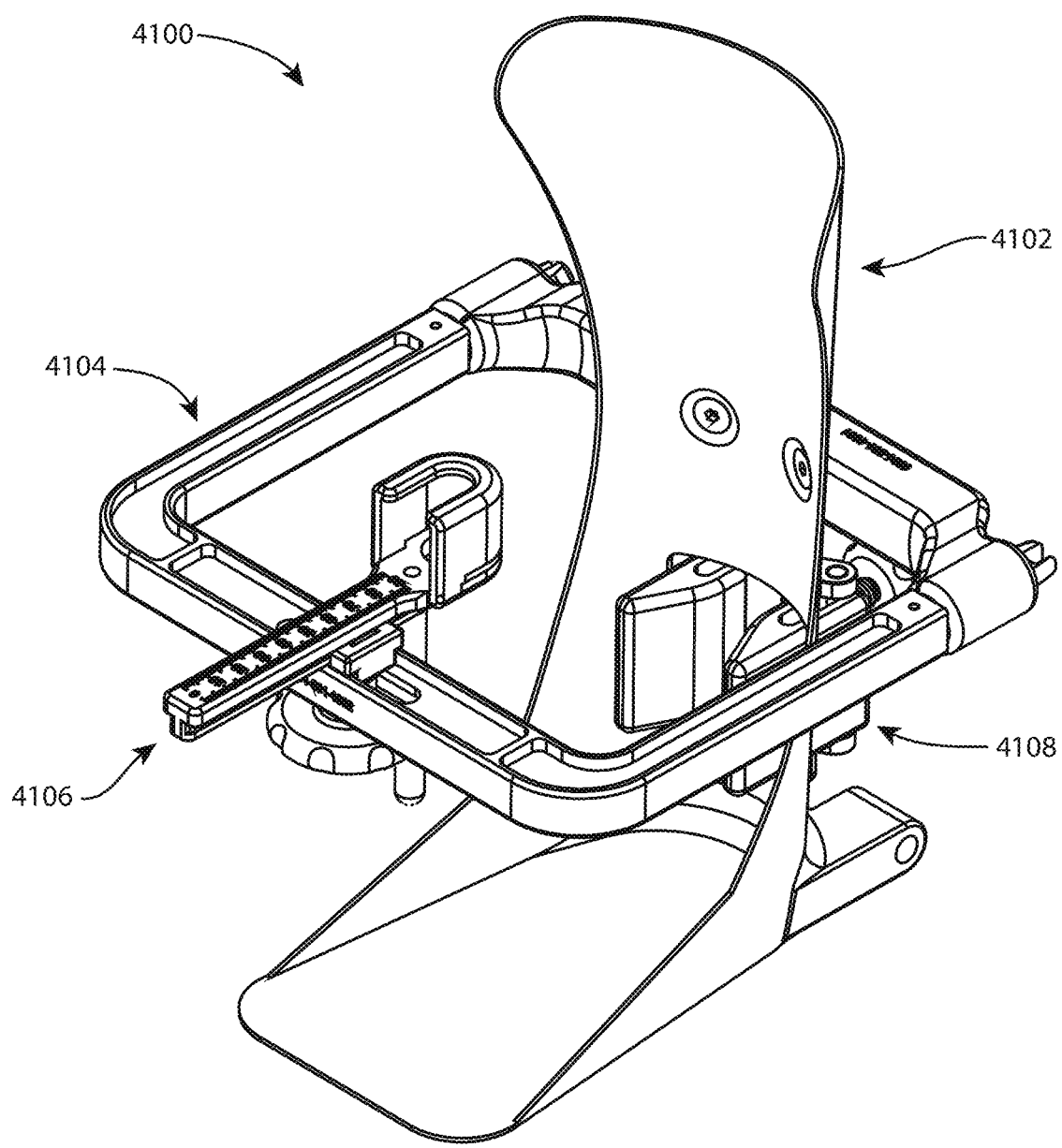
FIG. 51 is an oblique view of the foot holder assembly of FIG. 50 with the bones omitted.

Orienting the bridge 4124 with assembled posts 4126, 4128 and pins 4130, 4132 relative to the bar 4122 as shown in FIG. 51, inserting the post 4126 in the hole 4138, and inserting the post 4128 in the hole 4140. The bridge 4124, posts 4126, 4128, and pins 4130, 4132 may be fixed to the bar 4122 in this step. The posts 4126, 4128 may be inserted into the holes 4138, 4140 simultaneously. Inserting the post 4126 in the hole 4138 and inserting the post 4128 in the hole 4140 may include snapping the lips 4160 into engagement with the posterior side of the bar 4122.

Orienting the target mounting block 4168 relative to the superior side of the bridge 4124 as shown in FIG. 51, inserting the threaded shaft 4178 of the dovetail lock 4170 through the hole 4180, threading the shaft 4178 into the hole 4182 of the thumbscrew 4172 so that the thumbscrew 4172 is adjacent to the inferior side of the bridge 4124, orienting the target 4162 relative to the target mounting block 4168 and dovetail lock 4170 as shown in FIG. 51, sliding the T-rail 4186 into engagement with the T-slot 4184 from a posterior-to-anterior direction so that the cup 4166 is posterior to the target mounting block 4168 and dovetail lock 4170, and tightening the thumbscrew 4172 at least provisionally to retain the target 4162 coupled to the target mounting block 4168 and dovetail lock 4170. The target sub-assembly 4106 together with the bridge 4124 with posts 4126, 4128 and pins 4152, 4154 may be a functional sub-assembly that is removably connectable to the bar 4122.

Orienting the base 4202 relative to the foot receiver 4110 as shown in FIG. 52, inserting a fastener (not shown) through a hole (not shown) in the foot receiver 4110 and into the hole 4236, inserting another fastener (not shown) through another hole (not shown) in the foot receiver 4110 and into the hole 4238. The base 4202 may be fixed to the foot receiver 4110 in this step. The fasteners may be identical to fasteners 4112, 4114. The holes in the foot receiver may be like holes 4116, 4118, with one hole located above the window 4120 and the other hole located below the window.

When the foot holder assembly 4100 is fully assembled, the target sub-assembly 4106 is movable relative to the bridge 4124 along a medial-lateral direction, and the target 4162 is movable relative to the target mounting block 4168, dovetail lock 4170, and thumbscrew 4172 along an anterior-posterior direction established by the T-slot 4184 and T-rail 4186. Tightening the thumbscrew 4172 locks the target 4162 in a position, and loosening the thumbscrew 4172 unlocks the target 4162 so that it can be moved. The Achilles tendon alignment guide sub-assembly is movable relative to the foot receiver 4110 along an anterior-posterior direction between an anterior state for Achilles tendon referencing and a posterior state which relieves pressure on the Achilles tendon 4082.

In a method of use, the foot holder assembly 4100, with the bridge 4124, posts 4126, 4128, pins 4130, 4132, and target sub-assembly 4106 temporarily removed from the bar 4122 and the Achilles tendon alignment guide sub-assembly 4108 in the anterior state, may be coupled to a patient's lower leg and foot by placing the lower leg and foot in the foot receiver 4110 so that the patient's Achilles tendon is received in the notch 4216 of the body 4200, securing the patient's lower leg and foot in the foot receiver 4110, positioning the cup 4166 of the target 4162 in line with the notch 4216, and aligning a tibial extension rod to pass over the medial-lateral center of the proximal tibia with its distal end received in the cup 4166 of the target 4162. The lower leg and foot may be secured in the foot receiver 4110 by wrapping the foot receiver, lower leg, and foot. The method of use may include some or all of these steps, performed in any order.

Figure 49:
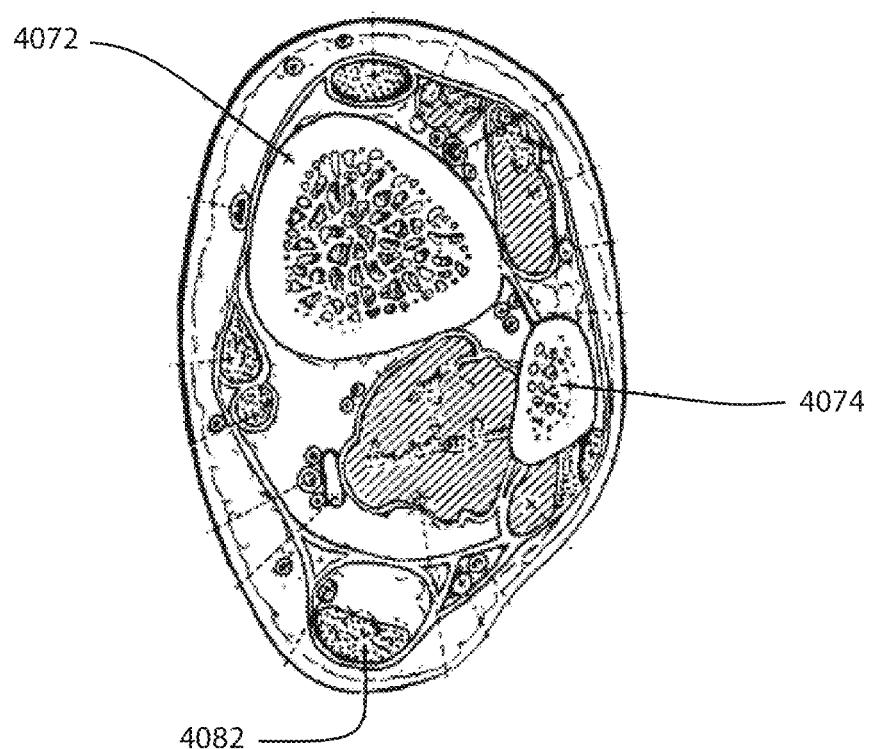
FIG. 49 is a cross-sectional view of a lower leg, taken 2.5 inches above the ankle joint.
Figure 50:
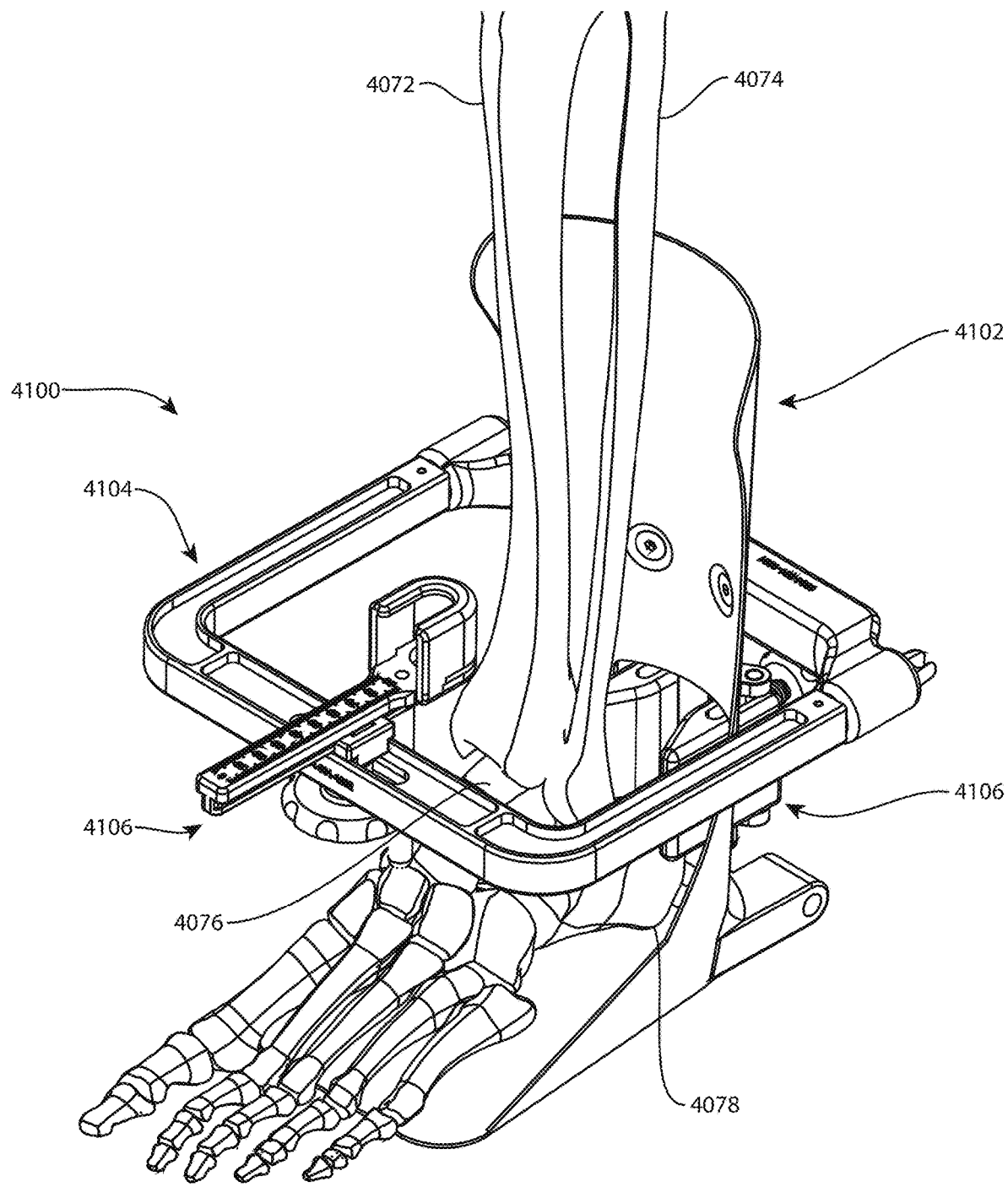
FIG. 50 is an oblique view of another foot holder assembly, showing the bones of the lower leg and foot in position.

Referring to FIG. 49, there is an appreciable anterior-posterior distance between the tibia 4072 and the Achilles tendon 4082. It may be possible for the patient's Achilles tendon 4082 to be properly received in the notch 4216, yet the tibia 4072 could be rotated medially or laterally instead of being aligned over the Achilles tendon. For this reason, the method of use may include an optional step of referencing the patient's foot to ensure that the tibia 4072 is aligned over the Achilles tendon 4082. This step may include placing the lower leg and foot in the foot receiver 4110 with the patient's Achilles tendon received in the notch 4216 of the body 4200, positioning the patient's foot in full dorsiflexion, rotating the lower leg and foot medially or laterally while maintaining full dorsiflexion until the second toe/second metatarsal is in line with the center of the notch 4216, securing the patient's lower leg and foot in the foot receiver 4110, positioning the cup 4166 of the target 4162 in line with the second toe/second metatarsal and notch 4216, and aligning a tibial extension rod to pass over the medial-lateral center of the proximal tibia with its distal end received in the cup 4166 of the target 4162. When the patient's foot is placed in full dorsiflexion, the talus 4076 becomes wedged between the medial and lateral malleoli, which has the effect of straightening the foot relative to the lower leg. The optional hinge or flexible region of the foot receiver 4110 discussed above may be particularly suited to this optional step. The ankle 4070 may be permitted to relax toward its neutral position after the lower leg and foot are secured in the foot receiver 4001 and the target is positioned. This method of use may include some or all of these steps, performed in any order.

Referring to FIGS. 64-71, a multi-pin guide assembly 4300 may include a femoral multi-pin guide 4302, a tibial pin guide 4304, a tube 4306, a tibial alignment rod 4308, and pins 4310, 4312. This single instrument directly references the mechanical axis of the leg and other patient anatomical features to place an array of 5 pins (or holes) that are subsequently referenced by cut guides to make all femoral and tibial resections for total knee arthroplasty. The array of pins or holes is placed in a highly coordinated manner by the single instrument, as opposed to conventional apparatus and methods where pins are placed at different stages of the procedure by different pin guides. This instrument references the mechanical axis of the leg in a manner derived from the apparatus and methods set forth in U.S. patent application Ser. No. 15/630,555, which is incorporated herein in its entirety. More specifically, the multi-pin guide assembly 4300 couples to a base, a handle, a femoral alignment/extension rod, a femoral target, and a tibial target to align the apparatus with the mechanical axis of the leg, as discussed below.

The femoral multi-pin guide 4302 may include an arm 4314 that extends superiorly and anteriorly, terminating in a free end 4316 which may engage a complementary socket of a handle, base, or other component, similar to socket 3624 of femoral pin guide assembly 3500. The arm 4314 may include a pair of tubes 4318, 4320 located on medial and lateral sides of the arm. The tubes 4318, 4320 include holes 4322, 4324 which extend parallel to each other along an anterior-posterior direction. The tubes 4318 may include longitudinal slots 4326, 4328 through the superior side walls of the tubes. The holes 4322, 4324 may receive pin sleeves, such as pin sleeve 3510 discussed above or pin sleeves 1515, 2515 disclosed in U.S. patent application Ser. No. 15/630, 555, which is incorporated herein in its entirety. The holes 4322, 4324 preferably correspond to holes in a distal cut guide, as discussed below. The femoral multi-pin guide 4302 may include a femoral condyle paddle 4330 or plate at the inferior posterior end of the arm 4314. In use, the condyle paddle 4330 is placed in direct contact with a femoral condyle. The condyle paddle 4330 may be a flat plate which extends along medial-lateral and anterior-posterior directions. Therefore, the condyle paddle 4330 may establish a plane that is parallel to the plane established by the holes 4322, 4324. The condyle paddle 4330 shown is for a medial femoral condyle, so it extends medially from the arm 4314. When the illustrated condyle paddle 4330 contacts the medial femoral condyle, the holes 4322, 4324 are positioned so that the distal cut guide will make an 8 mm cut. The same portion of the arm 4314 may include a protrusion 4332 which extends inferiorly from the junction with the condyle paddle 4330. The protrusion 4332 may include anterior and posterior holes 4334, 4336 which extend parallel to each other along a superior-inferior direction which may be parallel with a bone contacting surface of a base when viewed in a lateral view, or which may have a defined orientation relative to the bone contacting surface of the base, for example an acute angle in a lateral view. The direction of the holes 4334, 4336 may be parallel to the mechanical axis of the leg in an anterior view. The anterior hole 4334 may be larger in diameter than the posterior hole. In the example shown, the anterior hole 4334 has a 5 mm diameter and the posterior hole 4336 has a 3.2 mm hole. The holes 4334, 4336, taken together, establish the rotational orientation of the four-in-one cut guide for the anterior, anterior chamfer, posterior chamfer, and posterior resections of the distal femur, as well as the depth and orientation of the anterior resection relative to the distal anterior femoral cortex immediately superior to the trochlear groove. An inferior portion of the protrusion 4332 may include a T-slot 4338 or dovetail slot which extends along an anterior-posterior direction along one medial or lateral side of the protrusion 4332.

The tibial pin guide 4304 may include a T-rail 4340 or dovetail rail which is complementary to the T-slot 4338 of the femoral multi-pin guide 4302. The T-rail may extend along an anterior-posterior direction relative to the femur. A transverse through hole 4342 may extend across the anterior end of the T-rail 4340 to receive the pin 4310. The tibial pin guide 4304 may include a tibial condyle paddle 4344 or plate which protrudes superiorly (relative to the femur) from a posterior portion of the tibial pin guide. In use, the condyle paddle 4344 is placed in direct contact with a tibial condyle or intercondylar area of the tibial plateau. The condyle paddle 4344 may be a flat plate which extends along medial-lateral and superior-inferior directions. Therefore, the condyle paddle 4344 may establish a plane that is perpendicular to the planes established by the holes 4322, 4324 and the femoral condyle paddle 4330. Alternatively, the condyle paddle 4344 may be at an acute angle relative to the planes established by the holes 4322, 4324 and the femoral condyle paddle 4330 in a lateral view. The tibial pin guide 4304 may include a hole 4346 which extends along a superior-inferior direction, parallel to the condyle paddle 4344 in a lateral view and parallel to the mechanical axis of the leg in an anterior view. The hole 4346 is preferably spaced apart from the bone-contacting surface of the condyle paddle 4344 so that when the condyle paddle 4344 contacts the tibial plateau, the hole 4346 is positioned so that a tibial cut guide will make a proximal tibial resection at the desired distance from the posterior femoral resection, to accommodate the planned implant thickness, and in the same rotational alignment as the femoral cut guide. The tibial pin guide 4304 may include anterior and posterior brackets 4348, 4350 which couple to the tube 4306.

The tube 4306 includes a longitudinal through hole 4352. The tube 4306 may include a window 4354 which extends through one side wall in a central portion of the tube. The tube 4306 may include a hole 4356 which extends through one side wall of the tube near the posterior end to receive the pin 4312.

The tibial alignment rod 4308 is shown foreshortened in FIGS. 64-67 due to its long length. The tibial alignment rod 4308 may include a unilateral longitudinal groove 4358 which receives the pin 4312 to prevent rotation of the tibial alignment rod inside the tube 4306. Alternatively, the tube hole 4352 and tibial alignment rod 4308 may have complementary non-circular shapes, such as rectangle, square, or hexagonal. The tibial alignment rod 4308 may include a transverse arm 4360 extending from the distal end of the rod and terminating in a target-engaging finial 4362 which is a sphere in the example shown. The transverse arm 4360 positions the finial 4362 directly in line with the arm 4314 and holes 4334, 4336 of the femoral multi-pin guide 4302 and the hole 4346 of the tibial pin guide 4304 in an anterior-posterior direction relative to the femur.

The multi-pin guide assembly 4300 may be assembled by performing some or all of the following steps in any order.

Figures 64, 65:
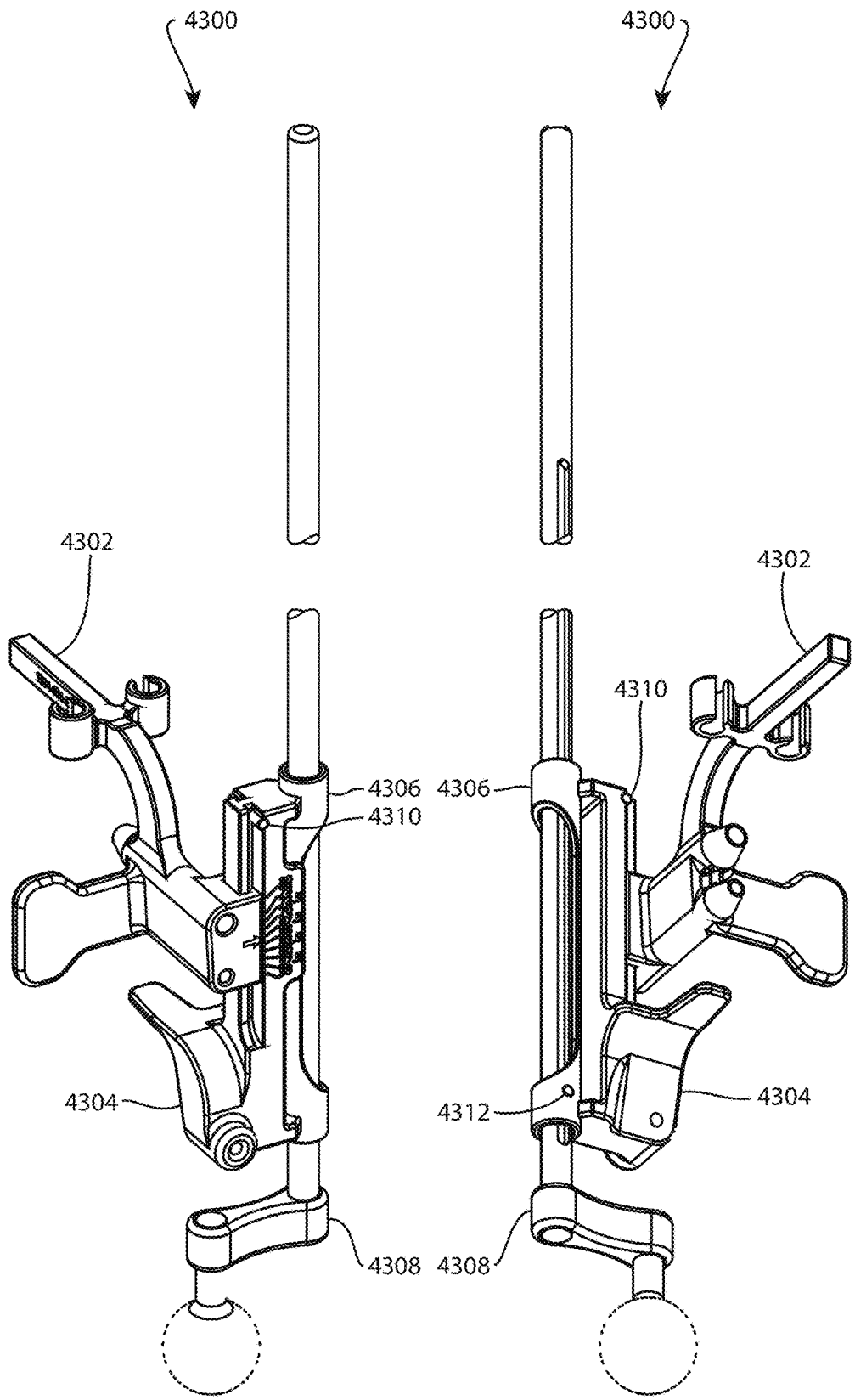
FIG. 64 is an oblique view of a multi-pin guide assembly.
FIG. 65 is another oblique view of the multi-pin guide assembly of FIG. 64 from a different direction.
Figure 66:
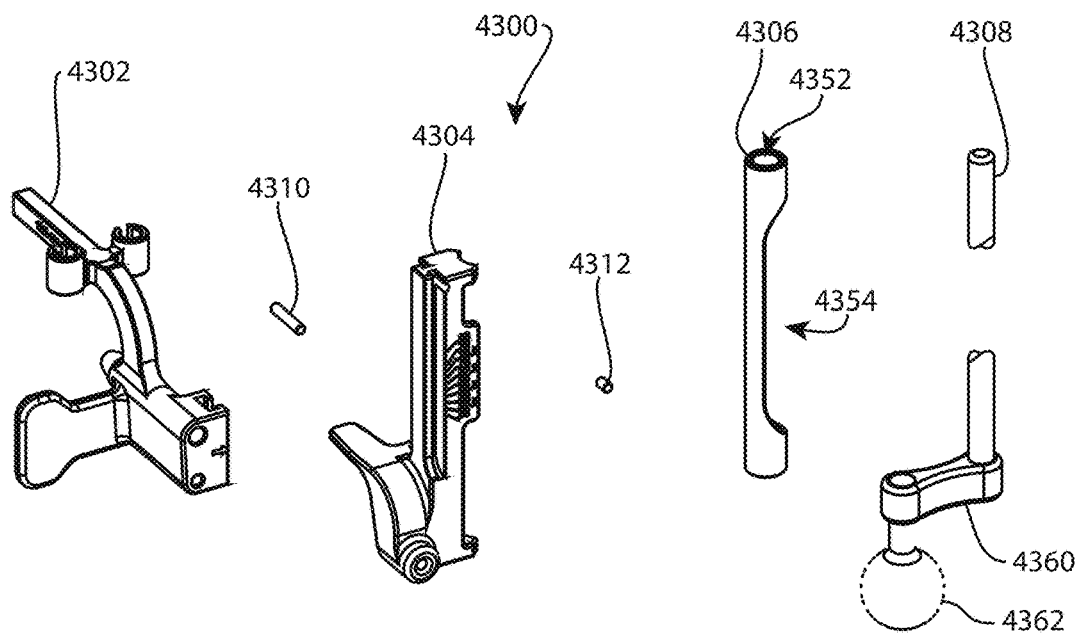
FIG. 66 is an oblique exploded view of the multi-pin guide assembly of FIG. 64.
Figure 67:
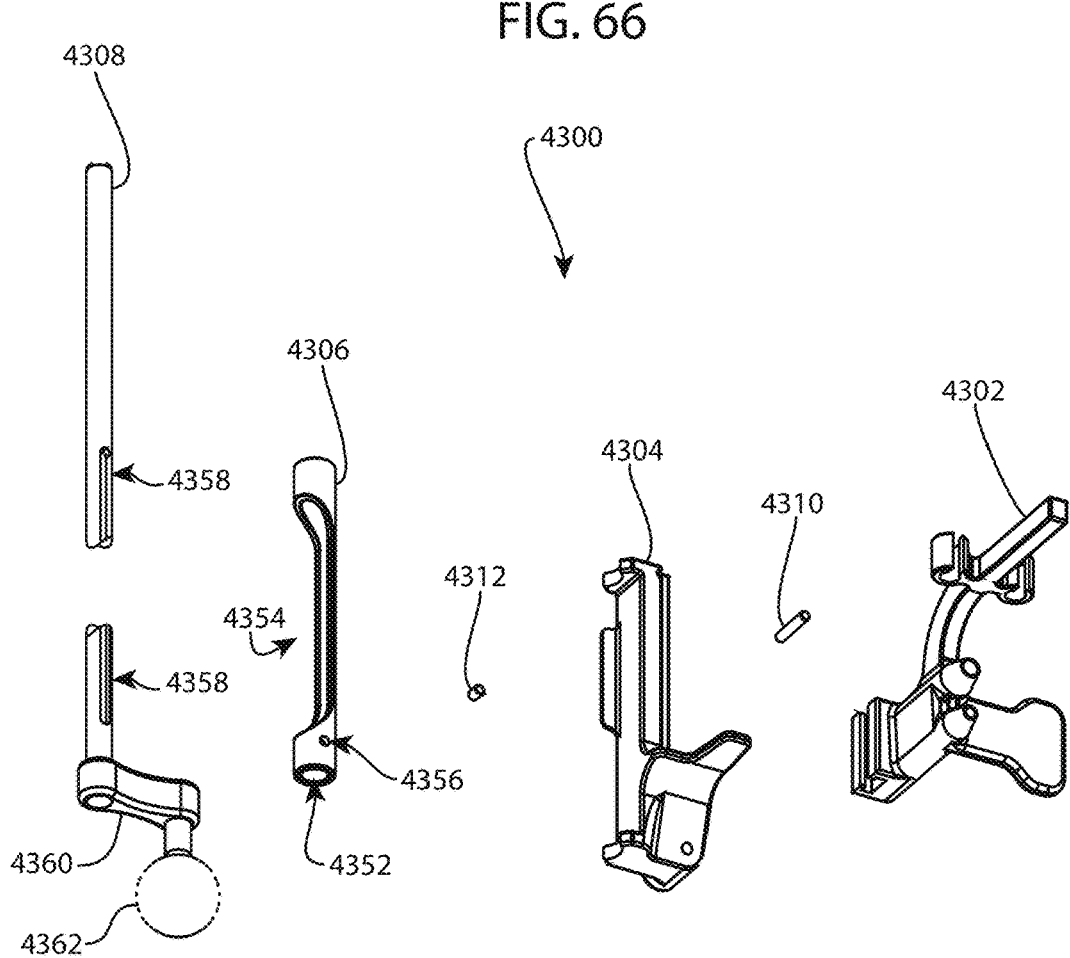
FIG. 67 is another oblique exploded view of the multi-pin guide assembly of FIG. 64 from a different direction.
Figure 68:
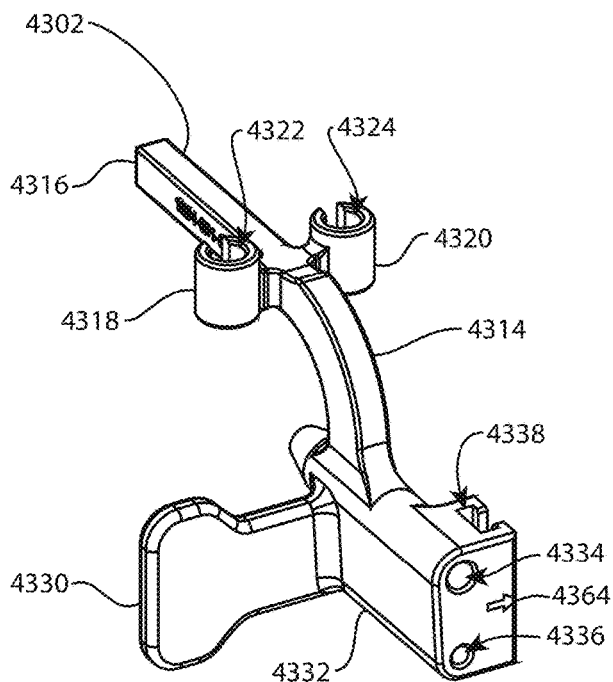
FIG. 68 is an oblique view of a femoral multi-pin guide of the multi-pin guide assembly of FIG. 64.
Figure 69:
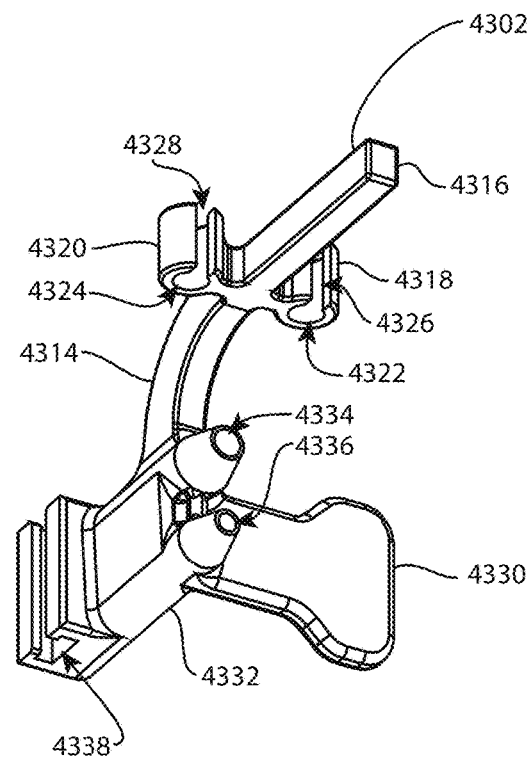
FIG. 69 is another oblique view of the femoral multi-pin guide of FIG. 68 from a different direction.
Figure 70:
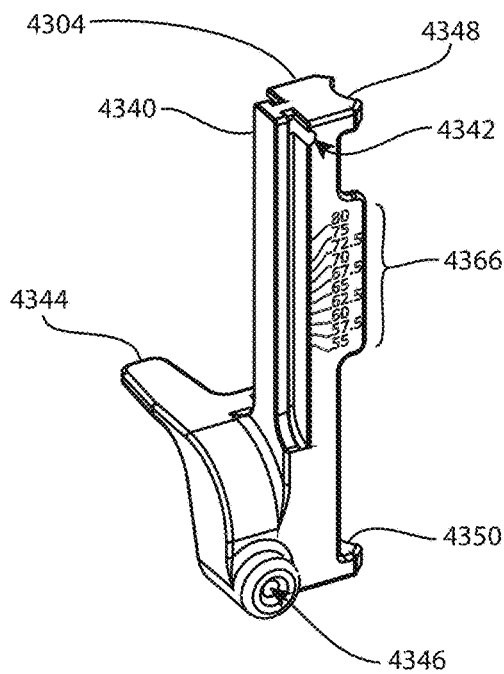
FIG. 70 is an oblique view of a tibial pin guide of the multi-pin guide assembly of FIG. 64.
Figure 71:
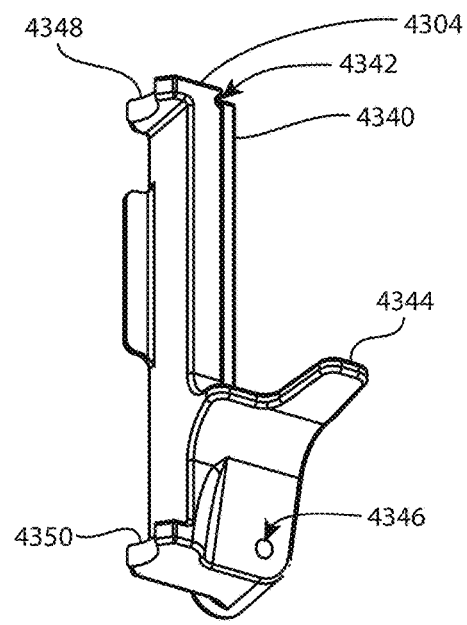
FIG. 71 is another oblique view of the tibial pin guide of FIG. 70 from a different direction.

Orienting the tibial pin guide 4304 relative to the femoral multi-pin guide 4302 as shown in FIG. 64, sliding the T-rail 4340 into the T-slot 4338, positioning the protrusion 4332 adjacent to the tibial condyle paddle 4344, and fixing the pin 4310 in the hole 4342 to make the tibial pin guide 4304 captive to the femoral multi-pin guide 4302.

Orienting the tube 4306 relative to the tibial pin guide 4304 as shown in FIG. 65 and fixing the tube to the brackets 4348, 4350.

Orienting the tibial alignment rod 4308 relative to the tube 4306 as shown in FIG. 65, sliding the rod into the hole 4352, inserting the pin 4312 through the hole 4356 and into the groove 4358, and fixing the pin 4312 in the hole 4356.

When the multi-pin guide assembly 4300 is fully assembled, the tibial pin guide 4304 is movable relative to the femoral multi-pin guide 4302 along an anterior-posterior direction (relative to the femur) established by the T-rail 4340 in the T-slot 4338. Unintentional disassembly is prevented by the pin 4310 extending across the T-rail 4340. Indicia 4364, 4366 on the femoral multi-pin guide 4302 and the tibial pin guide 4304 indicate to the user the femoral component size for a particular patient. The tibial alignment rod 4308 is movable relative to the tibial pin guide 4304 along an anterior-posterior direction (relative to the femur) established by the rod in the hole 4352.

Figure 72:
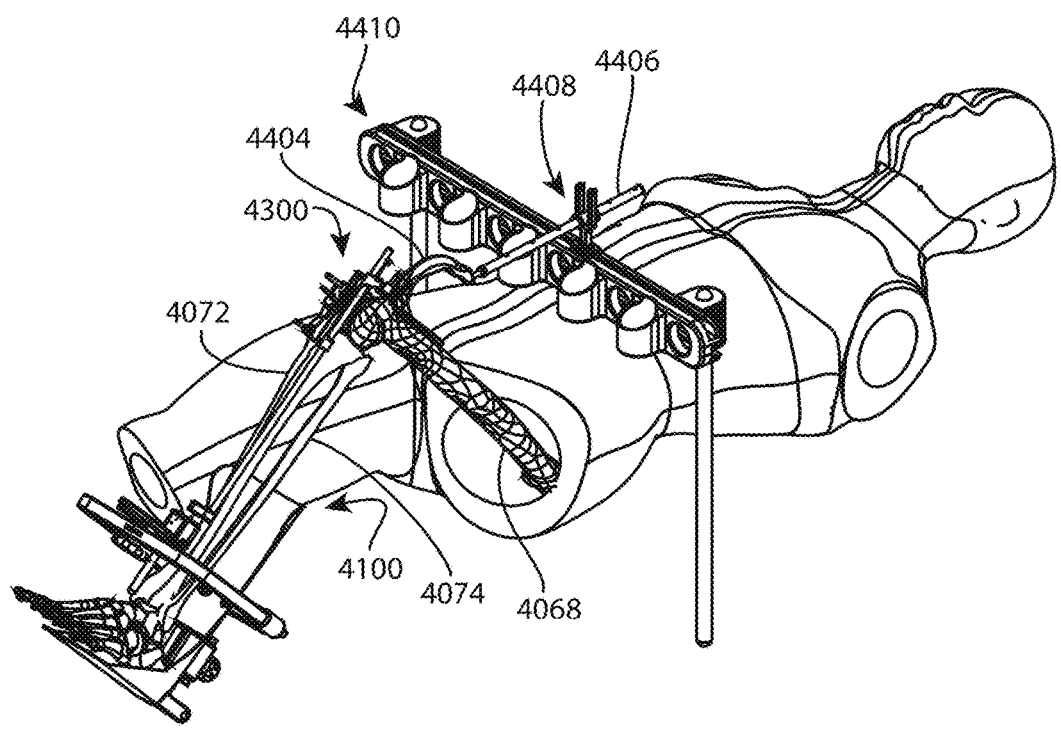
FIG. 72 is an oblique view of the multi-pin guide assembly of FIG. 64 coupled to a femur and tibia by pins, and coupled to a body, a base, a handle, a femoral extension rod, a femoral target assembly, a femoral support arm assembly, and the foot holder assembly of FIG. 50, with selected portions of soft tissues shown for context.
Figure 73:
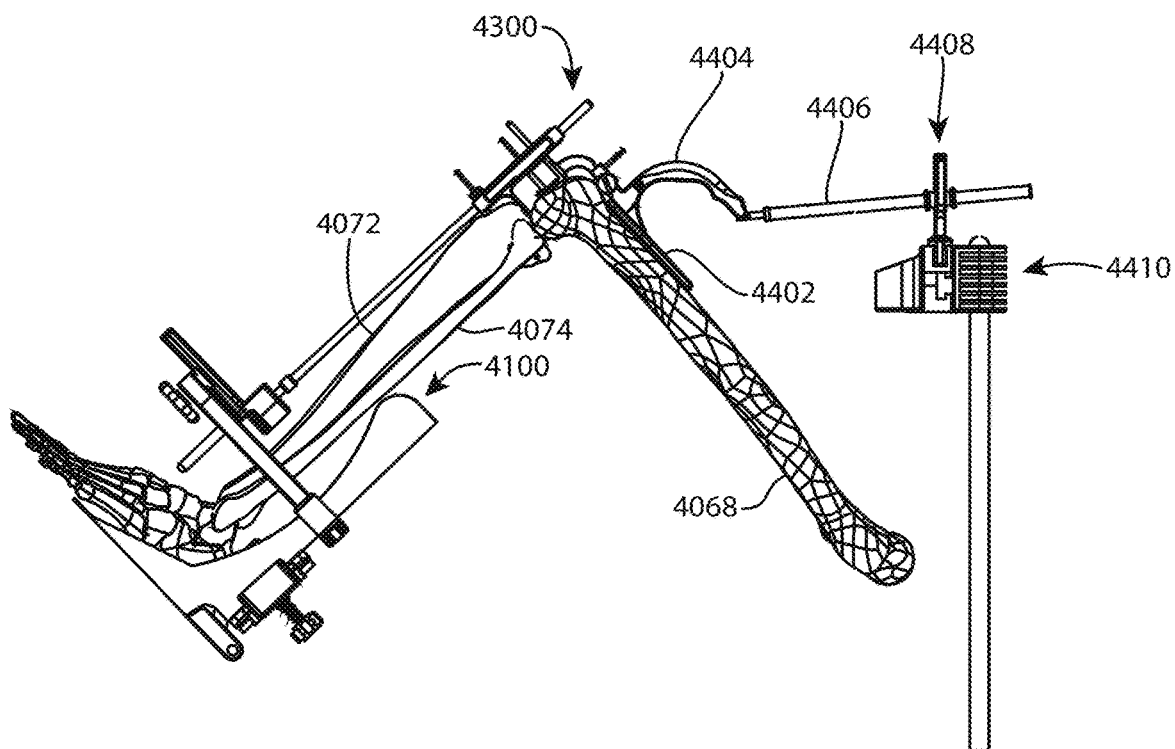
FIG. 73 is a lateral view of the multi-pin guide assembly, femur, tibia, pins, body, base, handle, femoral extension rod, femoral target assembly, femoral support arm assembly, and foot holder assembly of FIG. 72, soft tissues omitted for clarity.
Figure 74A:
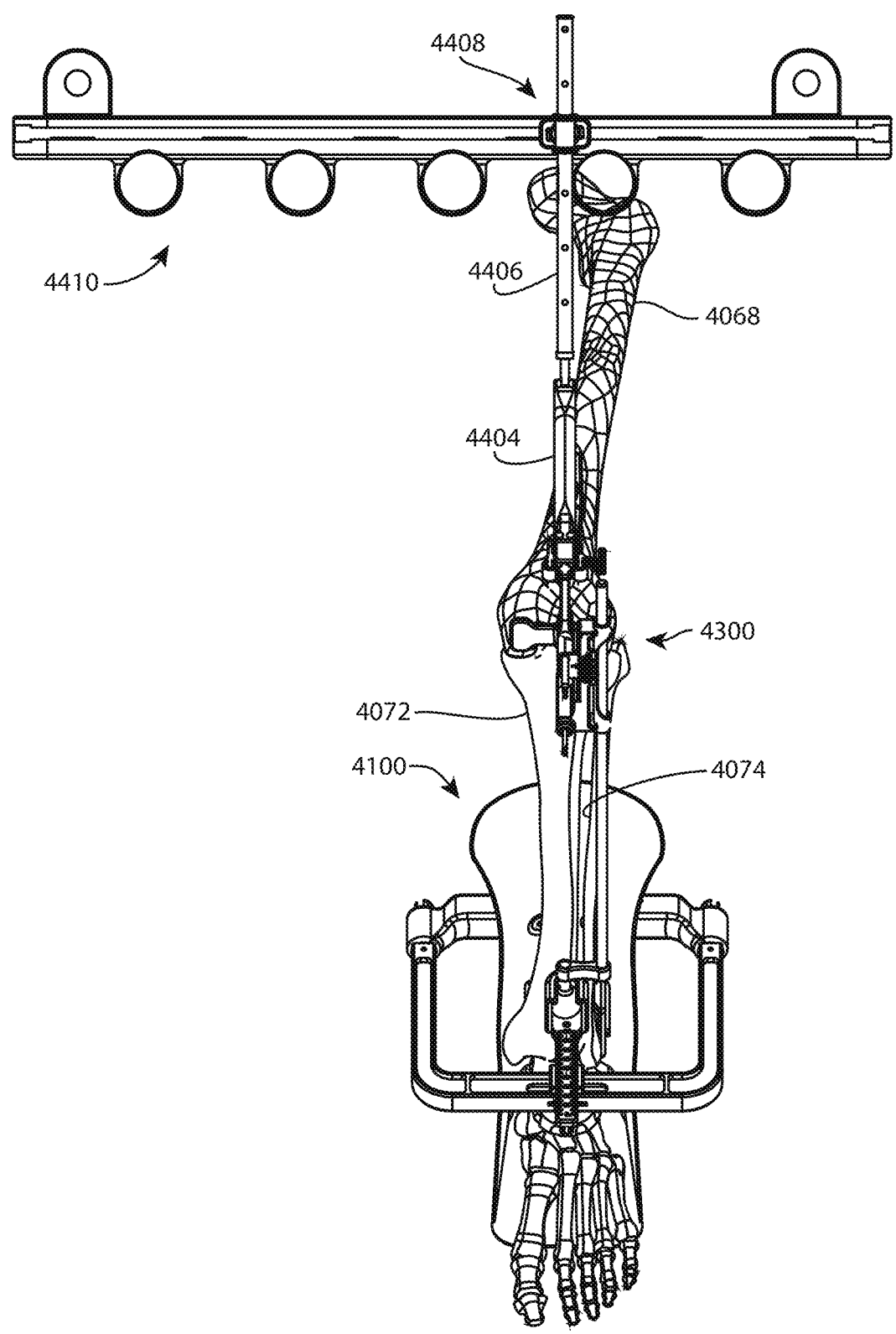
FIG. 74A is an anterior or top view of the multi-pin guide assembly, femur, tibia, pins, body, base, handle, femoral extension rod, femoral target assembly, femoral support arm assembly, and foot holder assembly of FIG. 73.
Figure 74B:
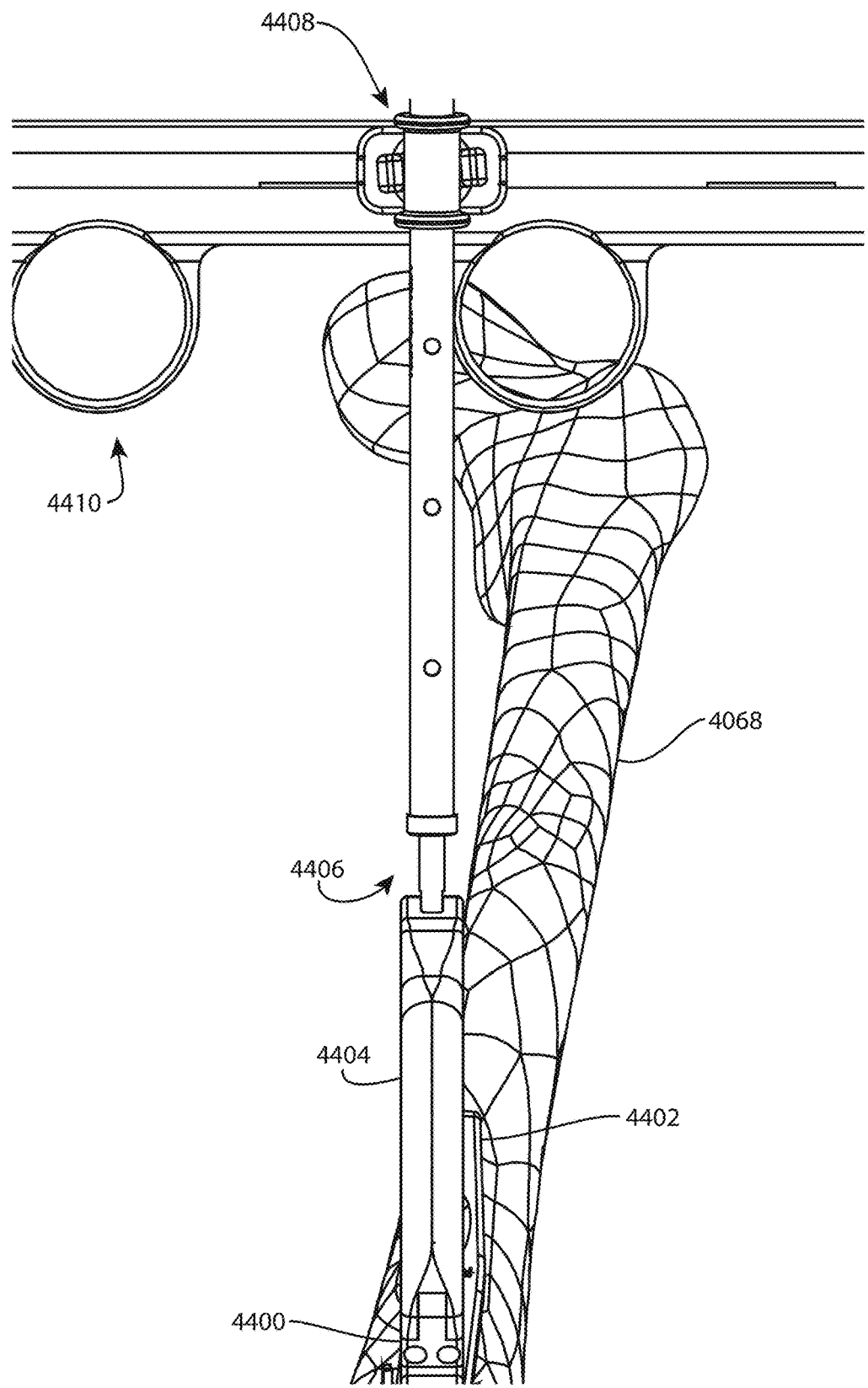
FIG. 74B is an enlarged detail view of the of the femur, body, base, handle, femoral extension rod, femoral target assembly, and femoral support arm assembly of FIG. of FIG. 74A in the vicinity of the femoral head.
Figure 74C:
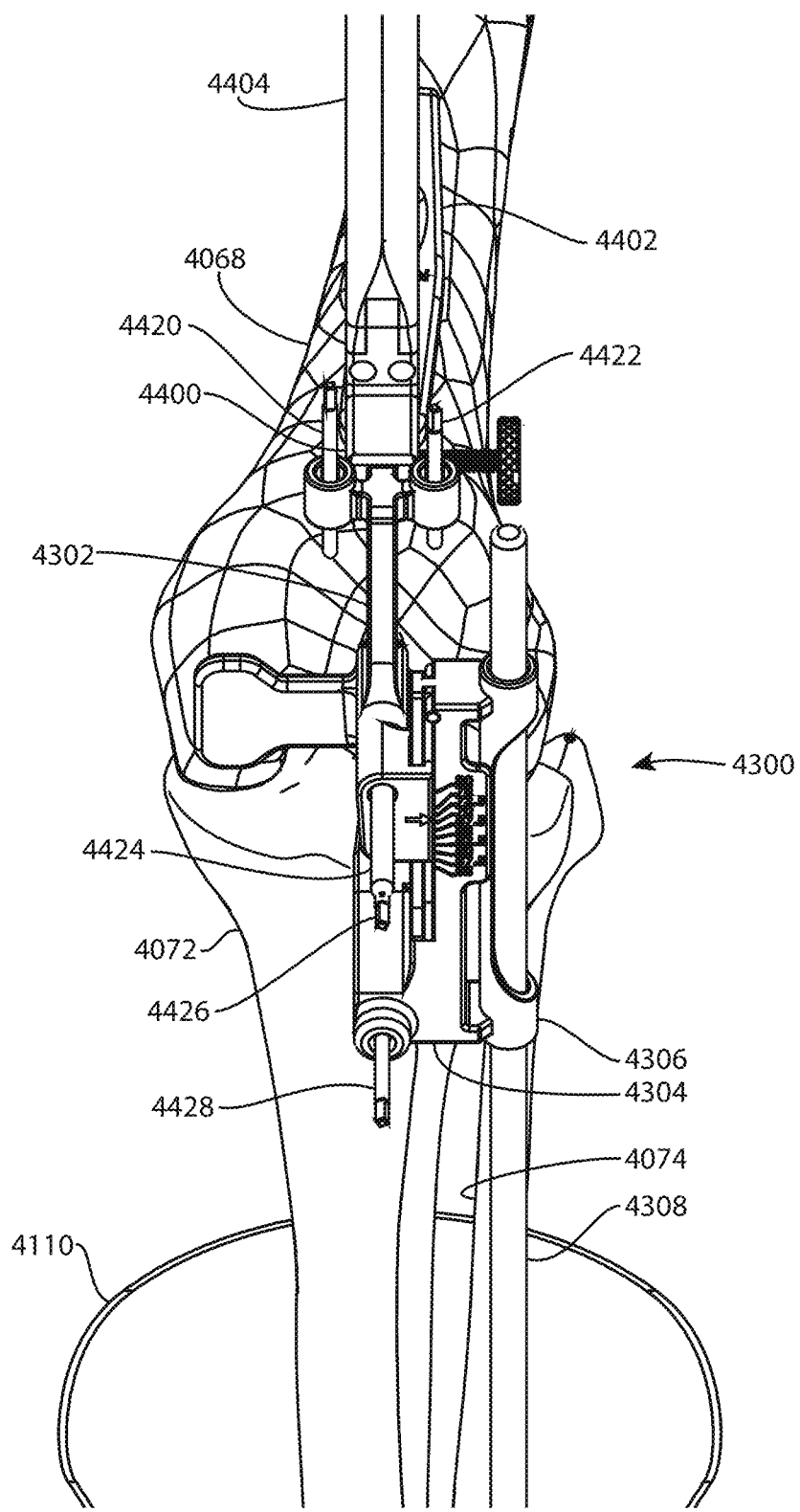
FIG. 74C is an enlarged detail view of the multi-pin guide assembly, femur, tibia, pins, body, base, handle, and foot holder assembly of FIG. 74A in the vicinity of the knee joint.
Figure 74D:
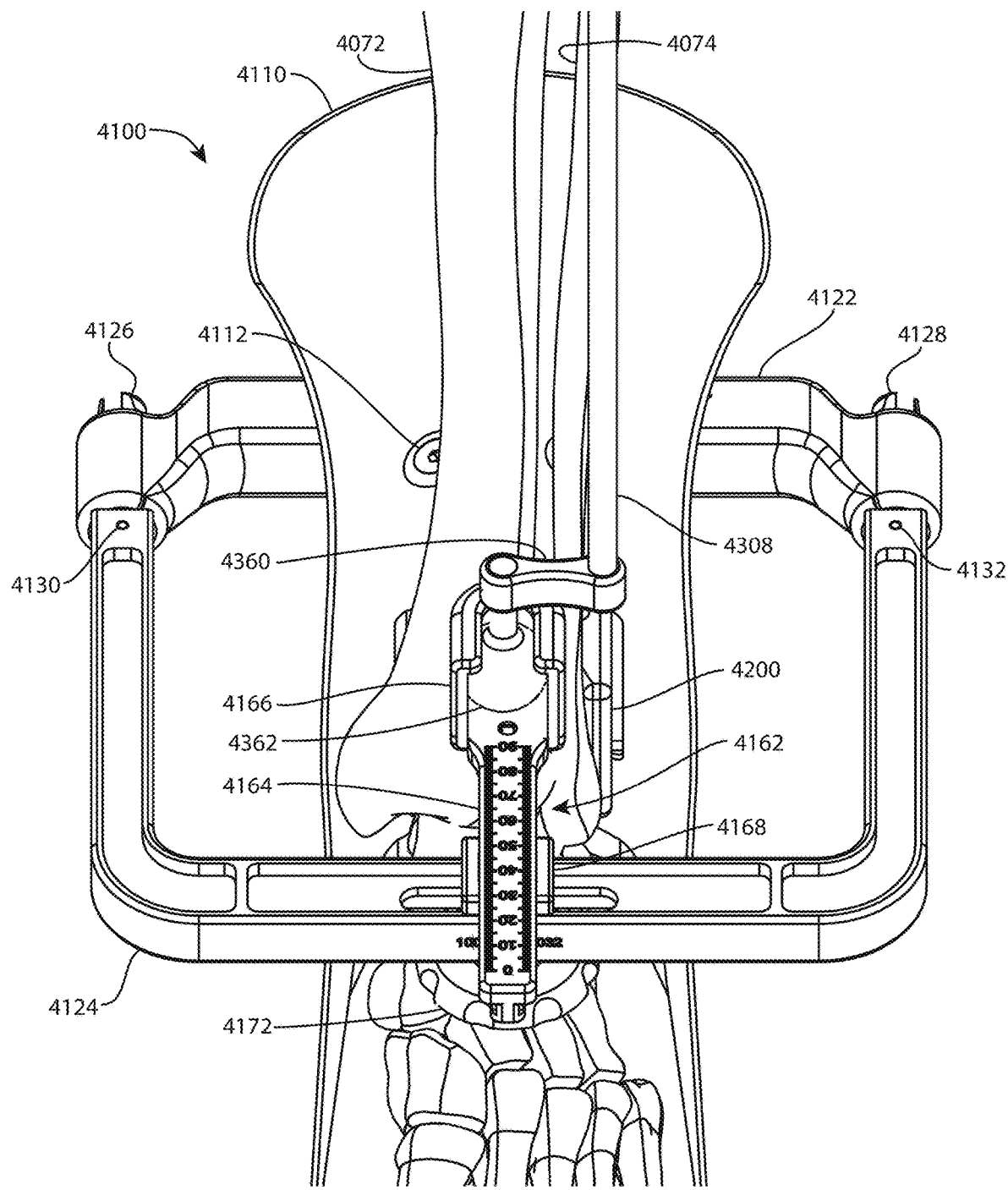
FIG. 74D is an enlarged detail view of the multi-pin guide assembly, tibia, and foot holder assembly of FIG. 74A in the vicinity of the ankle joint.
Figure 75:
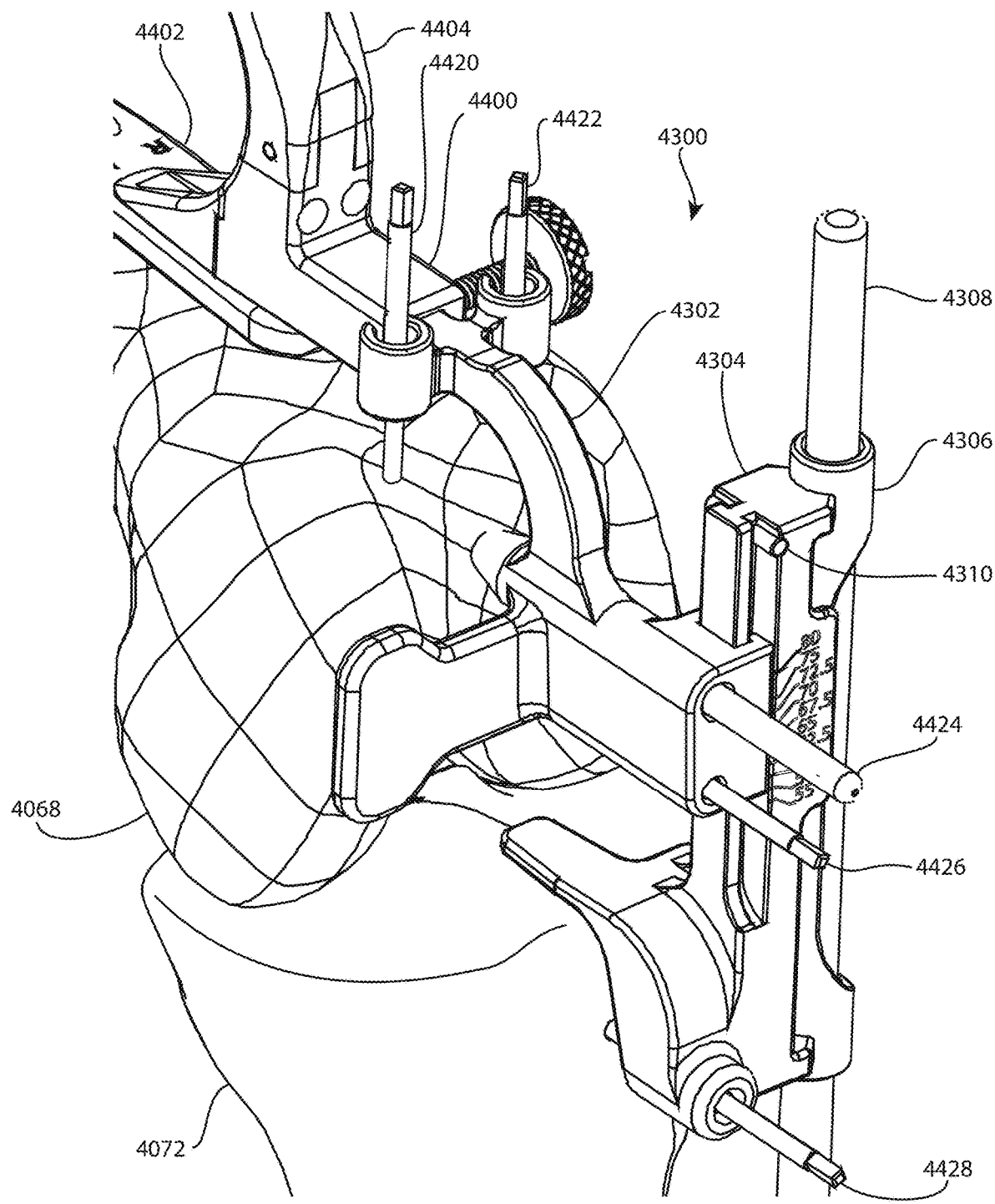
FIG. 75 is an oblique detail view of the multi-pin guide assembly, femur, tibia, pins, body, base, and handle of FIG. 73 from an anterior-inferior-medial direction.

FIGS. 72-75 show the multi-pin guide assembly 4300 coupled to a body 4400, a base 4402, a handle 4404, a femoral extension rod 4406, a femoral target assembly 4408, a femoral support arm assembly 4410, and the foot holder assembly 4100. A femur 4068, tibia 4072, and fibula 4074 are shown, along with bones of the foot. The knee is in 90 degrees of flexion. FIG. 72 shows selected regions of soft tissue of the head, torso, and right thigh for context.

The body 4400, base 4402, and handle 4404 may be comparable to portions of the femoral pin guide assembly 3500 or the trunnion 12, base 10, handle 26; base 302, handle 304; femoral riser 504, base 502; base 1502, handle 1516; and base 2502, handle 2516 disclosed in U.S. patent application Ser. No. 15/630,555. The body 4400, base 4402, and handle 4404 may be exchanged with these alternative apparatus.

The femoral extension rod 4406 may be similar to or identical to or exchanged with femoral extension rod 3524, or alignment rod 156 or femoral extension rods 306, 506, 1506, 2506 disclosed in U.S. patent application Ser. No. 15/630,555.

The femoral target assembly 4408 may be similar to or identical to or exchanged with target assemblies 818, 1818, 2818 disclosed in U.S. patent application Ser. No. 15/630,555.

The femoral support arm assembly 4410 may be similar to or identical to or exchanged with femoral support arm assemblies 786, 1786, 2786 disclosed in U.S. patent application Ser. No. 15/630,555. However, the assembly 4410 includes a bar having various openings and features conducive to organizing and storing surgical items.

The foot holder assembly 4100 may be similar to or identical to or exchanged with the foot holder assembly 3950 or foot holder assemblies 870, 1870, 2870 disclosed in U.S. patent application Ser. No. 15/630,555.

Referring to FIGS. 72-78B, a method of using the multi-pin guide assembly 4300 may include some or all of the following steps in any order.

Coupling the femoral multi-pin guide 4302 to a base and a femoral extension rod. This step may include inserting the free end 4316 of the femoral multi-pin guide arm 4314 into a socket like socket 3624 of femoral pin guide assembly 3500 and tightening a thumbscrew.

Aligning the femoral extension rod over the center of the femoral head and over the medial-lateral center of the distal femur. This step may include coupling the femoral extension rod to a femoral target which was previously centered relative to the femoral head.

Coupling the finial 4362 to a tibial target which was previously centered relative to the distal tibia or medial-lateral center of the ankle. The knee may be in 90 degrees of flexion for this step and the following steps.

Centering the proximal tibia relative to the hole 4346 of the tibial pin guide 4304 along a medial-lateral direction.

Contacting a distal femoral condyle with the condyle paddle 4330, contacting the tibial plateau with the condyle paddle 4344, and reading the femoral component size from the indicia 4364, 4366.

While maintaining the alignments of the preceding steps, driving pins 4420, 4422 through holes 4322, 4324 of the femoral multi-pin guide 4302; driving pins 4424, 4426 through holes 4334, 4336 of the femoral multi-pin guide 4302; and driving a pin 4428 through hole 4346 of the tibial pin guide 4304. This step may be preceded by a step of inserting pin sleeves in holes 4322, 4324 before driving pins 4420, 4422 through the holes.

Figure 76:
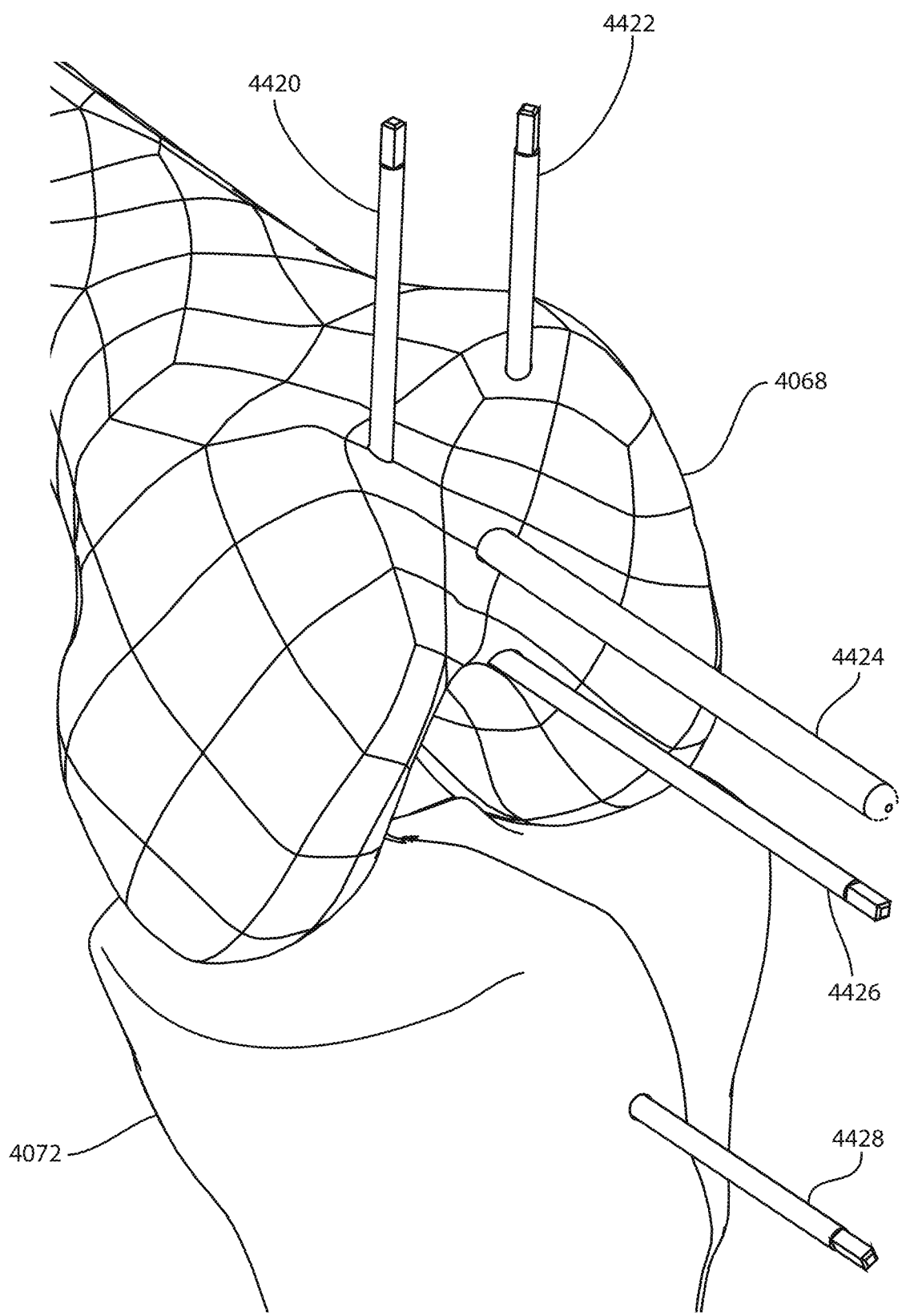
FIG. 76 is an oblique detail view of the femur, tibia, and pins of FIG. 75 after removing the multi-pin guide assembly, body, base, and handle.

Optionally removing the pin sleeves from holes 4322, 4324, if used. Optionally disengaging the femoral extension rod from the femoral target, if used. Disengaging the tibial alignment rod 4308 from the tibial target. Disengaging the femoral alignment rod, base, and multi-pin guide assembly 4300 from the operative site by pulling the apparatus along the direction established by the pins 4424, 4426, 4428. Preferably, the pins 4424, 4426, 4428 and their corresponding holes 4334, 4336, 4346 are mutually parallel. The pins 4420, 4422 exit holes 4322, 4324 via slots 4326, 4328. FIG. 76 illustrates the femur 4068 and tibia 4072 after this step is complete.

Figure 77:
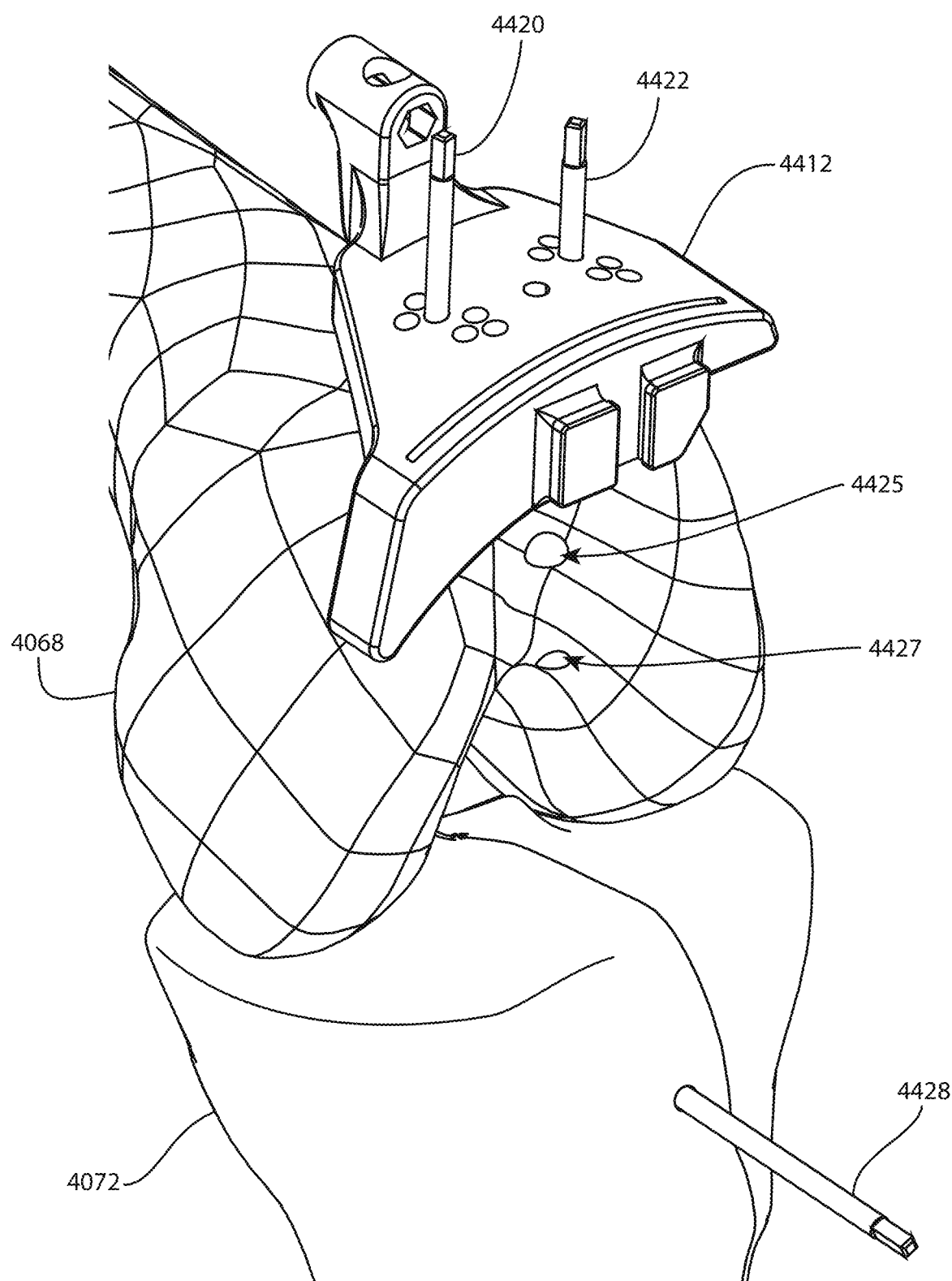
FIG. 77 is an oblique detail view of the femur, tibia, and selected pins of FIG. 76, with a distal femoral cut guide coupled to anterior distal femoral pins.

Removing pins 4424, 4426 and coupling a distal femoral cut guide 4412 to the anterior distal femur using pins 4420, 4422. Holes 4425, 4427 remain in the femur 4068 after pins 4424, 4426 are removed. FIG. 77 illustrates the femur 4068 and tibia 4072 after this step is complete.

Figure 78A:
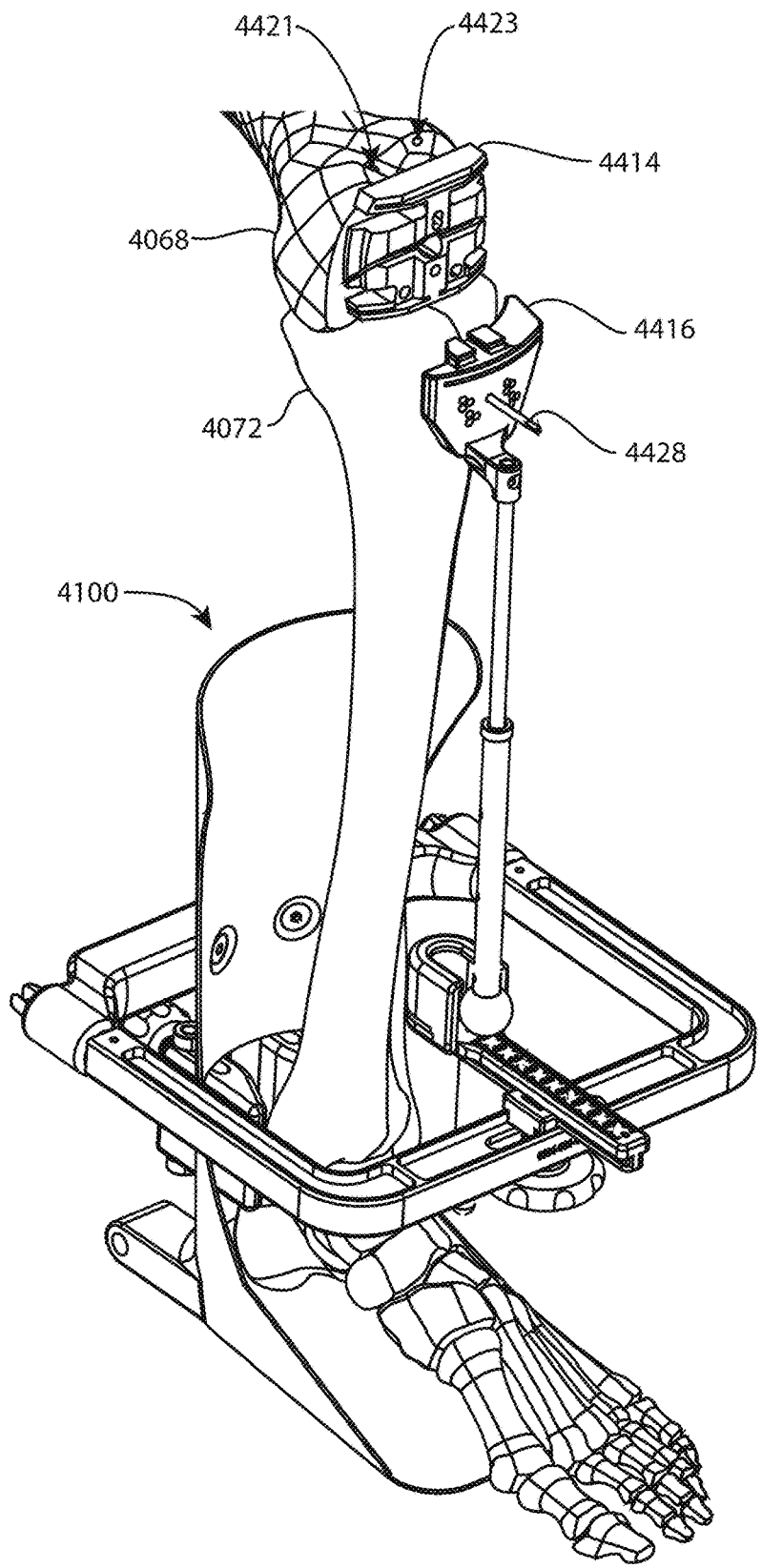
FIG. 78A is an oblique detail view of the femur, tibia, and selected pins of FIG. 76, after making a distal femoral resection and removing the distal femoral cut guide and anterior distal femoral pins, and after attaching a femoral four-in-one cut guide and a tibial cut guide coupled to a tibial extension rod, coupled to the foot holder assembly of FIG. 50.
Figure 78B:
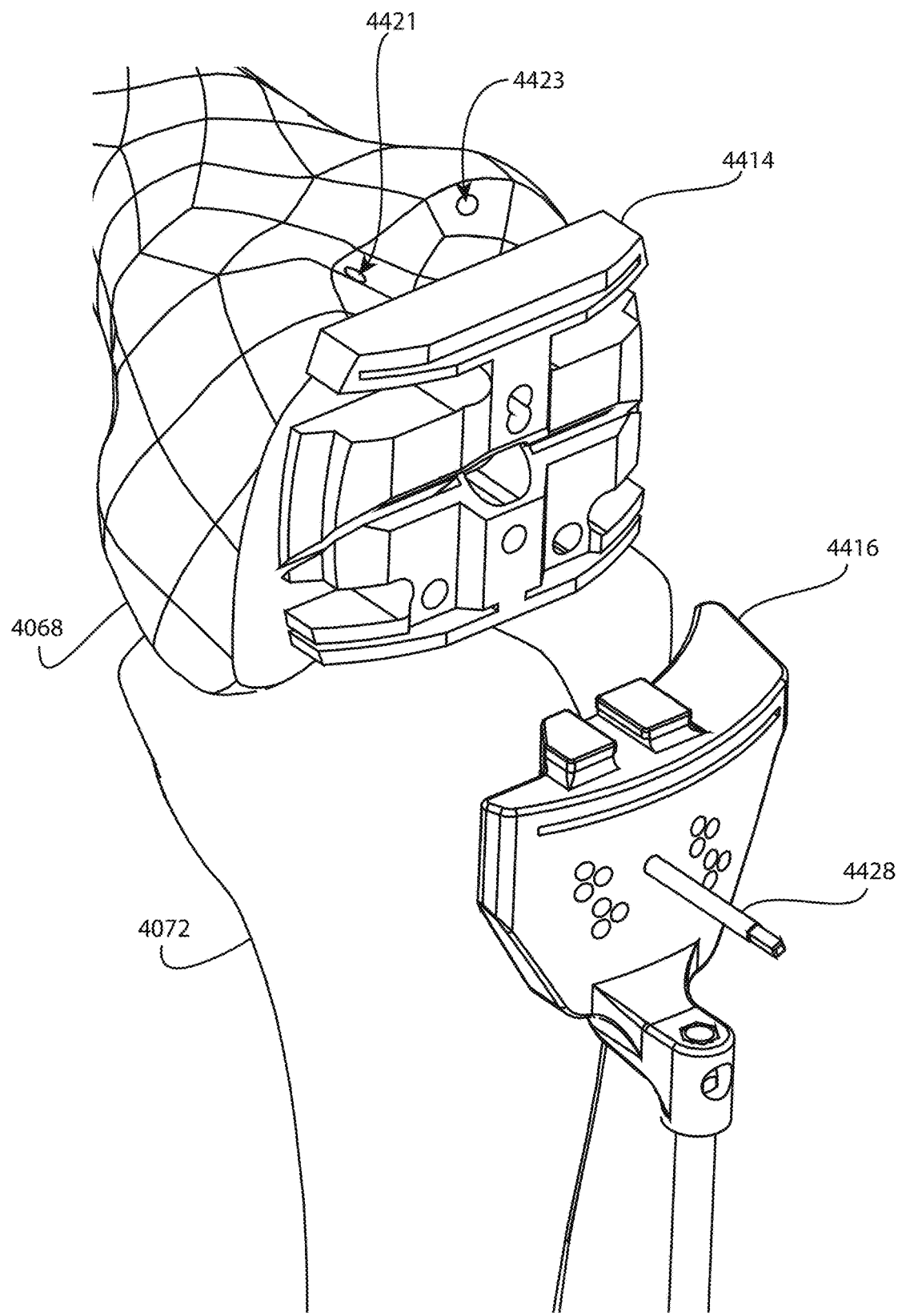
FIG. 78B is an enlarged oblique detail view of the femur, tibia, femoral four-in-one cut guide, tibial pin, tibial cut guide, and tibial extension rod of FIG. 78A.

Making a distal femoral resection through the distal femoral cut guide 4412, removing pins 4420, 4422, coupling a femoral four-in-one cut guide 4414 to the distal femoral resection, coupling a tibial cut guide 4416 to the proximal anterior tibia using pin 4428, and coupling the finial of a tibial extension rod to a tibial target which was previously centered relative to the distal tibia or medial-lateral center of the ankle. Holes 4421, 4423 remain in the femur 4068 after pins 4420, 4422 are removed. Coupling the femoral four-in-one cut guide 4414 to the distal femoral resection may include inserting two posts (not shown) on the bone-facing side of the cut guide 4414 into the holes 4425, 4427. This arrangement sets the rotation of the femoral four-in-one cut guide 4414. FIG. 78A illustrates the completion of this step and FIG. 78B provides a closeup view of the knee.

Additional steps may be performed, such as making the anterior, anterior chamfer, posterior, and posterior chamfer cuts and the proximal tibial cut, and removing the cut guides 4414, 4416 and pin 4428.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A four-in-one femoral cut guide system for knee arthroplasty, comprising:
   a rail extending along an anterior-posterior direction;
   an anterior cut guide with an anterior resection saw slot configured to guide a saw to make an anterior resection in a distal femur;

an anterior chamfer guide with an anterior chamfer saw slot configured to guide a saw to make an anterior chamfer resection in the distal femur;
a posterior chamfer guide with a posterior chamfer saw slot configured to guide a saw to make a posterior chamfer resection in the distal femur;
a posterior cut guide with a posterior resection saw slot configured to guide a saw to make a posterior resection in the distal femur; and
a locking element movably retained by the rail such that the locking element comprises an unlocked configuration in which the anterior cut guide, anterior chamfer guide, and posterior chamfer guide are slidably coupled to and independently movable along the rail relative to the posterior cut guide along an anterior-posterior direction, and a locked configuration in which the anterior cut guide, anterior chamfer guide, posterior chamfer guide, and posterior cut guide are all fixed relative to each other along the rail.

2. The system of claim 1, further comprising:
a first spacer configured to engage with the four-in-one cut guide, wherein the first spacer comprises a spacer body, an anterior arm comprising a first anterior-posterior thickness, a middle arm comprising a second anterior-posterior thickness, and a posterior arm comprising a third anterior-posterior thickness, wherein the anterior, middle, and posterior arms are coupled to the spacer body;
wherein when the first spacer is engaged with the four-in-one cut guide, the anterior arm extends between the anterior cut guide and the anterior chamfer guide, the middle arm extends between the anterior chamfer guide and the posterior chamfer guide, and the posterior arm extends between the posterior chamfer guide and the posterior cut guide.

3. The system of claim 1, further comprising:
a spacer configured to engage the four-in-one cut guide, wherein the spacer comprises first, second, third, and fourth end effectors coupled to a spacer body, wherein the second end effector is posterior to the first end effector, wherein the third end effector is posterior to the second end effector, wherein the fourth end effector is posterior to the third end effector;
wherein when the spacer is engaged with the four-in-one cut guide, the first end effector couples to the anterior cut guide, the second end effector couples to the anterior chamfer guide, the third end effector couples to the posterior chamfer guide, and the fourth end effector couples to the posterior cut guide.

4. The system of claim 2, wherein:
when the first spacer engages the four-in-one cut guide, the anterior cut guide, the anterior chamfer guide, the posterior chamfer guide, and the posterior cut guide are properly positioned, relative to each other, to guide resections of the distal femur to prepare the distal femur to receive a first femoral implant;
the system further comprises a second spacer, sized differently from the first spacer, and configured to engage the four-in-one cut guide; and
when the second spacer engages the four-in-one cut guide, the anterior cut guide, the anterior chamfer guide, the posterior chamfer guide, and the posterior cut guide are properly positioned, relative to each other, to guide resections of the distal femur to prepare the distal femur to receive a second femoral implant sized differently from the first femoral implant.

5. The system of claim 1, wherein the locking element is rotatable, within the rail, between:
an unlocked position that provides the unlocked configuration; and
a locked position that provides the locked configuration.

6. The system of claim 5, wherein:
the locking element comprises a generally cylindrical shape with teeth protruding therefrom; and
at least three of the anterior cut guide, the anterior chamfer guide, the posterior chamfer guide, and the posterior cut guide comprise teeth that mesh with the teeth of the locking element when the locking element is in the locked position, but not when the locking element is in the unlocked position.

7. The system of claim 6, wherein:
the teeth of the locking element extend only partway around a circumference of the generally cylindrical shape such that, when the locking element is in the unlocked position, the teeth of the locking element are not aligned with the teeth of the anterior cut guide, the anterior chamfer guide, the posterior chamfer guide, and/or the posterior cut guide; and
in the locked position, the locking element has been rotated 90 degrees from the unlocked position.

8. The system of claim 1, wherein the posterior cut guide is rigidly secured to the rail.

9. A four-in-one femoral cut guide system for knee arthroplasty, comprising:
a rail extending along an anterior-posterior direction;
an anterior cut guide with an anterior resection saw slot configured to guide a saw to make an anterior resection in a distal femur;
an anterior chamfer guide with an anterior chamfer saw slot configured to guide a saw to make an anterior chamfer resection in the distal femur;
a posterior chamfer guide with a posterior chamfer saw slot configured to guide a saw to make a posterior chamfer resection in the distal femur;
a posterior cut guide with a posterior resection saw slot configured to guide a saw to make a posterior resection in the distal femur; and
a locking element movably retained by the rail such that the locking element comprises an unlocked position and a locked position, the locking element comprising teeth;
wherein:
in the unlocked position, at least three of the anterior cut guide, the anterior chamfer guide, the posterior chamfer guide, and the posterior cut guide are slidably coupled to and independently movable along the rail;
in the locked position, the anterior cut guide, the anterior chamfer guide, the posterior chamfer guide, and the posterior cut guide are not movable along the rail; and
at least three of the anterior cut guide, the anterior chamfer guide, the posterior chamfer guide, and the posterior cut guide comprise teeth that mesh with the teeth of the locking element when the locking element is in the locked position, but not when the locking element is in the unlocked position.

10. The system of claim 9, further comprising:
a first spacer configured to engage with the four-in-one cut guide, wherein the first spacer comprises a spacer body, an anterior arm comprising a first anterior-posterior thickness, a middle arm comprising a second anterior-posterior thickness, and a posterior arm comprising a third anterior-posterior thickness, wherein the anterior, middle, and posterior arms are coupled to the spacer body;

wherein when the first spacer is engaged with the four-in-one cut guide, the anterior arm extends between the anterior cut guide and the anterior chamfer guide, the middle arm extends between the anterior chamfer guide and the posterior chamfer guide, and the posterior arm extends between the posterior chamfer guide and the posterior cut guide.

11. The system of claim 10, wherein:

when the first spacer engages the four-in-one cut guide, the anterior cut guide, the anterior chamfer guide, the posterior chamfer guide, and the posterior cut guide are properly positioned, relative to each other, to guide resections of the distal femur to prepare the distal femur to receive a first femoral implant;

the system further comprises a second spacer, sized differently from the first spacer, and configured to engage the four-in-one cut guide; and when the second spacer engages the four-in-one cut guide, the anterior cut guide, the anterior chamfer guide, the posterior chamfer guide, and the posterior cut guide are properly positioned, relative to each other, to guide resections of the distal femur to prepare the distal femur to receive a second femoral implant sized differently from the first femoral implant.

12. The system of claim 9, wherein:

the locking element comprises a generally cylindrical shape from which the teeth of the locking element protrude.

13. The system of claim 12, wherein:

the teeth of the locking element extend only partway around a circumference of the generally cylindrical shape such that, when the locking element is in the unlocked position, the teeth of the locking element are not aligned with the teeth of the anterior cut guide, the anterior chamfer guide, the posterior chamfer guide, and/or the posterior cut guide; and in the locked position, the locking element has been rotated 90 degrees from the unlocked position.

14. The system of claim 9, wherein the posterior cut guide is rigidly secured to the rail.

15. A four-in-one femoral cut guide system for knee arthroplasty, comprising:

a rail extending along an anterior-posterior direction;

an anterior cut guide with an anterior resection saw slot configured to guide a saw to make an anterior resection in a distal femur;

an anterior chamfer guide with an anterior chamfer saw slot configured to guide a saw to make an anterior chamfer resection in the distal femur;

a posterior chamfer guide with a posterior chamfer saw slot configured to guide a saw to make a posterior chamfer resection in the distal femur;

a posterior cut guide with a posterior resection saw slot configured to guide a saw to make a posterior resection in the distal femur; and a locking element movably retained by the rail such that the locking element comprises an unlocked position and a locked position in which the locking element has been rotated 90 degrees from the unlocked position;

wherein:

in the unlocked position, at least three of the anterior cut guide, the anterior chamfer guide, the posterior chamfer guide, and the posterior cut guide are slidably coupled to and independently movable along the rail; and in the locked position, the anterior cut guide, the anterior chamfer guide, the posterior chamfer guide, and the posterior cut guide are all fixed relative to each other and not movable along the rail.

16. The system of claim 15, further comprising:

a first spacer configured to engage with the four-in-one cut guide, wherein the first spacer comprises a spacer body, an anterior arm comprising a first anterior-posterior thickness, a middle arm comprising a second anterior-posterior thickness, and a posterior arm comprising a third anterior-posterior thickness, wherein the anterior, middle, and posterior arms are coupled to the spacer body;

wherein when the first spacer is engaged with the four-in-one cut guide, the anterior arm extends between the anterior cut guide and the anterior chamfer guide, the middle arm extends between the anterior chamfer guide and the posterior chamfer guide, and the posterior arm extends between the posterior chamfer guide and the posterior cut guide.

17. The system of claim 16, wherein:

when the first spacer engages the four-in-one cut guide, the anterior cut guide, the anterior chamfer guide, the posterior chamfer guide, and the posterior cut guide are properly positioned, relative to each other, to guide resections of the distal femur to prepare the distal femur to receive a first femoral implant;

the system further comprises a second spacer, sized differently from the first spacer, and configured to engage the four-in-one cut guide; and when the second spacer engages the four-in-one cut guide, the anterior cut guide, the anterior chamfer guide, the posterior chamfer guide, and the posterior cut guide are properly positioned, relative to each other, to guide resections of the distal femur to prepare the distal femur to receive a second femoral implant sized differently from the first femoral implant.

18. The system of claim 15, wherein:

the locking element comprises a generally cylindrical shape with teeth protruding therefrom.

19. The system of claim 18, wherein the teeth of the locking element extend only partway around a circumference of the generally cylindrical shape such that, when the locking element is in the unlocked position, the teeth of the locking element are not aligned with the teeth of the anterior cut guide, the anterior chamfer guide, the posterior chamfer guide, and/or the posterior cut guide.

20. The system of claim 15, wherein the posterior cut guide is rigidly secured to the rail.

* * * * *